United States Patent
Platzek et al.

(10) Patent No.: US 10,392,384 B2
(45) Date of Patent: Aug. 27, 2019

(54) METHOD FOR THE PREPARATION OF (4S)-4-(4-CYANO-2-METHOXYPHENYL)-5-ETHOXY-2,8-DIMETHYL-1,4-DIHYDRO-1-6-NAPHTHYRIDINE-3-CARBOXAMIDE AND RECOVERY OF (4S)-4-(4-CYANO-2-METHOXYPHENYL)-5-ETHOXY-2,8-DIMETHYL-1,4-DIHYDRO-1-6-NAPHTHYRIDINE-3-CARBOXAMIDE BY ELECTROCHEMICAL METHODS

(71) Applicant: Bayer Pharma Aktiengesellschaft, Berlin (DE)

(72) Inventors: Johannes Platzek, Berlin (DE); Kathrin Gottfried, Wuppertal (DE); Jens Assmann, Haan (DE); Giulio Lolli, Köln (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/753,406

(22) PCT Filed: Aug. 18, 2016

(86) PCT No.: PCT/EP2016/069567
§ 371 (c)(1),
(2) Date: Feb. 19, 2018

(87) PCT Pub. No.: WO2017/032678
PCT Pub. Date: Mar. 2, 2017

(65) Prior Publication Data
US 2018/0244668 A1    Aug. 30, 2018

(30) Foreign Application Priority Data

Aug. 21, 2015   (EP) .................... 15182040
Aug. 21, 2015   (EP) .................... 15182042

(51) Int. Cl.
*C25B 3/02*     (2006.01)
*C25B 3/04*     (2006.01)
*C25B 15/08*    (2006.01)
*C07D 471/04*   (2006.01)

(52) U.S. Cl.
CPC .............. *C07D 471/04* (2013.01); *C25B 3/02* (2013.01); *C25B 3/04* (2013.01); *C25B 15/08* (2013.01)

(58) Field of Classification Search
None
See application file for complete search history.

(56) References Cited

U.S. PATENT DOCUMENTS

2008/0312209 A1   12/2008  MacDonald et al.
2010/0136142 A1*   6/2010  Barfacker ............ C07D 471/04
                                                          424/718

FOREIGN PATENT DOCUMENTS

WO    2008104306 A2    9/2008
WO    WO-2008104306 A2 *  9/2008    ........... C07D 471/04

OTHER PUBLICATIONS

A Straub et al, Inversion of Optically Active Dihydropyridines by Oxidation and Electroreduction:, Angew. Chew. Int. Ed., pp. 2662-2664, Jan. 1 (Year: 1996).*

(Continued)

*Primary Examiner* — Zinna Northington Davis
(74) *Attorney, Agent, or Firm* — Ice Miller LLP

(57) ABSTRACT

The present invention relates to a novel process for preparing (4S)-4-(4-cyano-2-methoxyphenyl)-5-ethoxy-2,8-dimethyl-1,4-dihydro-1,6-naphthyridine-3-carboxamide of the formula (I) and recovering (4S)-4-(4-cyano-2-methoxyphenyl)-5-ethoxy-2,8-dimethyl-1,4-dihydro-1,6-naphthyridine-3-carboxamide of the formula (I)

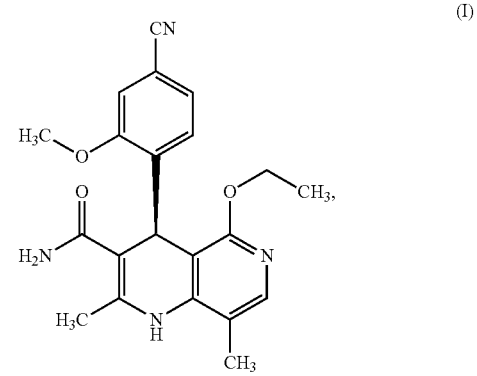

proceeding from (4R)-4-(4-cyano-2-methoxyphenyl)-5-ethoxy-2,8-dimethyl-1,4-dihydro-1,6-naphthyridine-3-carboxamide of the formula ent-(I)

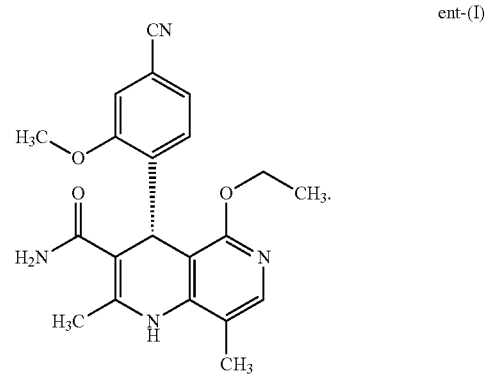

8 Claims, 7 Drawing Sheets

(56) References Cited

OTHER PUBLICATIONS

Kita Y et al, "Selective and facile electroreductive synthesis of dihydro- and tetrahydropyridine dicarboxylic acid derivatives", Tetrahedron Letters, vol. 40, No. 49, pp. 8587-8590, Dec. 3 (Year: 1999).*
Written Opinion of the International Searching Authority for PCT/EP2016/069567, dated Nov. 2 (Year: 2016).*
Abe et al., "Large scale synthesis of N-benzyl-4-formylpiperidine through partial reduction of esters using aluminum hydride reagents modi® ed with pyrrolidine," Tetrahedron 57 (2001) pp. 2701-2710.
Arguello et al., "Voltammetric oxidation of Hantzsch 1,4-dihydropyridines in protic media: substituent effect on positions 3,4,5 of the heterocyclic ring," Electrochimica Acta 49 (2004) pp. 4849-4856.
Bärfacker et al., "Discovery of BAY 94/8862: A Nonsteroidal Antagonist of the Mineralocorticoid Receptor for the Treatment of Cardiorenal Diseases," ChemMedChem 2012, 7, pp. 1385-1403.
Chang et al., "Highly efficient triarylene conjugated dyes for sensitized solar cells," Journal of Materials Chemistry, 2011, 21, pp. 9523-9531.
Chidambaram, "A robust palladium-catalyzed cyanation procedure: beneficial effect of zinc acetate," Tetrahedron Letters 44 (2004) pp. 1441-1444.
David et al., "Electrochemical Behaviour of an Unsymmetrical 4-(o-Nitrophenyl)-1,4-Dihydropyridine in Protic Medium," Tetrahedron 51 (1995) pp. 3181-3196.
Eisner et al., "The Chemistry of Dihydropyridines," Chemical Reviews (1972), 72, pp. 1-42.
Flack et al., "Absolute structure and absolute configuration," Acta Cryst. (1999), A55, pp. 908-915.
Flack et al., "Reporting and evaluating absolute-structure and absolute-configuration determinations," Journal of Applied Crystallography (2000), 33, pp. 1143-1148.
Flack, "On Enantiomorph-Polarity Estimation," Acta Cryst., (1983), A39, pp. 876-881.
Francke et al., "Redox catalysis in organic electrosynthesis: basic principles and recent developments," Chem. Soc. Rev., 43 (8), 2014, pp. 2492-2521.
Fuchigami et al., "Fundamentals and Applications of Organic Electrochemistry: Synthesis, Materials, Devices," First Edition; 2015 John Wiley & Sons, Ltd., pp. 1-10.
Glennon et al., "Binding of Phenylalkylamine Derivatives at 5-HT1C and 5-HT2 Serotonin Receptors: Evidence for a Lack of Selectivity," Journal of Medicinal Chemistry, 1992, vol. 35, pp. 734-740.
Göerlitzer et al., "Untersuchungen zum Reaktionsmechanismus der Bildung einer 9-Hydroxy-β-carbolin-4-carbonsäure aus dem Nifedipin-analogen Biscyanoethylester," Pharmazie, 2000, vol. 55, pp. 747-750.
Grimster et al., "Aromatic Sulfonyl Fluorides Covalently Kinetically Stabilize Transthyretin to Prevent Amyloidogenesis while Affording a Fluorescent Conjugate," Journal of the American Chemical Society, 2013, vol. 135, pp. 5656-5668.
Hagiya et al., "A Facile and Selective Synthetic Method for the Preparation of Aromatic Dialdehydes from Diesters via the Amine-Modified SMEAH Reduction System," Synthesis 2003, No. 6, pp. 823-828.
Han et al., "Facile Entry to an Efficient and Practical Enantioselective Synthesis of a Polycyclic Cholesteryl Ester Transfer Protein Inhibitor," Organic Letters 2014, 16, pp. 4142-4145.
Handbook of Electrochemistry, Elsevier, editor: C.G. Zoski, 2007, p. 819.
Hariprasad et al., "Optimization of reactive SMB and Varicol systems," Computers and Chemical Engineering 27 (2003), pp. 1883-1901.
Hung et al., "A General Route to 5- and 6-Substituted 4-Amino-2-oxo-1,2-dihydropyridines," Synthesis 1984, pp. 765-766.
Kita et al., "Highly selective and facile synthesis of dihydro- and tetrahydropyridine dicarboxylic acid derivatives using electroreduction as a key step," Tetrahedron 57 (2001) pp. 2095-2102.
Kita et al., "Selective and facile electroreductive synthesis of dihydro- and tetrahydropyridine dicarboxylic acid derivatives," Tetrahedron Letters 40 (1999) pp. 8587-8590.
Koop et al., "Stereoselective oxidation of 4-aryl-1,4-dihydropyridines to axially chiral 4-arylpyridines with 2,2,6,6-tetramethyl-1-oxopiperidinium tetrafluoroborate (TEMPO+ BF4-)," Tetrahedron Asymmetry 12 (2001) pp. 341-345.
Lopez-Alarcon et al., "Voltammetric oxidation of Hantzsch 1,4-dihydropyridines in protic and aprotic media: relevance of the substitution on N position," Electrochimica Acta 48 (2003) pp. 2505-2516.
Martin et al., "Open air palladium catalyzed cyanation—the use of PMHS to protect from oxygen," Tetrahedron Letters 48 (2007), pp. 2555-2557.
Ogura, et al., "Total synthesis of acerogenins E, G and K, and centrolobol," Tetrahedron 69 (2013), pp. 2807-2815.
Patrick et al., "Synthesis and in Vitro Antiprotozoal Activities of Dicationic 3,5-Diphenylisoxazoles," J. Med. Chem. 2007, 50, pp. 2468-2485.
Schareina et al., "Improving palladium-catalyzed cyanation of aryl halides: development of a state-of-the-art methodology using potassium hexacyanoferrate(II) as cyanating agent," Journal of Organometallic Chemistry 689 (2004), pp. 4576-4583.
Schareina et al., "A new palladium catalyst system for the cyanation of aryl chlorides with K4[Fe(CN)6]," Tetrahedron Letters 48 (2007), pp. 1087-1090.
Scriven Ed., "Pyridines: From Lab to Production," Elsevier Verlag 2013, Chapter 8, pp. 116-144.
Straub et al., "Inversion optisch aktiver Dihydropyridine durch Oxidation und Elektroreduktion," Angew. Chem., (1996) 108, pp. 2832-2834.
Straub et al., "Inversion of Optically Active Dihydropyridines by Oxidation and Electroreduction," Angew. Chem., (1996) 35, No. 22, pp. 2662-2664.
Tromelin et al., "Šynthèse et étude biologique préliminaire de dérivés dichloréthylamintes sur l'homocycle de nitro-2 benzofurannes," European Journal of Medicinal Chemistry, 1986, vol. 21, pp. 397-402.
Tschaen et al., "An Improved Procedure for Aromatic Cyanation," Synthetic Communications vol. 24. No. 6, 1994, pp. 887-890.
Yamamoto et al., "Structure—activity relationship study of 1,4-dihydropyridine derivatives blocking N-type calcium channels," Bioorganic & Medical Chemistry Letters 16, (2006), pp. 798-802.
Zanon et al., "Copper-Catalyzed Domino Halide Exchange-Cyanation of Aryl Bromides," J. Am. Chem. Soc. 2003, 125, pp. 2890-2891.
Zoski, Handbook of Electrochemistry 2007, Elsevier, pp. 33-56.

* cited by examiner

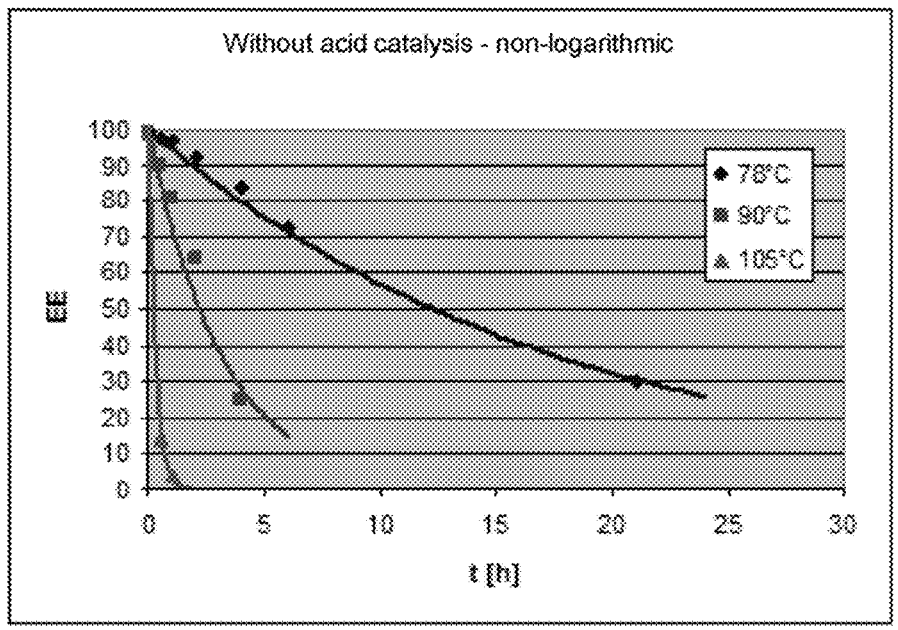
Figure 1: Racemization of the compound of the formula ent-(I) to the compound of the formula (XVII) as a function of temperature and time without addition of a catalytic amount of acid.
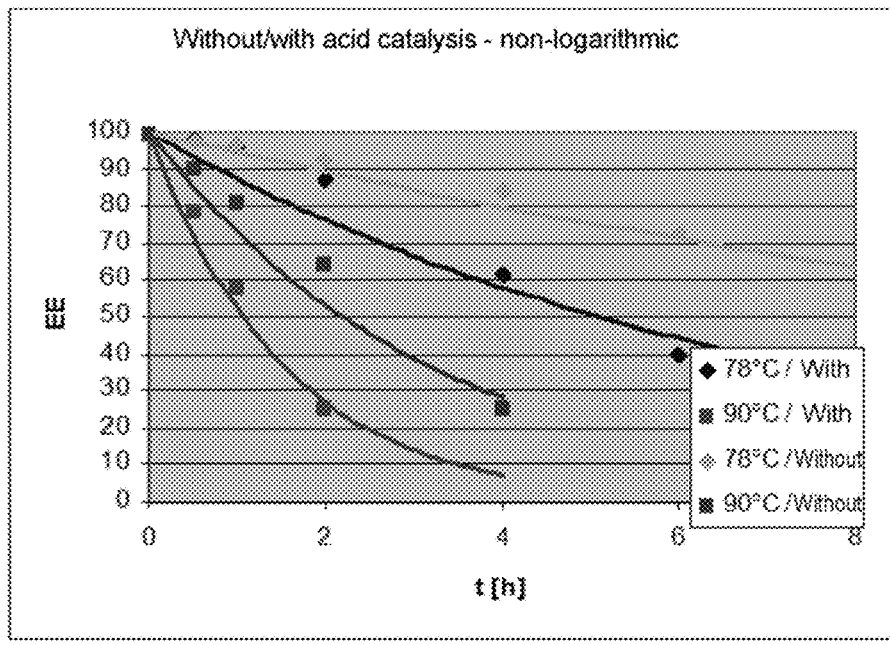
Figure 2: Racemization of the compound of the formula ent-(I) to the compound of the formula (XVII) as a function of temperature and time

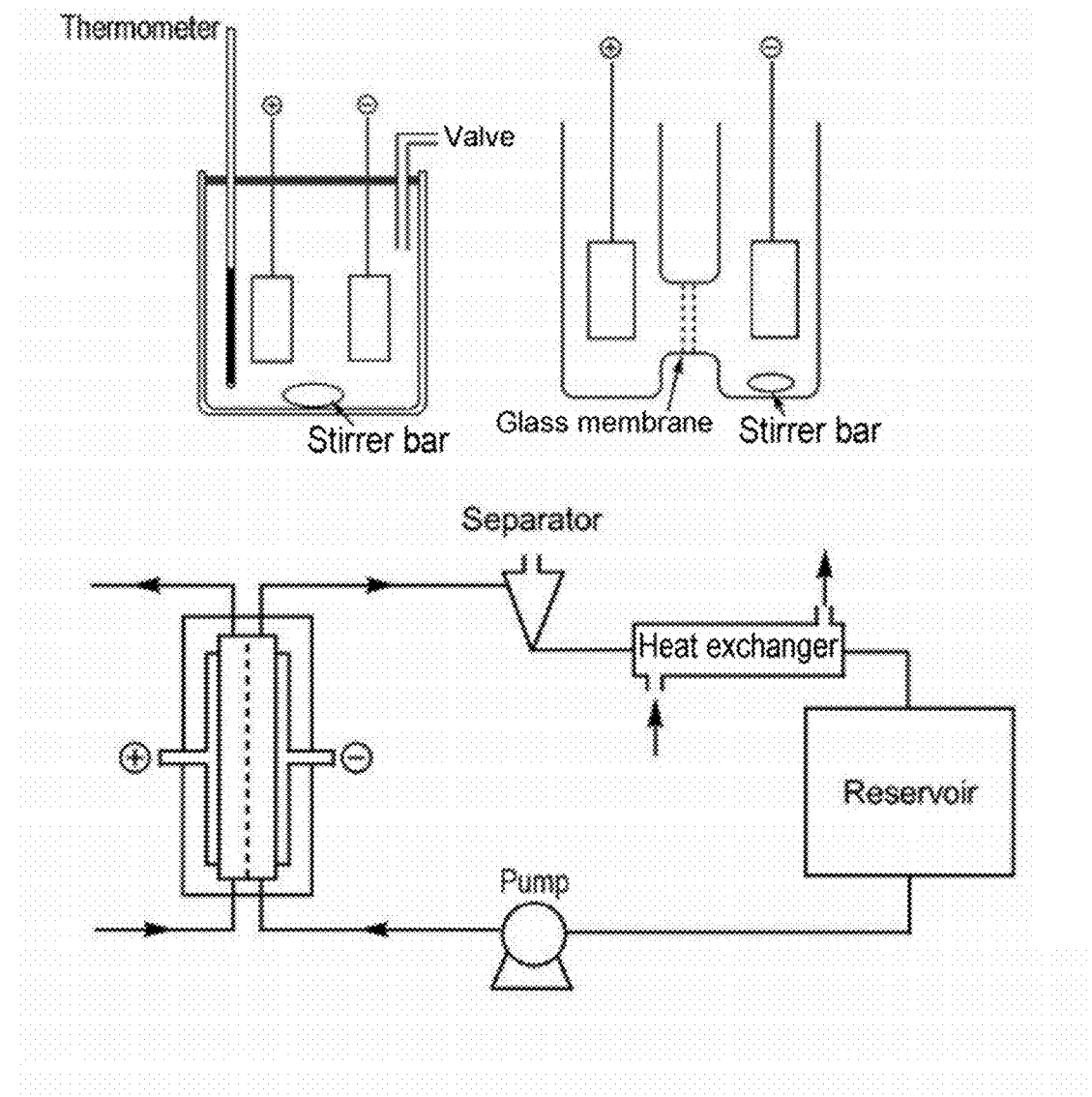
Figure 3: Standard types of electrochemical cells. Beaker cell, "H" cell and filter press flow cell.

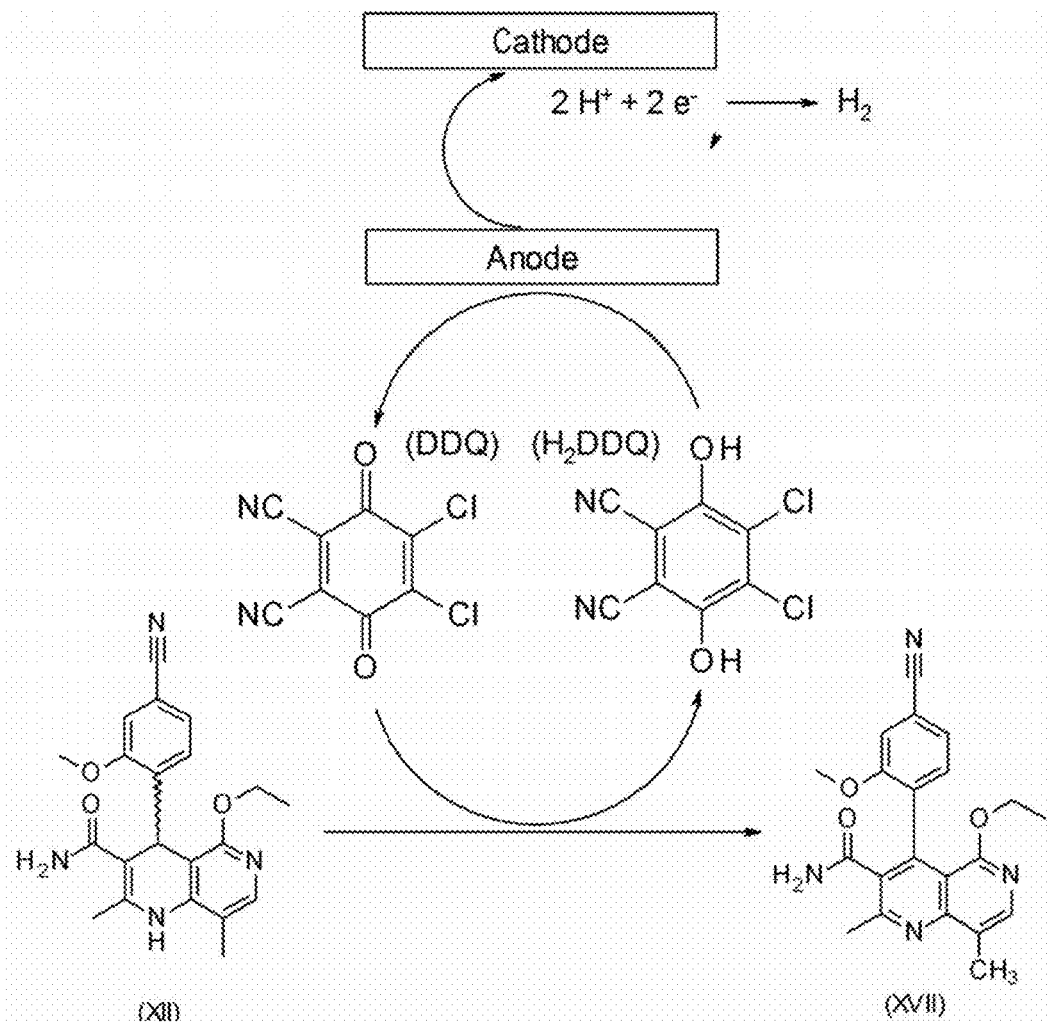
Figure 4: Reaction scheme of the mediated electrochemical oxidation of ent-(I) to (XVII) by DDQ.

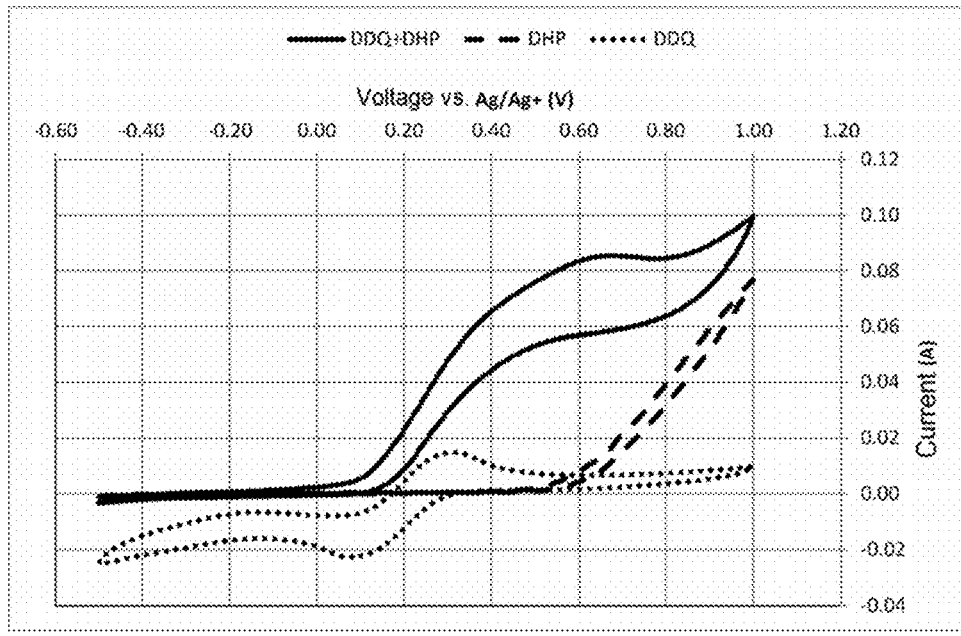
Figure 5: Cyclic voltammetry of DDQ, DHP ent-(I) and the DDQ:DHP (ent-I) 1:10 mixture according to Examples 24 and 25
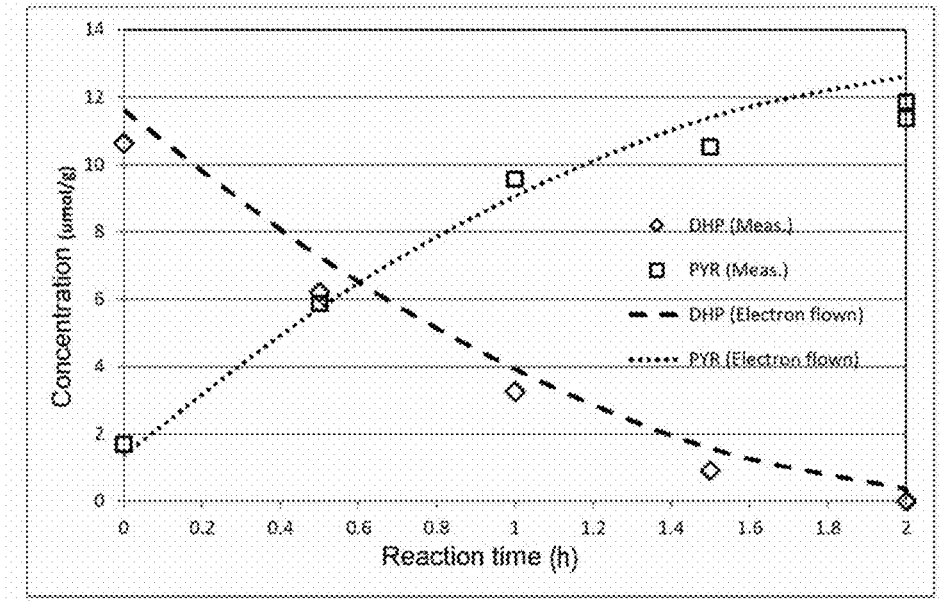
Figure 6: Evolution of DHP reactant (I) and PYR product (XVII) measured by means of HPLC as a function of time according to Example 26. The lines represent the values calculated based solely on electron flow and 100% power efficiency.

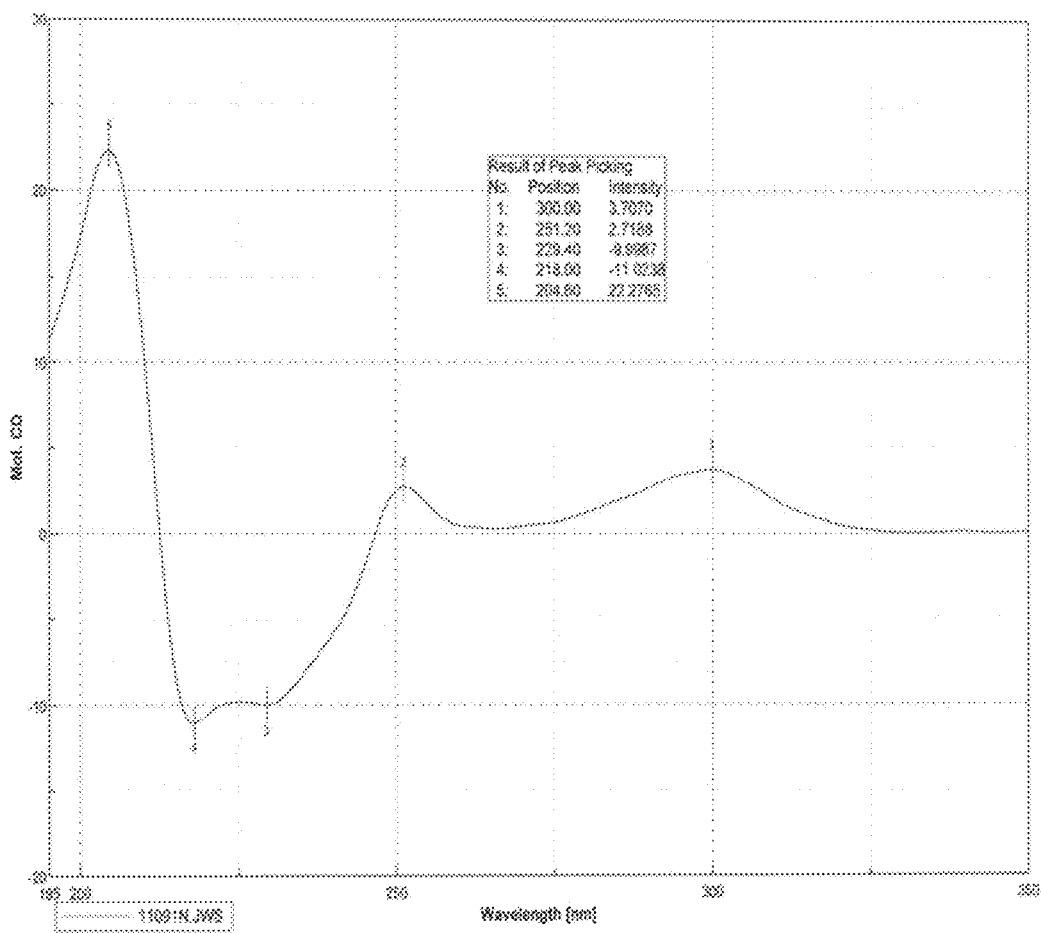
Figure 7: CD spectrum of the compound of the formula M1b(R) (in acetonitrile)

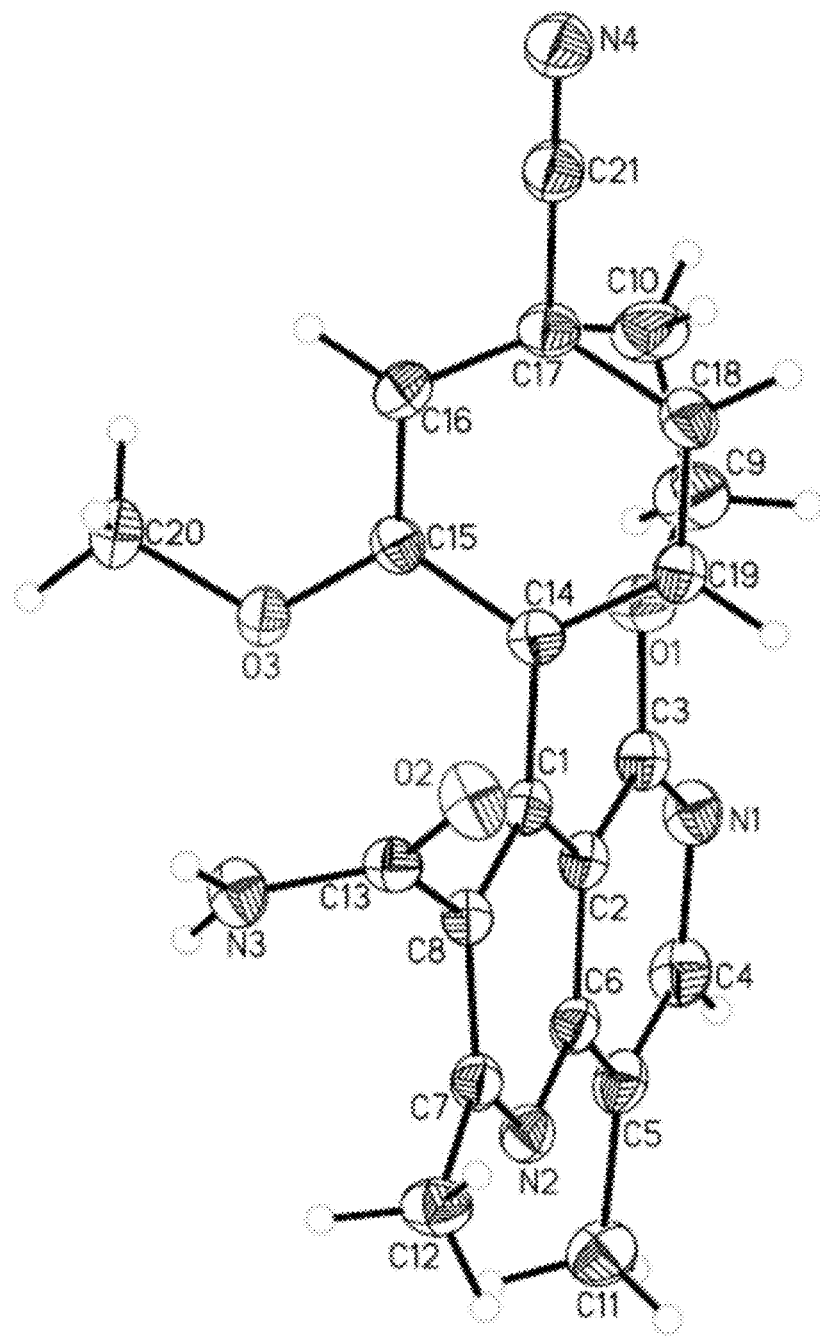
Figure 8: Crystal structure of the compound of the formula M1b(R): (R)-4-(4-cyano-2-methoxyphenyl)-5-ethoxy-2,8-dimethyl-1,6-naphthyridine-3-carboxamide

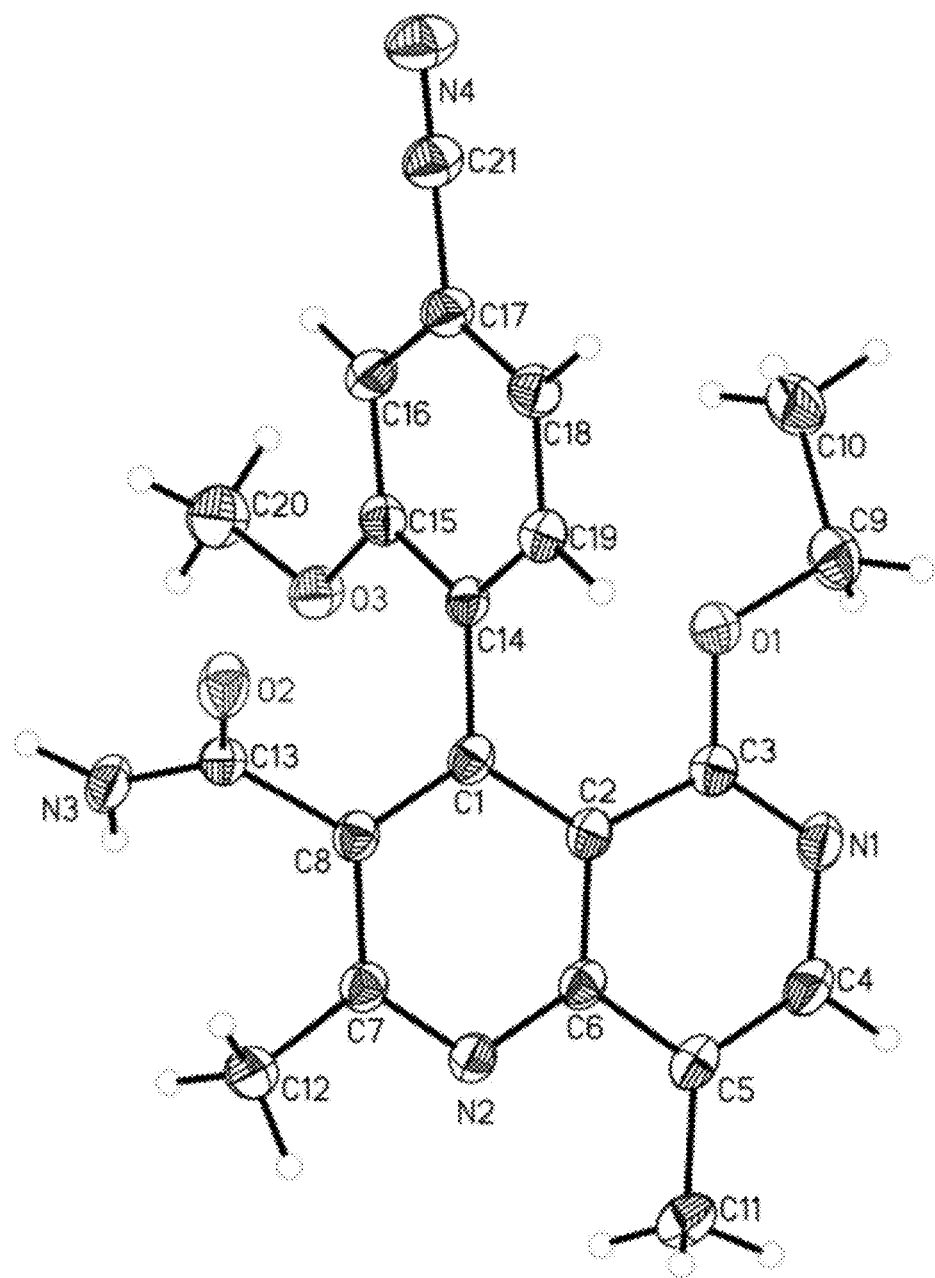
Figure 9: Crystal structure of the compound of the formula M1b(R): (R)-4-(4-cyano-2-methoxyphenyl)-5-ethoxy-2,8-dimethyl-1,6-naphthyridine-3-carboxamide

METHOD FOR THE PREPARATION OF (4S)-4-(4-CYANO-2-METHOXYPHENYL)-5-ETHOXY-2,8-DIMETHYL-1,4-DIHYDRO-1-6-NAPHTHYRIDINE-3-CARBOXAMIDE AND RECOVERY OF (4S)-4-(4-CYANO-2-METHOXYPHENYL)-5-ETHOXY-2,8-DIMETHYL-1,4-DIHYDRO-1-6-NAPHTHYRIDINE-3-CARBOXAMIDE BY ELECTROCHEMICAL METHODS

CROSS-REFERENCE TO RELATED APPLICATIONS

This application claims priority to and is a 35 U.S.C. § 371 national phase application of PCT/EP2016/069567, filed on Aug. 18, 2016. This application also claims priority to European Patent Application No. 15182040.4 filed on Aug. 21, 2015 and European Patent Application No. 15182042.0 filed on Aug. 21, 2015.

The present invention relates to a novel process for preparing (4S)-4-(4-cyano-2-methoxyphenyl)-5-ethoxy-2,8-dimethyl-1,4-dihydro-1,6-naphthyridine-3-carboxamide of the formula (I) and recovering (4S)-4-(4-cyano-2-methoxyphenyl)-5-ethoxy-2,8-dimethyl-1,4-dihydro-1,6-naphthyridine-3-carboxamide of the formula (I)

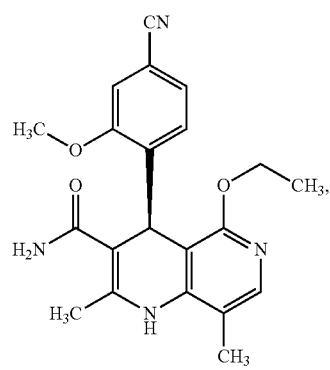

(I)

proceeding from (4R)-4-(4-cyano-2-methoxyphenyl)-5-ethoxy-2,8-dimethyl-1,4-dihydro-1,6-naphthyridine-3-carboxamide of the formula ent-(I)

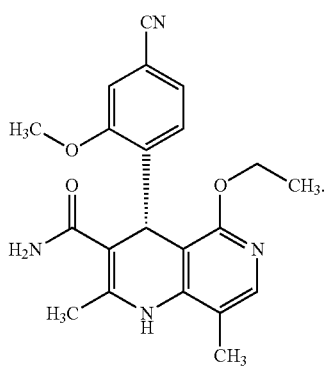

ent-(I)

The compound of the formula (I) acts as a non-steroidal antagonist of the mineralocorticoid receptor and may be used as an agent for prophylaxis and/or treatment of cardiovascular and renal disorders such as heart failure and diabetic nephropathy, for example.

The compound of the formula (I) and the preparation process thereof are described in WO2008/104306 and Chem Med Chem 2012, 7, 1385, both publications disclosing a detailed discussion of the research synthesis. A disadvantage of the synthesis described therein is the fact that this synthesis is unsuitable for a large-scale process, since many steps proceed at very high dilution, with very high excesses of reagents and therefore afford a relatively low overall yield. Furthermore, many intermediate chromatographic purifications are necessary, which are technically generally very laborious and entail a high consumption of solvents, are costly and are therefore to be avoided if possible. Some stages are not achievable due to safety and process technology difficulties.

There existed a need, therefore, for an industrially practicable synthesis, which affords the compound of the formula (I) in a reproducible manner in high overall yield, low production costs and high purity and meets all regulatory requirements, in order to provide clinical trials with active ingredient and to be used for later regulatory submission.

A very efficient synthesis has been found which allows the requirements mentioned above to be met.

In the publication Chem Med Chem 2012, 7, 1385, which discloses the research scale synthesis of the compound of the formula (I), the compound of the formula (I) is prepared in 10 stages starting from vanillin with an overall yield of 3.76% of theory. The compound of the formula (I) was obtained by evaporation of chromatographic fractions as an amorphous solid; a defined crystallisation process for the final stage for polymorphic adjustment has not been described to date.

The following scheme 1 shows the known process for preparing the compound of the formula (I).

Scheme 1: Research scale synthesis of the compound of the formula (I)

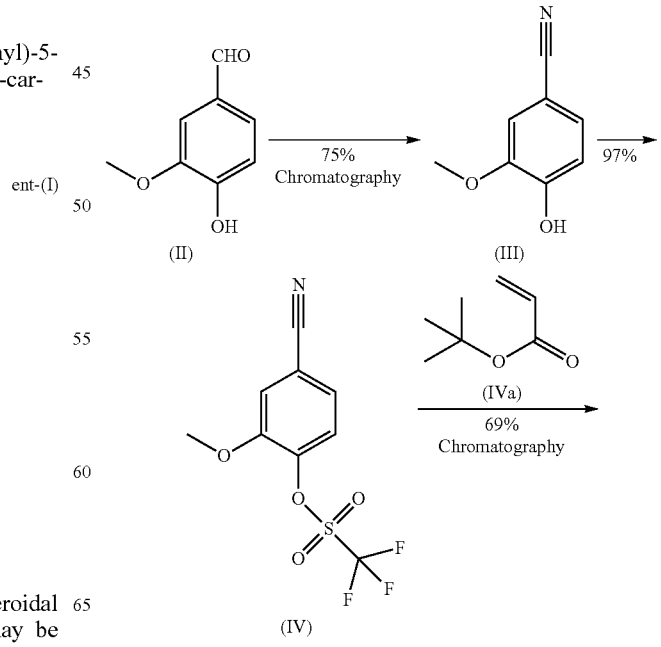

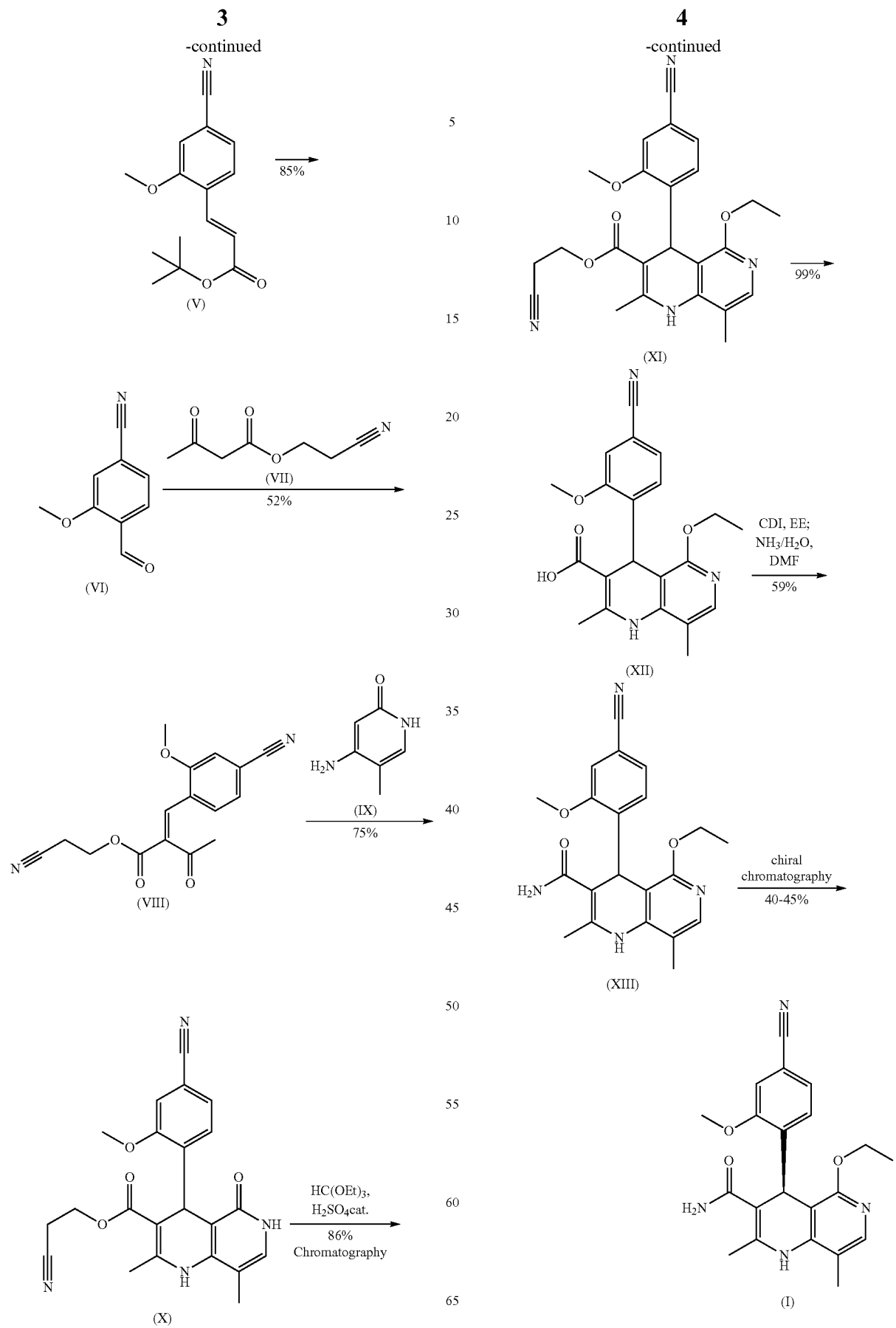

Three chromatographic purifications are utilised and also a chiral chromatography stage for separating the enantiomers of the racemate of the formula (XIII). Some of the stages proceed at very high dilution and using very large amounts of reagent.

For instance, the sequence of the preparation of the nitrile-aldehyde intermediate (VI) in particular, which takes on a central role in this synthesis, is unacceptable in terms of atom economy.

Furthermore, this process cannot be transferred to an industrial scale since first of all very expensive reagents are used, such as trifluoromethanesulphonic anhydride [(III)=>(IV)] and excesses of tert-butyl acrylate. On scaling up the Heck reaction (IV)=>(V), a residue similar to plastic forms in the tank, which originates from the polymerisation of the tert-butyl acrylate used in excess. This is unacceptable in an industrial procedure, since the danger exists that it can cause a fracture of the stirrer and would lead to residues in the stirrer mechanism that are too hard to remove.

The subsequent cleavage of the double bond with sodium periodate and the highly toxic osmium tetroxide should also be avoided since, under the experimental conditions described, a delay of the reaction occurs and results in a strong exothermicity and therefore links to a runaway reaction.

Scheme 2 illustrates a novel process which affords the compound of the formula (I) in 9 stages in an overall yield of 27.7% of theory without chromatographic purification of intermediates.

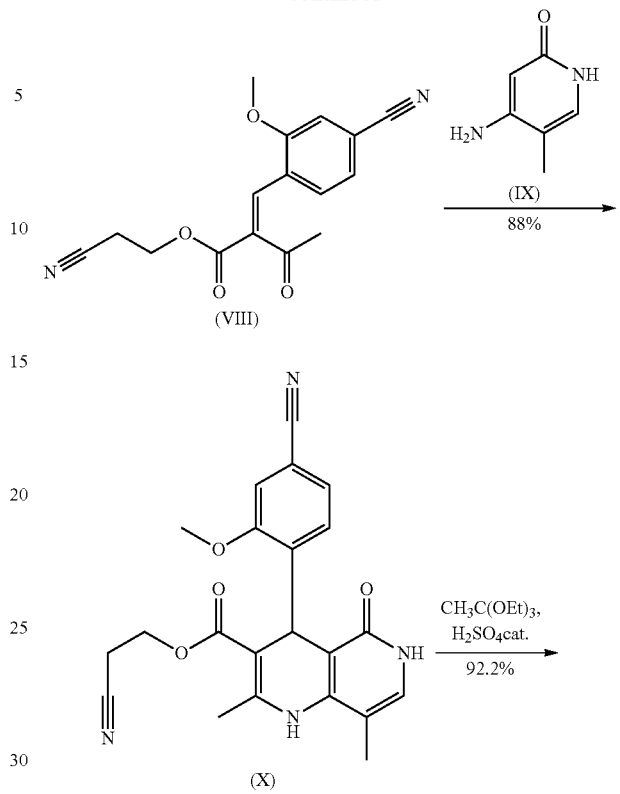

Scheme 2: Novel process for preparing the compound of the formula (I).

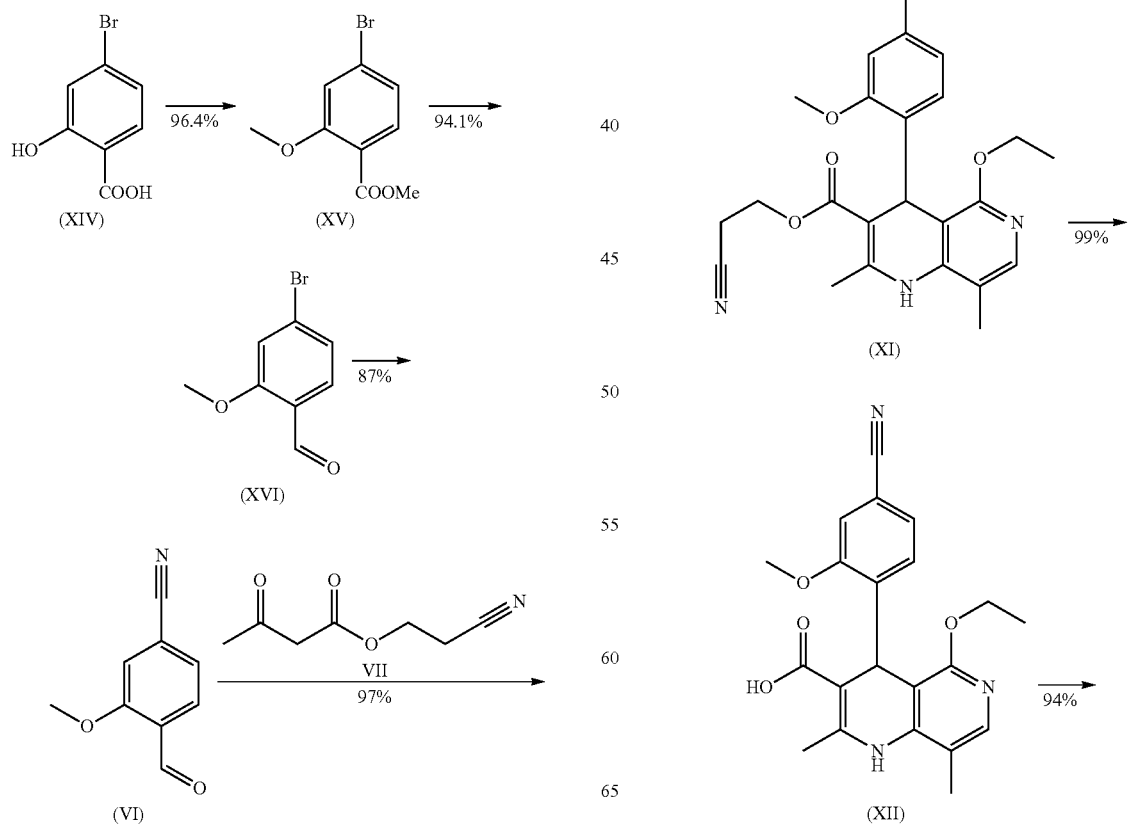

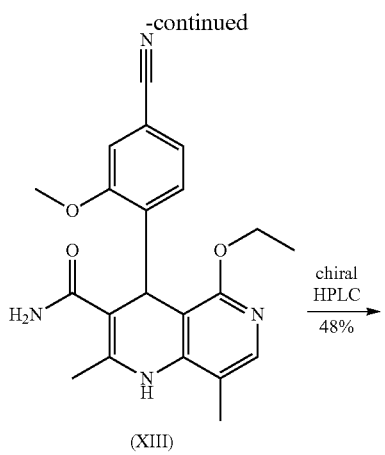

(XIII)

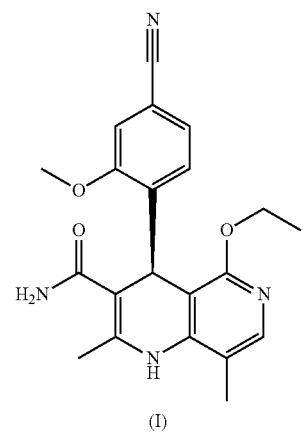 [SMILES: CCOc1ncc(C)c2c1[C@H](c1ccc(C#N)cc1OC)C(C(N)=O)=C(C)N2 ; "(I)"]

(I)

The methyl ester (XV) and the aldehyde (XVI) are not isolated but are further reacted directly in solution, which results in only 7 stages to be isolated. A preparative chiral HPLC method (e.g. SMB Technology, Varicol) is used for the enantiomer separation.

The aldehyde (VI) is known from the literature (J. Med. Chem. 2007, 50, 2468-2485) and constitutes an important intermediate in this synthesis. It is now also possible to purchase the compound commercially.

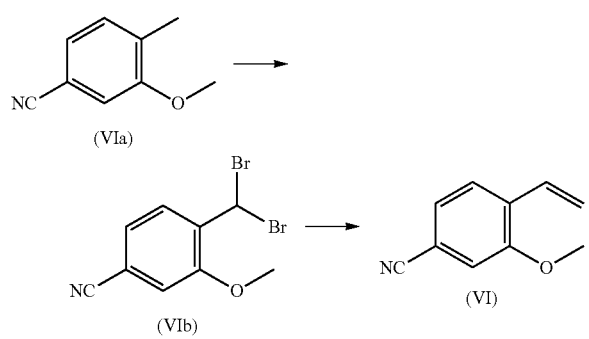

Starting from 4-cyano-2-methoxytoluene (VIa), a dibromide (VIb) is prepared with NBS, which is reacted in ethanol with 2.46 eq. of silver nitrate (in water) to give the target aldehyde (VI). This synthesis described in the literature and the process described in the research scale synthesis are completely unsuitable for scaling up to the multi-tonne scale such that a great need existed for a novel, more efficient and economically more viable synthesis.

The halobenzoic acids (XIV) and (XIVa)

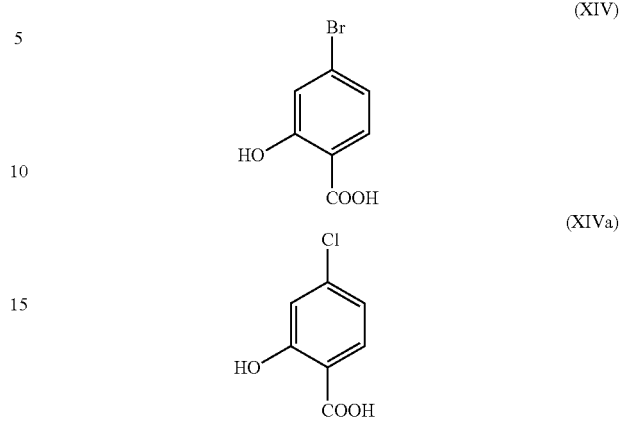

are commercially available in relatively large amounts. A very efficient and cheaper process has been developed in which the intermediates (XV) and (XVI)

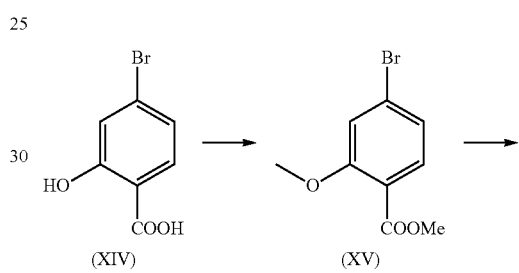

are not isolated but are further reacted dissolved in solution. This is only possible because the yield and purity of each reaction is very high (>95% of theory). The methyl ether ester (XV) is known from the literature (Journal of Medicinal Chemistry, 1992, vol. 35, p. 734-740) and is prepared by reaction with methyl iodide, which is very volatile, harmful to health and costly.

With the novel process it was possible to show that the non-volatile, less expensive dimethyl sulphate can be used analogously. Starting from the acid (XIV), said acid is reacted in a solvent such as acetone, 2-butanone, THF, 2-methyl-THF, DMF, DMA or NMP with dimethyl sulphate with the aid of an auxiliary base such as potassium carbonate, sodium carbonate, calcium carbonate, lithium carbonate, N-methylimidazole, triethylamine, pyridine or 2,6-lutidine at temperatures of 50-100° C. to give the methyl ether ester (XV). This is a method known to those skilled in the art for esterification of acids and etherification of phenols (Tetrahedron, 2013, vol. 69, p. 2807-2815, Journal of the American Chemical Society, 2013, vol. 135, p. 5656-5668). The reaction in acetone under reflux (56° C.) using dimethyl sulphate and potassium carbonate has been found to be particularly preferred. In this case, dimethyl sulphate is added to the boiling reaction mixture over 4 hours. The acetone is distilled off and replaced by toluene (redistillation). For the work-up, water is added (decomposing the excess dimethyl sulphate), the toluene phase is separated and washed with water and saturated sodium chloride solution and the toluene solution subsequently distilled off to a certain volume (serves as azeotropic drying, i.e. removal of water for the subsequent stage). Determination of the solution content indicates virtually complete conversion (>96% of theory). Instead of the bromine compound, the chlorine compound may be used analogously for which the achieved conversions are identical to the bromine compound.

The preparation of the aldehyde (XVI) is described in the literature, examples of which include: Glaxo Group Limited US2008/312209 A1, 2008, European Journal of Medicinal Chemistry, 1986, vol. 21, p. 397-402, Journal of Medicinal Chemistry, 1992, vol. 35, p. 734-740, Journal of Materials Chemistry, 2011, vol. 21, p. 9523-9531. However, the starting materials used in the reactions are very expensive and not obtainable in large amounts, therefore a new method starting from the methyl ether ester (XV) was developed. The conversion of (XV) to the aldehyde (XVI) is possible using REDAL (sodium bis(2-methoxyethoxy)aluminium dihydride) in toluene by addition of N-methylpiperazine. This method is described in the literature (Synthesis 2003, No. 6, 823-828 and Tetrahedron 57 (2001) 2701-2710). If the reaction is carried out analogously to the stoichiometry stated in the literature, a further compound is found in the mixture in addition to the aldehyde. It was shown that this is the corresponding benzyl alcohol which is formed by overreduction of up to 10%. It was shown that it is important to adjust the stoichiometry of the REDAL and N-methylpiperazine to exactly 1.21 eq. of REDAL+1.28 eq. of N-methylpiperazine; in that case, it is possible to reduce the level of this by-product, which is disruptive in the subsequent crystallization stage, down to <1%. For this purpose, a 65% REDAL solution in toluene at 0-5° C. is charged (preferably 1.21 eq.) and 1.28 eq. of N-methylpiperazine are metered in. The solution of REDAL with N-methylpiperazine thus obtained is added over about 30 minutes to the bromo methyl ester solution (XIV) charged in toluene and the mixture is subsequently stirred for one hour at 0° C. The reaction solution is quenched in water/acid, preferably aqueous sulphuric acid and the toluene phase is separated and washed with water and saturated sodium chloride solution. The toluene is distilled off and redistilled in DMF (solvent for the subsequent stage). The reaction yield is generally >94% of theory. The corresponding reaction with the chloro compound proceeds analogously and the yields are equivalent. The DMF solution is used directly in the subsequent reaction.

Later on in the synthesis, the bromoaldehyde (XVI) is converted to the nitrile in a manner known per se by methods familiar to those skilled in the art (Synth. Commun. 1994, 887-890, Angew. Chemie 2003, 1700-1703, Tetrahedron Lett. 2007, 2555-2557, Tetrahedron Lett. 2004, 1441-1444, JACS 2003, 125, 2890-2891, Journal of Organometallic Chemistry 689 (2004), 4576-4583); this affords the nitrile aldehyde (VI). It has proven particularly advantageous in the case of the bromo compound to carry out a palladium-catalysed reaction with potassium hexacyanoferrate*3H$_2$O as the cyanide source (Tetrahedron Lett. 48 (2007), 1087-1090). For this purpose, the bromoaldehyde (XVI) is initially charged in DMF (8-10 times the amount), 0.22 eq. of potassium hexacyanoferrate*3H$_2$O and 1 eq. of sodium carbonate are initially charged, and then 0.005 eq. of palladium acetate is added. The mixture is heated to 120° C. for 3 hours. The solution is cooled to 20° C., then water and ethyl acetate is added. The ethyl acetate phase is separated off, the water phase washed again with ethyl acetate and the combined ethyl acetate phases then redistilled in isopropanol. The product precipitates by water precipitation at the boiling temperature. After isolation, the product is dried under vacuum. In some cases, the product was precipitated directly by addition of water to the DMF and used directly in the subsequent stage after isolation and drying. The yields of this reaction are generally >85% of theory. Palladium acetate is inadequate for the conversion of the chlorine compound; it has been found here to be advantageous to use the palladium catalysts familiar to those skilled in the art, as described in Tetrahedron Lett. 48 (2007), 1087-1090; the yields are somewhat lower than in the case of the bromine compound, generally 80-85% of theory.

The cinnamic ester (VIII a,b) is obtained as an E/Z mixture starting from the aldehyde of the formula (VI) by a Knoevenagel reaction with the cyano ester (III):

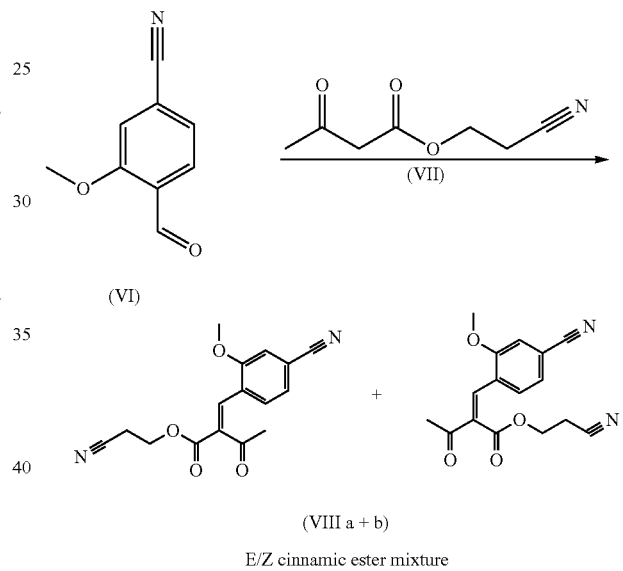

E/Z cinnamic ester mixture

In the research method, the mixture was heated in 16.6 times the amount of dichloromethane and 0.2 eq of piperidine/0.2 eq of glacial acetic acid on a water separator for 20 hours. After aqueous work-up, the product is crystallized from methanol after evaporation of the solvent, the target compound being obtained at 52% of theory.

The reaction proceeds preferably in boiling dichloromethane (10 times the amount) by addition of 5-20 mol % of piperidine, preferably 10 mol % and 5-20 mol % of glacial acetic acid, preferably 5-10 mol %, on a water separator. The reaction time is 4-12 h, but preferably 5-6 h, particularly preferably 6 h. The cyano ester (VII) is added in 1.0-1.5 eq, but preferably 1.1 to 1.35 eq. Particularly preferably 1.1 eq. The preparation of the cyano ester (VII) is described in Pharmazie, 2000, vol. 55, p. 747-750 and Bioorg. Med. Chem. Lett. 16, 798-802 (2006). After completion, the reaction is cooled to 20° C. and the organic phase is washed twice with water. The organic wash is redistilled in 2-butanol and the E/Z cinnamic ester mixture (VIII a+b) is used directly without intermediate isolation in the subsequent reaction with the heterocycle (IX) to give the dihydropyridine (X):

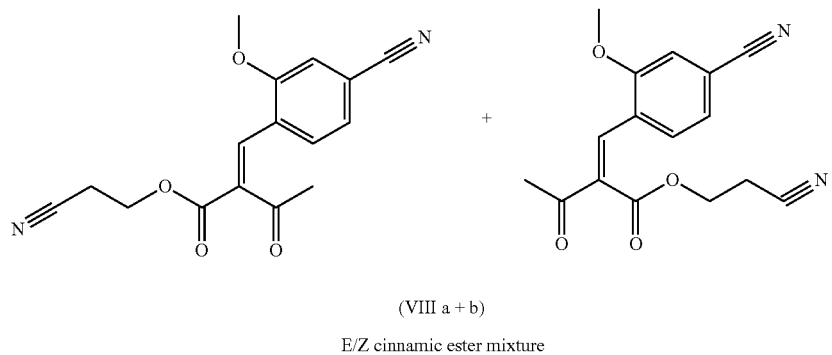 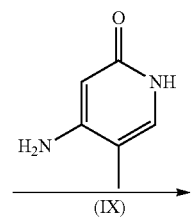

(VIII a + b)
E/Z cinnamic ester mixture

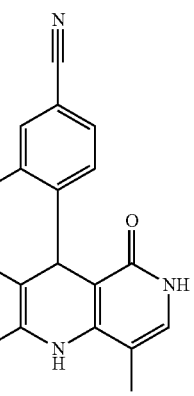

(X)

For the further reaction in the research scale synthesis, the mixture was heated under reflux with the heterocycle (IX) in isopropanol for 40 hours.

It has been found that the reaction may be carried out, preferably in a secondary alcohol such as isopropanol, isobutanol, 2-amyl alcohol or cyclohexanol at temperatures of 80-160° C., at atmospheric pressure and also in autoclaves (2-10 bar), with reaction times of 8-40 h, but preferably for 20-25 h in boiling 2-butanol at atmospheric pressure or else in isopropanol in an autoclave (100° C., 2-10 bar, preferably 3-5 bar, 8-24 h). For work-up, the mixture is cooled to 0° C. to 20° C., and the crystals are filtered off and washed with isopropanol and then dried (in vacuum, 60° C.).

If the use of dichloromethane is to be dispensed with for environmentally economic reasons, it has proven to be advantageous to prepare the cinnamic ester (VIII a,b) in isopropanol, in which case the aldehyde (VI) is charged in isopropanol (3-9 times the amount, preferably 5-7 times the amount) and 5-20 mol % of piperidine, preferably 5-10 mol %, and 5-20 mol % of glacial acetic acid, preferably 5-10 mol %, is added. At 30° C., 1.0-1.5 eq., preferably 1.1-1.35 eq., particularly preferably 1.1 eq., of cyano ester (VII), optionally dissolved in a little isopropanol, is metered in over the course of 3 hours and the mixture is stirred at 30° C. for 1 hour. The cinnamic ester (VIIIa,b) crystallizes out during the reaction. The product is subsequently filtered off, optionally after cooling, preferably at 0° C., washed with a little isopropanol (cooled to 0° C.) and used moist in the subsequent reaction as described above. The yield is >96% of theory. The subsequent reaction is preferably performed in 10-15 times the amount (with respect to aldehyde (VI)), preferably 11-12 times the amount, of isopropanol for 20-24 hours at 100° C. under pressure. After termination of the reaction and cooling, the product is isolated by filtration or centrifugation. The product is subsequently dried at 40-90° C. under vacuum. Since the conversion to the cinnamic ester proceeds virtually quantitatively, the process for the subsequent stage can be readily standardised without having to adjust the amount of heterocycle (IX) in each case, as the product can be used moist with isopropanol. The yields are >87% of theory. The heterocycle (IX) can be prepared by known literature methods such as is described, for example, in Synthesis 1984, 765-766.

Starting from the dihydropyridine (X), the ethyl ether (XI) is obtained by reaction under acidic catalysis with an orthoester, where R is —H or -methyl:

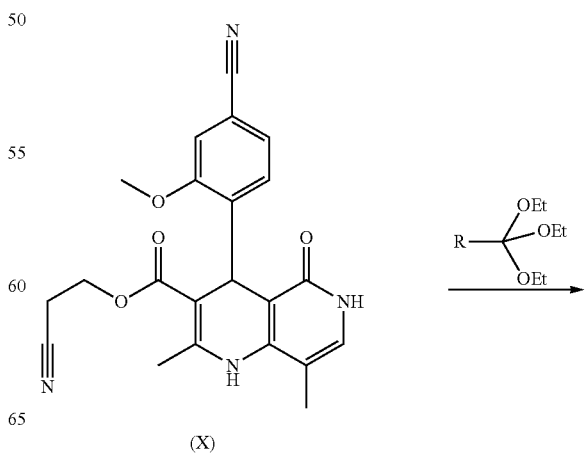

(X)

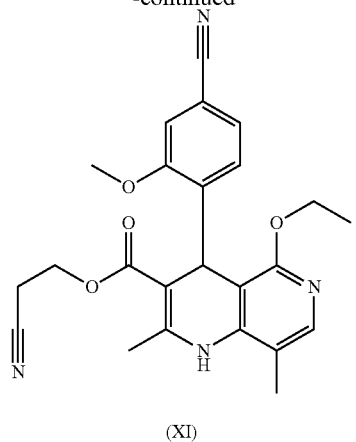

(XI)

R = H, Me

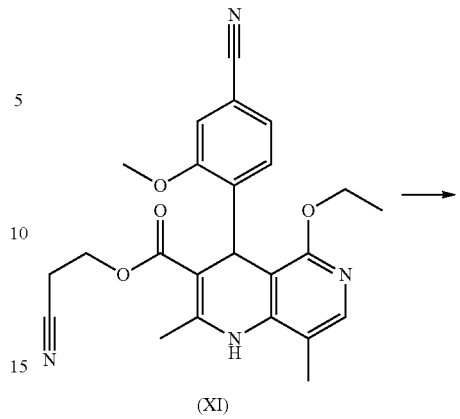

(XI)

In the research scale synthesis, for this purpose, the reaction was carried out in 25 times the amount of DMF with 20.2 eq. of triethyl orthoformate and a catalytic amount of conc. sulphuric acid at 135° C. The mixture was concentrated to dryness and the residue was purified by chromatography with a yield of 86% of theory. This method is unsuitable as a technical procedure due to the high dilution and the use of triethyl orthoformate, highly flammable at low temperature, which is used in very large excess, and the subsequent chromatography.

It has been found, surprisingly, that the reaction can be carried out highly concentrated (up to 1.5 g of solvent per 1 g of reactant) in solvents such as dimethylacetamide, NMP (1-methyl-2-pyrrolidone) or DMF (dimethylformamide) by addition of 4-10% strength by weight, preferably 6-8% strength by weight, conc. sulphuric acid. The reaction then surprisingly proceeds with only 2.5-5 eq. of orthoester. It has been found that it is much more convenient to use the corresponding triethyl orthoacetate in the reaction, since it reacts much more cleanly on the one hand and is much less inflammable, making it particularly appropriate for the technical procedure. The reaction is preferably carried out in DMA (dimethylacetamide) and NMP (1-methyl-2-pyrrolidone), at temperatures of 100-120° C., preferably 115° C. Before starting the actual reaction, it has proven advantageous to distil off some of the solvent (DMD or NMP) at elevated temperature (100-120° C. under vacuum) in order to remove any residues of isopropanol present from the precursor, as otherwise undesirable by-products occur. Reaction: Stir for 1.5-3 hours, preferably 2 hours. For the work-up, water is added directly to the mixture, wherein the product crystallizes out. In order to have a particularly stable and reproducible process, a portion of the water (e.g. ⅓) is first added, then seed crystals are added, and the remaining amount of the water is added. This procedure guarantees that the same crystal polymorph is always obtained, which shows the optimum isolation characteristics. The product is washed with water and dried. The yields are >92% of theory.

Starting from the ethyl ether (XI), the acid (XII) is obtained by alkaline saponification and subsequent acidic work-up:

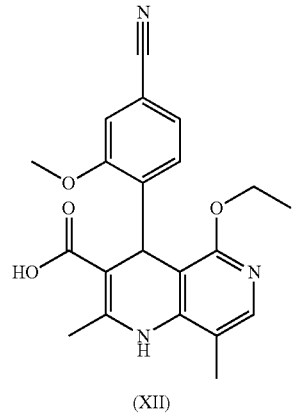

(XII)

In the research scale synthesis, the saponification was carried out at high dilution (33.9 times the amount) in a mixture of DME/water 3:1. Here, it was essential primarily to increase throughput and to replace the DME (dimethoxyethane) used, which has a very low flash point and is therefore considered to be particularly critical for large-scale use. It has been found, surprisingly, that the reaction can also be conducted very readily highly concentrated in mixtures of THF/water. For this purpose, the reaction is preferably performed in a mixture of THF/water 2:1 (9 times the amount), the aqueous sodium hydroxide solution is added at 0-5° C., then the mixture is stirred at 0-5° C. for 1-2 hours. Aqueous potassium hydroxide can also be used but NaOH is preferably used. For the work-up, the mixture is extracted with MTBE (methyl tert-butyl ether) and ethyl acetate and for the isolation the pH is adjusted with a mineral acid such as hydrochloric acid, sulphuric acid or phosphoric acid, but preferably hydrochloric acid, to pH 6.5-7.0. The mixture is then mixed with saturated ammonium salt solution of the corresponding acid, but preferably ammonium chloride solution, wherein the product quantitatively crystallizes out. After isolation, the product is washed with water and with ethyl acetate or acetonitrile or acetone, but preferably acetonitrile, and dried under vacuum at 40-50° C. The yield is virtually quantitative (99%). Alternative preferred work-up: As an alternative work-up, toluene is added to the mixture, sodium acetate is added and the mixture is stirred at 20° C., the phases are then separated and the aqueous phase is adjusted to pH 6.5-7.0 at 0° C. with 10% aqueous hydrochloric acid (may optionally be seeded at pH 9.5-10). The mixture is briefly stirred and the product filtered off, washed with a little water and toluene and dried at 40-50° C. under vacuum. The yields achieved are also quantitative in this case.

The subsequent conversion of the acid to the amide (XIII) was carried out in the research stage as follows: The acid (XII) was dissolved in about 10 times the amount of DMF, 1.25 eq. of 1,1'-carbodiimidazole and 0.1 eq. of DMAP (4-(dimethylamino)pyridine) were added and the mixture was stirred at room temperature for 4 hours. Subsequently, 20 eq. of ammonia were added in the form of an aqueous 25% solution and this mixture was transferred to an oil bath preheated to 110° C. In this procedure, relatively large amounts of ammonia gas form instantaneously, which escape the system and in addition ensure a sharp increase in pressure. This mixture was added to about 90 times the amount of water and adjusted to pH 7 by addition of sodium acetate. The precipitated product was filtered off and dried (yield: 59% of theory). A further portion was isolated from the mother liquor by exhaustive extraction (about 100 times the amount of ethyl acetate), which was stirred with highly flammable diethyl ether and contained about 14% DMF. It is clear that such a method cannot be achieved in such a manner in an operational framework and therefore there is a high demand for an alternative procedure. The effort required for the isolation of this portion is disproportionate to the amount isolated in this case.

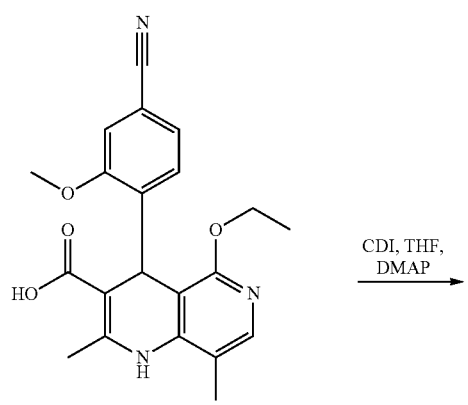

(XII)

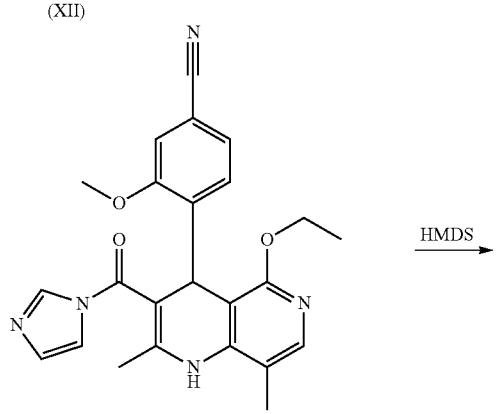

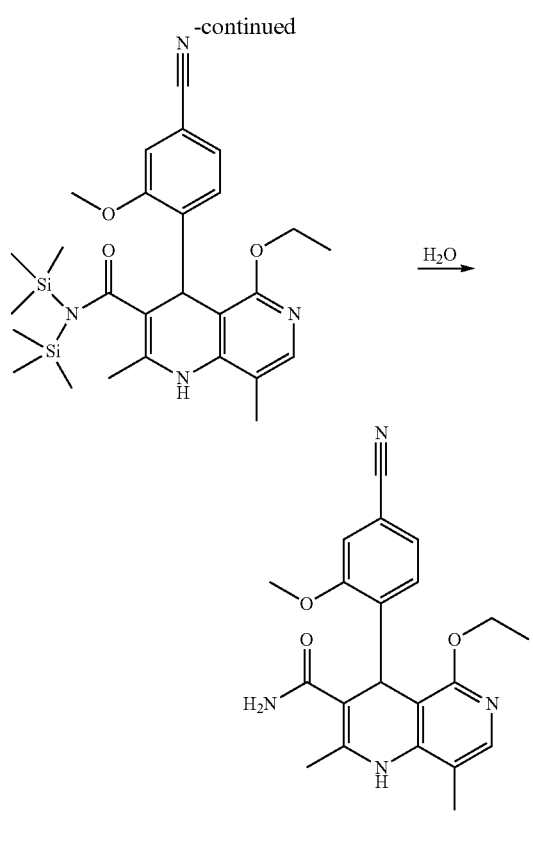

(XIII)

It has been found, surprisingly, that in the reaction of the acid (XII) in THF, the amide (XIII) crystallises out directly from the solution and can be obtained in high yield and purity. For this purpose, the carboxylic acid (XII) is reacted with 1.1 to 1.6 eq., preferably 1.3-1.4 eq., of 1,1'-carbodi-imidazole under DMAP catalysis (5-15 mol %, preferably 10 mol %) in THF to give the imidazolide, which takes place at temperatures between 20-50° C., the preferred approach having proven to be initially starting at 20° C., then stirring 1 to 2 hours at this temperature and then further stirring at 50° C. for 2 to 3 hours. After the activation has ended, 3-8 eq., preferably 4.5 eq., of hexamethyldisilazane are added and the mixture is boiled for 16-24 hours, but preferably for 16 hours, under reflux. The resulting disilylamide compound here can optionally be isolated but it has been proven to be advantageous to continue in a one-pot reaction. Therefore, on completion of the reaction, the mixture is cooled to 0-3° C. and a mixture of water or a mixture of water with THF is added, it having proven to be advantageous to use 0.5 to 0.7 times the amount of water (with respect to reactant), an amount of 0.52 times the amount of water being particularly advantageous. The water can be added directly or as a mixture with approximately an equivalent up to double the amount of THF by volume. After quenching is complete, the mixture is heated to reflux for 1-3 hours in total, preferably 1 hour. The mixture is cooled to 0° C. and stirred for 1-5 hours, preferably 3 hours, at this temperature, then the product is isolated by filtration or centrifugation. The product is washed with THF and water and dried under vacuum at elevated temperature (30 to 100° C., preferably at 60° C. to 90° C.). The yields are very high and are generally >93% of theory. The purity is generally >99% (HPLC, 100% method). The compound (XIII) may also be obtained directly by reacting with ammonia gas in the autoclave (about 25 to 30 bar). For this purpose, the preactivation described above is carried out and the reaction mixture is then heated under pressure under gaseous ammonia. On completion of the reaction, it is cooled and the product filtered off. The yields and purities thus achieved are comparable.

To obtain the compound of the formula (I), the racemic mixture of the amides of the formula (XIII) must be separated into the antipodes. In the published research scale synthesis, a specifically synthesized chiral phase was used for this purpose (prepared in-house), which comprised N-(dicyclopropylmethyl)-N²-methacryloyl-D-leucinamide as chiral selector. This selector was prepared in a multi-stage process and then polymerized on special silica gel. Methanol/ethyl acetate served as eluent. A major disadvantage of this method was the very low loading, 30 mg per separation on a 500*63 mm chromatography column, such that there was a high need to find as effective a separation method as possible which allows separation of antipodes to be performed in the multi-tonne range. It has been found, surprisingly, that the separation can also be performed on a readily commercially available phase. This takes the form of the phase Chiralpak AS-V, 20 μm. The eluent used was a mixture of methanol/acetonitrile 60:40. This mixture has the major advantage that it can be recovered as eluent after distillative work-up having the identical composition (60:40 corresponds to the azeotrope). A very efficient process is achieved in this way in which the yield of the separation is >47% of theory (50% is theoretically possible). The optical purity here is >93% e.e. but preferably >98.5% e.e. In this case, the chromatography may be carried out on a conventional chromatography column, but preferably the techniques known to those skilled in the art such as SMB or Varicol (Computers and Chemical Engineering 27 (2003) 1883-1901) are used. For instance, about 500 kg of the racemic amide of the formula (XIII) was separated using an SMB system, in which a yield of 48% was achieved. The product is obtained as a 3-8%, preferably 5-7% solution in a mixture of methanol/acetonitrile 60:40 and can be used directly in "final processing". Other solvent mixture ratios of acetonitrile to methanol are also conceivable (90:10 to 10:90). Alternatively, other solvent mixtures can also be used, however, for the SMB separation, such as acetonitrile/ethanol in mixture ratios of 10:90 to 90:10. The particular solvent ratio depends partly on the technical properties of the SMB system and must be adjusted, if appropriate (e.g. varying flow rate, recycling of the solvent on a thin film evaporator).

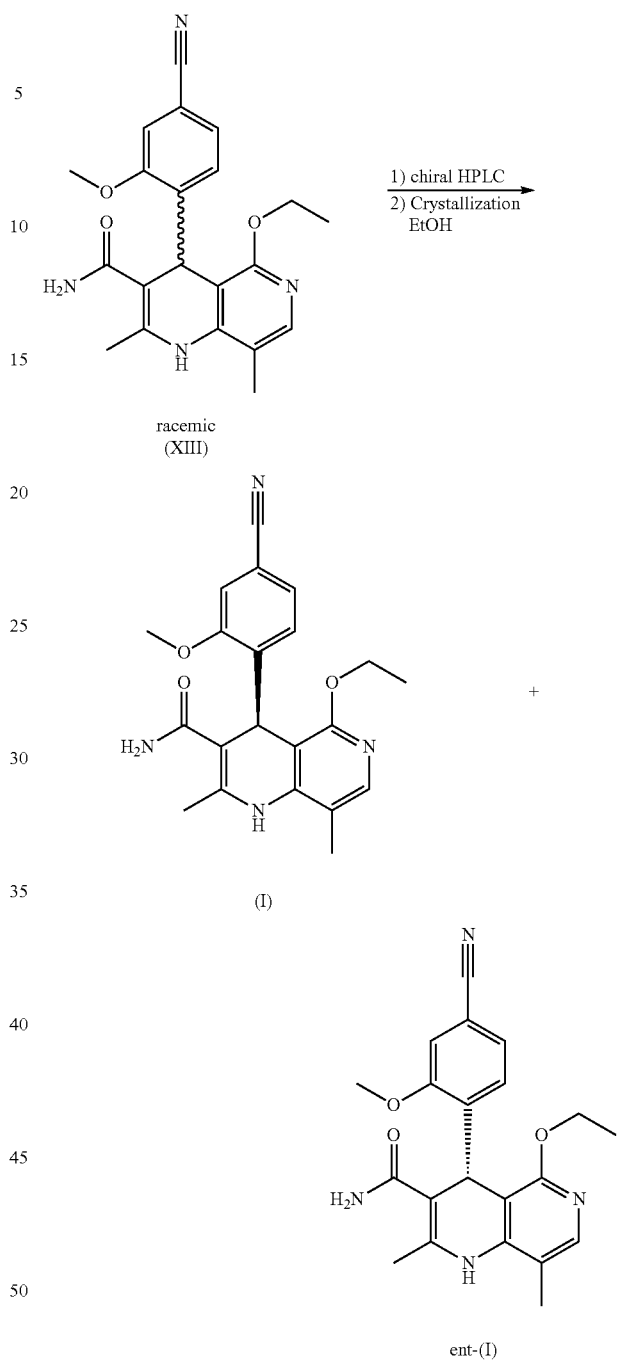

As well as the target compound of formula (I), the enantiomeric compound of the formula ent-(I) is also obtained in virtually the same yield. For economic reasons, there was a need not to destroy this enantiomer of the formula ent-(I), but to invent a process which enables conversion of the compound of the formula ent-(I) to a racemic mixture of the formula (XIII), in order to subject it to another enantiomer separation by means of SMB.

This object was achieved through use of the indirect electrochemical process according to the invention for oxidizing 1,4-dihydropyridine derivatives of the formula (A) to pyridine analogues of the formula (B)

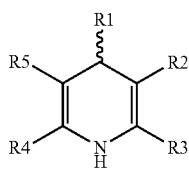

A

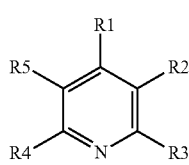

B and subsequent reduction.

For synthesis of active pharmaceutical ingredients, the oxidation of 1,4-dihydropyridine derivatives, as described in formula (A), to pyridine analogues (B)

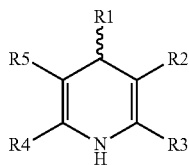

A

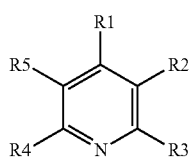

B where

R1-R5 are each independently hydrogen, fluorine, chlorine, bromine, iodine, carboxyl, carboxylic ester, hydroxyl, hydroxy ether, cyano, nitro, substituted and unsubstituted amide, ($C_1$-$C_6$)-alkyl, halo($C_1$-$C_6$)-alkyl, formyl, substituted and unsubstituted phenyl, substituted and unsubstituted benzyl, substituted and unsubstituted naphthyl, substituted and unsubstituted 5- or 6-membered heterocycle having at least one heteroatom selected from the group of N, S, O, benzofused 5- or 6-membered heterocycle, by use of chemical oxidizing agents.

Han et al. [Org. Lett. 2014, 16, 4142-4145] describe a step of oxidizing a 1,4-dihydropyridine derivative (C) [4-(3,6-dihydro-2H-pyran-4-yl)-7,7-dimethyl-5-oxo-2-(propan-2-yl)-1,4,5,6,7,8-hexahydroquinoline-3-carboxylic acid methyl ester] using 1.2 equivalents of DDQ [2,3-dichloro-5,6-dicyano-1,4-benzoquinone]. This affords an isolated yield of the pyridine derivative (D) [4-(3,6-dihydro-2H-pyran-4-yl)-7,7-dimethyl-5-oxo-2-(propan-2-yl)-5,6,7,8-tetrahydroquinoline-3-carboxylic acid methyl ester] of 93.5% by weight.

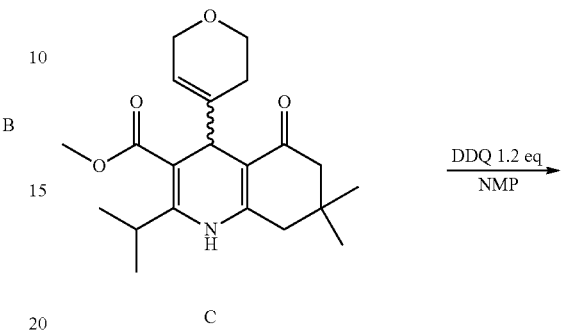

C

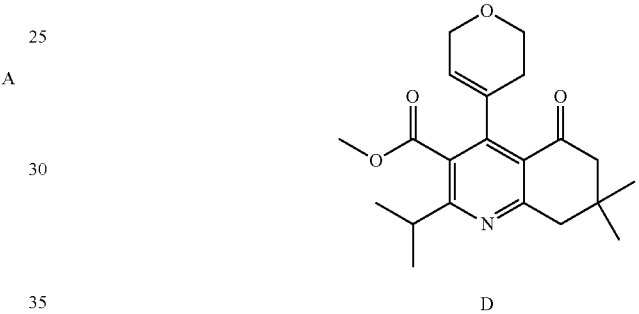

D

A disadvantage of this process is the large amount of oxidizing agent (DDQ) which is required for abstraction of two protons and two electrons from the substrate. In the best case, stoichiometric amounts of chemical oxidizing agents are required to complete the reaction. In most cases, an excess of chemical reagents is used to assure full conversion and maximum yield. Thus, an amount of waste is obtained and, moreover, the use of large amounts of oxidizing agents also increases the production costs.

In analogy to the study by Han et al., it can be assumed that this method applies to all 1,4-dihydropyridine (DHP) derivatives of the formula A and the corresponding pyridines (PYR) of the formula (B).

A corresponding application of the above-described oxidation process is a novel process for preparing (4S)-4-(4-cyano-2-methoxyphenyl)-5-ethoxy-2,8-dimethyl-1,4-dihydro-1,6-naphthyridine-3-carboxamide (I) by a recycling process from the enantiomer of the formula ent-(I) which is obtained in the process for preparing compound (I).

This is possible by first oxidizing (aromatizing) the incorrect enantiomer of the formula ent-(I) to the pyridine of the formula (XVII) and then subjecting it to electrochemical reduction:

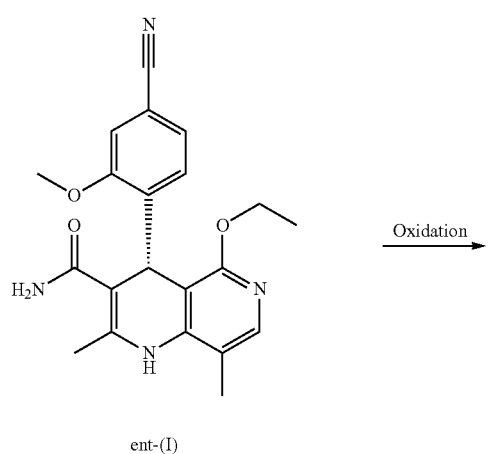

ent-(I)

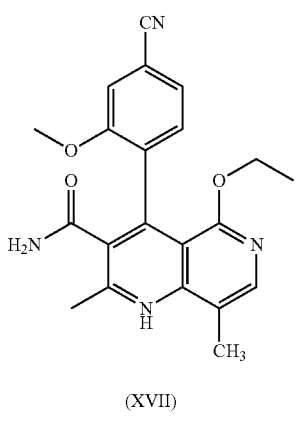

(XVII)

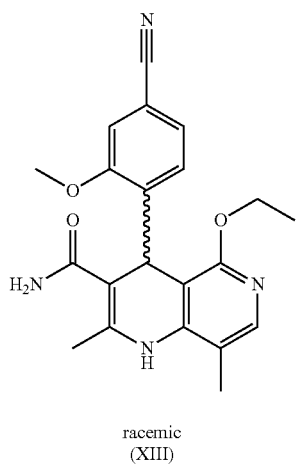

racemic
(XIII)

The description which follows elucidates the novel inventive process:

In the first step, the compound of the formula ent-(I) is oxidized (aromatized):

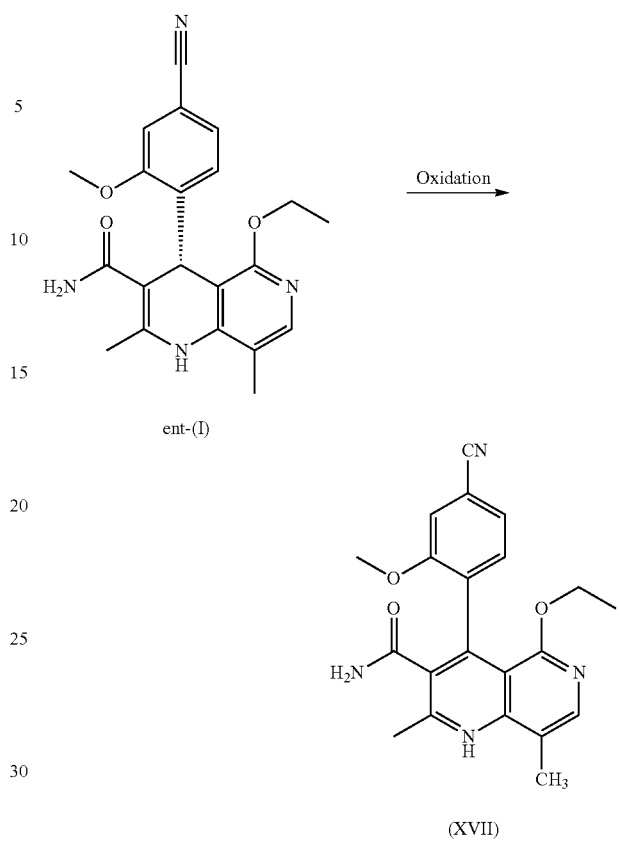

Oxidizing agents used may be the oxidizing agents that are familiar to the person skilled in the art for aromatization of piperidines and dihydropyridines; these are described, by way of example, in the book: Pyridines: From Lab to Production; edited by Eric F. V. Scriven, Elsevier Verlag 2013, Chapter 8, pages 116-144. Examples mentioned include DDQ in dichloromethane, chloranil in dichloromethane, manganese dioxide in dichloromethane, potassium permanganate in acetone, manganese(III) acetate in glacial acetic acid, cerium ammonium acetate in acetonitrile, pyridinium chlorochromate in dichloromethane, concentrated nitric acid in dichloromethane, iodine in methanol. Particular preference is given to DDQ or concentrated nitric acid in dichloromethane. The yields are generally very high, in general >86% of theory.

Earlier studies (A. Straub, Tetrahedron Asymmetry 12 (2001) 341-345) gave pointers that the oxidized dihydropyridines, i.e. the pyridyl aryls, exhibit hindered rotatability. The rotation barrier is so high that the antipodes can be separated at room temperature (axial chirality 4 atropisomerism). Therefore, proceeding from the racemates, preparative chiral chromatography methods were developed in order to separate these into the antipodes. This was surprisingly possible in the present case too.

| Separation of the racemic compound of the formula (XVII) | |
|---|---|
| Chiral stationary phase | Eluent |
| Chiralpak AS-H (250 × 4 mm) | i-hexane:ethanol = 50:50 |

The two atropisomers that occur are also the main metabolites (compounds of the formulae M1a(S) and M1b (R)) that are observed in vivo after administration of the compound of the formula (I). It was possible to determine the absolute configuration thereof by x-ray crystal structure analysis (see examples section).

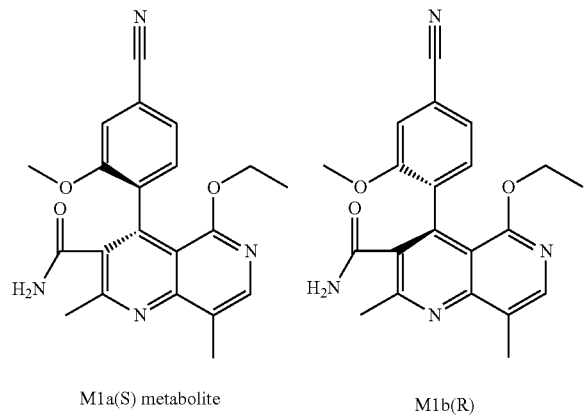

M1a(S) metabolite    M1b(R)

What is surprising is the fact that the optically active title compound of the formula (I) with the S configuration is metabolized mainly to M1a(S) in rodents and mammals, and also in humans (dog, rat, mouse, human). If the R enantiomer of the formula ent-(I) is offered ent-I mainly the metabolite of the formula M1b(R) is formed.

If, for example, an oxidation with chemical oxidizing agents is conducted, what is formed is predominantly the metabolite of the other series; title compound of the formula (I) (S configuration) gives rise predominantly to the compound of the formula M1b(R); the compound of the formula ent-(I) (R configuration) gives rise predominantly to the compound of the formula M1a(S).

If the optically active compound of the formula ent-(I) is reacted with various oxidizing agents that are familiar to the person skilled in the art, the following results are obtained:

If no solvent is specified, dichloromethane was the standard solvent used. The ratio was measured by means of a chiral HPLC method; M1a(S)/M1b(R) was normalized to 100%. The yield was measured as the conversion by means of HPLC (achiral method).

| Oxidizing agent | M1b(R) metabolite | M1a(S) metabolite | Yield/% (M1a(S) + M1b(R)) HPLC | Reaction time (h) |
|---|---|---|---|---|
| TEMPO* BF$_4$ | 7.3% | 92.7% | 77 | 1 |
| DDQ, rt | 10.1% | 89.9% | 96 | 0.5 |
| DDQ, 0° C. | 10.3% | 89.7% | 97 | 4 |
| DDQ, −20° C. | 10.7% | 89.3% | 97 | 4 |
| Chloranil | 14.3% | 85.7% | 98 | 68 |
| NHPT, Co(II) cat. (MeCN) | 37.5% | 62.5% | 90 | 18 |
| MnO$_2$, 10x | 19.0% | 81.0% | 92 | 23 |
| KMnO$_4$ (Aceton) | 8.2% | 91.2% | 89 | 19 |
| KMnO$_4$ (AcOH) | 23.6% | 76.4% | 75 | 18 |
| RuCl$_3$ (AcOH) | 11.8% | 88.2% | 42 | 72 |
| Mn(III)OAc (AcOH) | 17.8% | 82.2% | 98 | 17 |
| CAN | 42.5% | 57.5% | 90 | 18 |
| CAN (MeCN) | 13.5% | 86.5% | 96 | 64 |
| Bi(NO$_3$)$_4$ | 47.2% | 52.8% | 84 | 18 |
| PCC | 20.0% | 80.0% | 97 | 40 |
| I$_2$ (MeOH) | 20.7% | 79.3% | 77 | 18 |
| HNO$_3$ (conc) | 25.5% | 74.5% | 97 | 95 |
| A/NaIO$_4$, rt | 40.0% | 60.0% | 48 | 48 |
| A/NBu$_4$IO$_4$, rt | 42.6% | 57.4% | 80 | 24 |
| A/NBu$_4$IO$_4$, 0° C. | 49.2% | 50.8% | 80 | 18 |
| A/NBu$_4$IO$_4$, −10 | 52.2% | 47.8% | 82 | 55 |

The reagents used are shown in the following table:

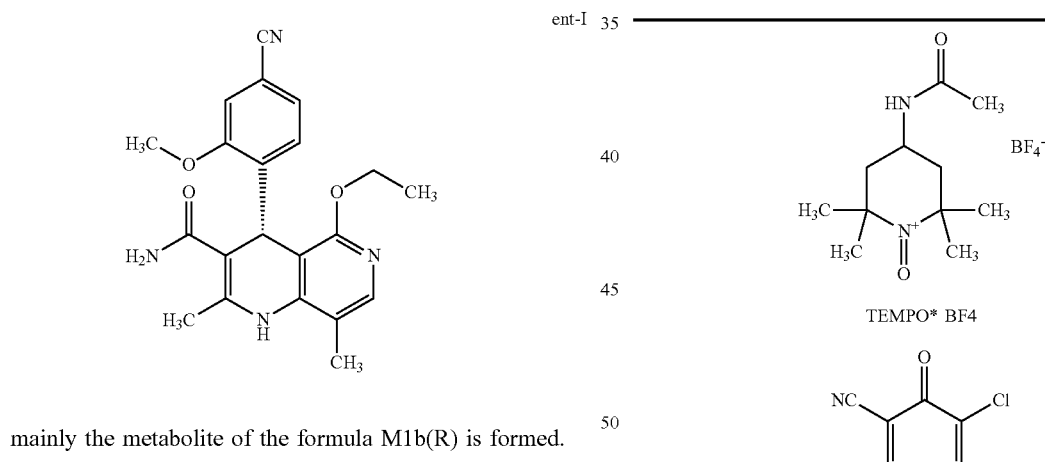

TEMPO* BF4

DDQ

Chloranil

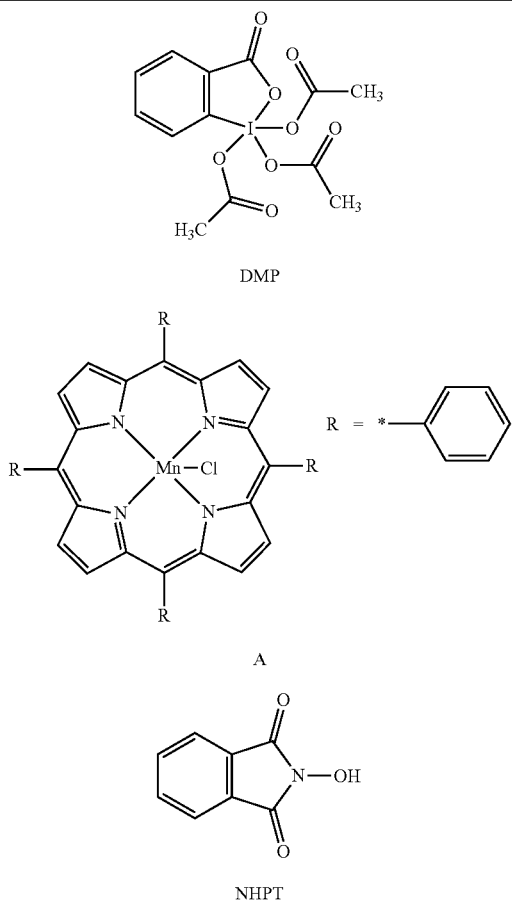

DMP

A

NHPT

It has been shown that the individual antipodes can also be thermally racemized; for this purpose, the mixture is heated in a solvent with an elevated boiling point >70° C., but it is also possible to work in a low boiling solvent, but it is then necessary to work under pressure. Useful solvents include all standard solvents such as ethanol, methanol, propanol, isopropanol, THF, dioxane, methylene chloride (under pressure), DMF, DMA, NMP, ethyl acetate, 2-Me-THF. Preference is given to working in 1-butanol and ethanol.

Mention is made by way of example of thermal racemization in 1-butanol (dissolved in about 20 times the amount). For this purpose, the enantiomeric excess e.e. % of the compound of the formula M1a(S) was determined at 3 different temperatures (see FIG. 1). It is apparent that complete racemization occurs at 105° C. within 1 h. The racemization rate can be accelerated by addition of acid (catalytic amounts of methane sulphonic acid in 1-butanol) (see FIG. 2).

The addition of a catalytic amount of acid allows the thermal racemization to be conducted at lower temperatures as well. Useful acids include methanesulphonic acid, sulphuric acid, hydrochloric acid, p-toluenesulphonic acid, and most aromatic sulphonic acids. However, preference is given to using the sulphonic acids, more preferably methanesulphonic acid.

A great disadvantage of the oxidation methods cited above is that stoichiometric or superstoichiometric amounts of oxidizing agents have to be used, and a large amount of waste is produced in this way. There was therefore a desire to keep the amount of oxidizing agent waste as small as possible. This is achieved by the present invention. The use of catalytic amounts of DDQ reduces the amount of waste significantly to a minimum, which constitutes a considerable advantage of the novel inventive process.

The best alternative to chemical oxidation would be electrochemical oxidation with replacement of chemical oxidizing agents by electrons. The use of electrochemistry makes it possible to finely adjust the oxidation potential and to dispense with the use of chemical reagents. Arguello et al. [Electrochemica Acta 49 (2004) p. 4849-4856] and Lopez-Alarcon et al. [Electrochimica Acta 48 (2003) p. 2505-2516] describe the oxidation of Hantzsch 1,4-dihydropyridines by means of voltammetry in protic and aprotic media. However, they reported high oxidation potentials that varied between +915 mV and +1093 mV versus an Ag/AgCl reference electrode in aprotic medium. At this high oxidation potential, it is well known that there is occurrence of oxidations of functional groups, e.g. amino groups or phenol groups [a) Handbook of Electrochemistry, Elsevier, editor: C. G. Zoski, 2007; b) Fundamentals and Applications of Organic Electrochemistry; Fuchigami et al., 2015 John Wiley & Sons, Ltd; c) David et al., Tetrahedron 51 (1995) 3181-3196]. Thus, the direct electrochemical oxidation of dihydropyridine derivatives is only of restricted applicability.

As an alternative to direct electrochemical oxidation, Francke and Little describe the use of indirect electrochemical reactions using various types of mediators in general [Chem. Soc. Rev. 43(8) 2014 p. 2492-2521]. No examples are cited in which it was possible to successfully oxidize dihydropyridines to their pyridine analogues. The use of DDQ in indirect electrochemical synthesis is mentioned, but has not yet been fully researched according to the authors' commentary. Examples are restricted to benzylic oxidation, i.e. side chain functionalization in aqueous acetic acid. In the case of use of dry aprotic solvents, the reaction did not proceed successfully.

One problem addressed by the invention was that of developing a process for oxidizing dihydropyridines (A) to the pyridine analogue (B)

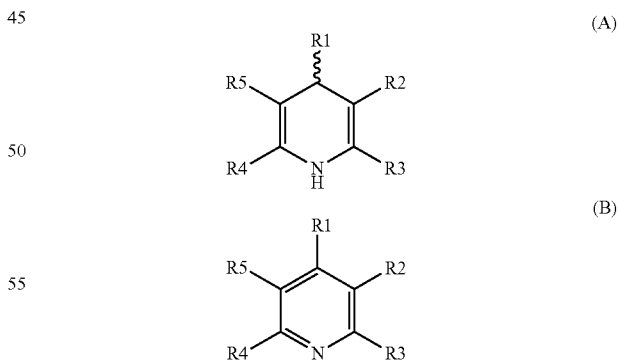

where

R1-R5 are each independently hydrogen, fluorine, chlorine, bromine, iodine, carboxyl, carboxylic ester, hydroxyl, hydroxy ether, cyano, nitro, substituted and unsubstituted amide, $(C_1-C_6)$-alkyl, halo$(C_1-C_6)$-alkyl, formyl, substituted and unsubstituted phenyl, substituted and unsubstituted benzyl, substituted and unsubstituted naphthyl, substituted and unsubstituted 5- or 6-membered heterocycle having at least one heteroatom selected from the group of N, S, O, benzo-fused 5- or 6-membered heterocycle,
characterized in that
i) substoichiometric oxidation reagents are used and the process
ii) is tolerable for side chains and a number of substituents under mild conditions.

To solve this problem, it has been found that, surprisingly, dihydropyridine derivatives can be oxidized successfully in high yields to their pyridine analogues using indirect electrochemical oxidation with substoichiometric amounts of mediators.

Optimal reaction conditions for the process according to the invention are the temperature of 1-100° C., preferably 10-50° C., more preferably 20-30° C., at standard pressure and oxidation potentials of −0.1 V to +0.6 V versus Ag/Ag+ reference electrode (10 mmol/l), preferably 0.0 V to +0.5 V and more preferably 0.1 V to 0.4 V versus Ag/Ag+ reference electrode (10 mmol/l) (measured in aprotic organic solvents).

Under very mild conditions, i.e. room temperature (25° C.) and standard pressure and small oxidation potentials (+0.4 V versus Ag/Ag+10 mmol/l) compared to direct electrochemical oxidation (>+1 V versus Ag/Ag+10 mmol/1), high yields of pyridine derivative were achieved. There were no signs of side chain oxidation, and it was possible to run the reaction in aprotic solvents as well. As far as we know, this has never been reported in literature before. The closest example from the literature is a benzylic oxidation. This was successful in aqueous acetic acid, but failed as soon as dry aprotic solvents (such as that which we used) were used. [Chem. Soc. Rev. Plant Biol., 8, 2014, p. 2492-2521).

It was possible to reduce the amount of mediator, e.g. DDQ, to less than 10 mol % (ideally about 2% with retention of a product yield >95%), and an oxidation potential of only 0.3-0.4 V versus Ag/Ag+ reference electrode was sufficient for a high conversion, a high yield and a high power efficiency.

Suitable mediators, to which the reaction is not supposed to be restricted, are: triarylamines (Ar3N type), TEMPO and other N-oxyl radicals, halide salts (HX type with X=Cl, Br, I), metal salts (Cr(VI)/Cr(III), Fe(III)/Fe(II), V(IV)/V(III), Ce(IV)/Ce(III), Co(III)Co(II), Ru(VIII)/Ru(IV), Os(VIII)/Os(VI), Mn(III)/Mn(II)), iodobenzene and iodobenzene derivatives, nitrate salts and triarylimidazole, cited in Chem. Soc. Rev. 43(8) 2014 p. 2492-2521.

For electroorganic synthesis, electrolysis apparatuses known to those skilled in the art that are called "three-electrode systems" are used [Handbook of Electrochemistry; editor: C. G. Zoski; 2007 Elsevier B. V. & Fundamentals and Applications of Organic Electrochemistry: Synthesis, Materials, Devices, First Edition, T. Fuchigami, M. Atobe and S. Inagi; 2015 John Wiley & Sons, Ltd]. In this case, three electrodes are used, named working electrode, counterelectrode and reference electrode. There are a multitude of reference electrodes, it being preferable to use the silver/silver cation (Ag/Ag+) reference electrode because of its stability and high reproducibility of measurements for non-aqueous electrolytes, i.e. organic solvents. In this case, a silver wire is immersed into a 10 mM or 0.1 M AgNO3 solution. Solvents used may be acetonitrile, dimethylformamide or dimethyl sulphoxide. The standard conductive salt used is tetrabutylammonium perchlorate (BuN4ClO4). Alternatively, however, it is also possible to use other conductive salts: Et4NBF4, Bu4NBF4, Bu4NPF6, Bu4NX (with X=I, Br) or perchlorates (NaClO4, LiClO4, Et4NClO4).

A spatial separation between working electrode and counterelectrode, i.e. between the two "half-cells", is advantageous in most cases, in order to prevent both reactants and the target product to be produced from getting to the counterelectrode and triggering unwanted side reactions there, which would result in yield losses.

For the spatial separation of working electrode and counterelectrode, separators are used, which, by virtue of a limited porosity and/or else by virtue of their chemical structure or functionality, prevent free exchange between the two half-cells. Known separators are sintered glass frits, PTFE filter membranes, cation exchange membranes, polyvinylidene fluoride or polypropylene filter membranes, and materials which are not listed hereinafter and which are stable to organic solvents and which have pore sizes small enough to restrict or entirely prevent passage of reactant and product into the other half-cell.

For the electrochemical oxidation of dihydropyridine (A), the working electrode is connected as the anode and the counterelectrode as the cathode. At the cathode, evolution of hydrogen is expected and observed.

Known electrode materials are platinum, palladium, gold, graphite, glassy carbon, boron-doped diamond, zinc, copper, nickel, tin, samarium, steel, mercury, lead or alloys consisting of copper, tin and lead, called lead bronzes. Also known to those skilled in the art are further metal and metal oxide electrodes which are also used in doped form or in alloys: Ru/RuO2, Ti/TiO2, RuO2/TiO2, Ir/IrO2, Pt/Ti, platinum/iridium.

More particularly, cathodic formation of gaseous hydrogen is known to those skilled in the art as a competing reaction. Therefore, preference is given to cathode materials having a high overvoltage with respect to hydrogen formation. Thus, the overvoltage for $H_2$ formation increases in the following sequence: Pd<Au<Pt<Ni<Cu<Sn<Pb<Zn<Hg.

Typical solvents which have also been described for electroorganic syntheses are acetonitrile, ethanol, tetrahydrofuran (THF), acetone, N,N-dimethylformamide (DMF), methanol, dichloromethane, dimethyl sulphoxide (DMSO), hexamethylphosphoramide ([(CH3)2N]3PO; CAS: 680-31-9). Solvents that are common knowledge to the person skilled in the art are also NMP, N,N-dimethylacetamide, propanol, isopropanol, methylene chloride, ethyl acetate.

Conductive salts which are added to organic solvents to increase the conductivity are: Et4NBF4, Bu4NBF4, Bu4NPF6, Bu4NX (with X=I, Br) or perchlorates (NaClO4, LiClO4, Et4NClO4, Bu4NClO4).

The widespread "three-electrode systems" that have been described in detail are generally employed in the beaker glass cells, H cells or other containers that are known to those skilled in the art. By means of magnetic stirrers, it is possible to continuously stir the reaction mixtures. The majority of experiments are batch experiments in which the solvent/conductive salt mixture is initially charged in both half-cells. The reactant is introduced only into the half-cell in which it is also to be electrochemically converted.

By continuous circulation of the reaction mixture by means of circulation pumps, it is also possible to operate such cells as flow cells. In addition, the literature describes very specific geometries for flow cells [Handbook of Electrochemistry; editor: C. G. Zoski; 2007 Elsevier B. V. & Fundamentals and Applications of Organic Electrochemistry: Synthesis, Materials, Devices, First Edition, T. Fuchigami, M. Atobe and S. Inagi; 2015 John Wiley & Sons, Ltd]. See FIG. 3. Particular preference is given to flow cells in the filter press design with a view to scale-up of the synthesis. Proceeding from very small cross-sectional areas (10 cm2), scale-up can be achieved firstly by increasing the cross-sectional area to up to 0.4 m² per module (commercially available from Electrocell, model MFC up to 0.001 m², model MPC from 0.01 to 0.2 m², model ESC from 0.04 to 1.04 m², model EPC from 0.4 to 16.0 m²), and secondly by numbering-up, i.e. the coupling of several identical modules in one stack. The risk of such a scale-up process is manageable, since there is no need to change the other geometric dimensions, for example the electrode separation, the electrode material (for anode and cathode) and also the operating parameters (especially the current density).

By means of a regulatable flow rate, it is possible to control the residence time in the cell. Typical residence times are in the range of 0.1-100 s per single pass. For the process according to the invention, with employment of flow cells in the electrochemical reduction, residence times are preferably 0.5-50 s, and particular preference is given to residence times per single pass of 1-10 s.

The selection of the current density depends both on the residence time and on the kinetics of the target reaction, and also on unwanted side reactions. Too high a current density with simultaneously long residence time and gas formation (e.g. $H_2$) would lead to shielding of the electrode area as a result of the formation of a gas cushion in the cell. For the electrochemical oxidation of (XIII) to (XVII) with DDQ as mediator, current densities of 1-100 mA/cm² are conceivable. Preference is given, however, to current densities in the range of 5-50 mA/cm² and more preferably in the range of 10-30 mA/cm², in order to achieve maximum selectivity with sufficient space-time yield. The use of different solvents from the above list is possible in principle. Preferred solvents are DMF, DMA, NMP, acetonitrile and mixtures thereof.

For performance of the process according to the invention in the case of compound ent-(I), the following procedure has been found to be useful:

The oxidation of compound ent-(I) to the corresponding derivative (XVII) with DDQ as mediator proceeds according to the scheme which follows in FIG. 4, i.e. ent-(I)→(XVII)+ $H_2$, with application of voltage and electrical current (see FIG. 4).

For examination and for better understanding of the system, cyclic voltammetry was conducted in an undivided beaker-type cell with a diameter of 5 cm with a Pt cage electrode (working electrode) on the outside and a Pt wire electrode (counterelectrode) in the middle. Arranged close to the working electrode was an Ag/Ag⁺ reference electrode (10 mmol/l in acetonitrile). The cell was filled with 100 ml of acetonitrile in which 2.17 g (10 mmol) of tetraethylammonium tetrafluoroborate (Et4NBF4) were dissolved together with 22.7 mg (0.1 mmol) of DDQ and 378.4 mg (1 mmol) of the compound of the formula ent-(I). For the cyclic voltammetry traces without the compound of the formula ent-(I) or without DDQ, the appropriate amount was not added. Cyclic voltammetry traces were recorded using a potentiostat of the Gamry Interface 1000 design with a scan rate of 250 mV/s and 100 mV/s over 10 cycles between –0.5 and +1 V versus reference electrode. After excluding the first and last cycles, the result was averaged. Cyclic voltammetry is known to the person skilled in the art as a means of studying electrochemical reactions at the electrode surface.

The results of the cyclic voltammetry tests are reported in FIG. 5. It is clear that, in the case of DDQ without the substrate ent-(I)—dotted line—2 peaks are clearly apparent. A reduction peak (negative) at about +0.1 V versus Ag/Ag⁺, which is associated with the reaction DDQ→$H_2$DDQ, and an oxidation peak (positive) at about +0.3 V versus Ag/Ag⁺, which is associated with the reaction $H_2$DDQ→DDQ.

Moreover, the cyclic voltammogram is entirely symmetrical, which means that the reactions are entirely reversible.

On consideration of the cyclic voltammogram of the substrate ent-(I) without DDQ (dashed line), i.e. in direct oxidation mode, it is apparent that ent-(I) can only be oxidized above 0.6 V versus Ag/Ag⁺ and at least 1 V is required to obtain an acceptable conversion (see FIG. 5). After electrolysis at +1.0 V versus Ag/Ag for 1 h, discolouration of the solution and the presence of several secondary components in the HPLC were noted. Exact identification and quantitative determination was not possible. This was to be expected, since the literature [a) Handbook of Electrochemistry, Elsevier, editor: C. G. Zoski, 2007; b) Fundamentals and Applications of organic Electrochemistry; Fuchigami et al., 2015 John Wiley & Sons, Ltd.] discloses that amines and amides (which are present in the molecule, for example) can be oxidized between +0.5 and +1.0 V versus SCE (Handbook of Electrochemistry, page 819).

On comparison with mediated electrolysis, i.e. substrate+ 10 mol % of DDQ (solid line), the formation of a very effective charge transfer complex is apparent, the substrate being oxidizable at the same potential by DDQ (about 0.3 V) and the process being very effective and hence exhibiting the highest current. Moreover, it is apparent that the reverse reaction (reduction peak) has completely disappeared, since DDQ can now only react with the substrate and is no longer available to the electrode.

It should be pointed out that, after leaving the system to react at the potential of +0.4 V versus Ag/Ag⁺ over a period of 2 h, a conversion of the substrate of about 98% has been achieved and no secondary components have been observed, but only the desired component. See also examples. This is comparable to the direct conversion, in which only a low selectivity was attained.

Thus, it is possible to define an ideal operating window (potential between 0.3 and 0.5 V) in which the regeneration of DDQ (i.e. the oxidation $H_2$DDQ→DDQ) is at a maximum (>0.3 V) and the direct unselective reaction of the substrate with the electrode (<0.5 V) is completely avoided. This is the ideal operating window that allows the maximum yield and selectivity.

It should also be pointed out that, under such conditions (i.e. with +0.4 V versus Ag/Ag⁺ as reference), it was possible to achieve a high current of 65 mA and hence a high reaction rate of 1.2 mmol/h. To obtain the same rate in a non-mediated direct electrochemical system, a voltage of +1.0 V is to be applied, which will damage the molecule.

In analogy to the cyclic voltammetry, in the same batch cell with the same solution and configuration, a production test is conducted. In this test, the solution was electrolysed at a constant potential of +0.4 V for 2 hours and a sample was taken every 15 minutes and analysed by means of HPLC. After the 2 hours had elapsed, the conversion surprisingly reached 98%, the product yield was >97.5% (selectivity >99%), and, even more surprisingly, a charge of only 2.1 F had flowed. In view of the fact that the stoichiometric (minimum) amount of power required is 2 F, the power efficiency exceeded 95%. If a low power efficiency is not a sign of an unselective reaction, selective reactions are a necessary condition for high power efficiencies. From this, it is clearly apparent, together with the HPLC analysis, that the mediated oxidation of (I) to (XVII), or more generally of (A) to (B), is a much more favourable process in terms of selectivity and yield than chemical and direct electrochemical oxidation (see FIG. 6).

The compound (XIII) exists in 2 enantiomeric forms: (I) and ent-(I). The product (XVII) exists in 2 forms having axial chirality, which are known as M1a(S) and M1b(R). It has been found that, surprisingly, by conversion by means of mediated electrochemical reduction according to the above description, the compound of the formula (I) is preferentially converted to M1b(R), where the M1a(S):M1b(R) ratio is 13:87 (Example 27), and ent-(I) is preferentially converted to M1a(S), where the M1a(S):M1b(R) ratio is 90:10 (Example 26). These results are comparable to the result obtained by chemical oxidation with stoichiometric amounts of DDQ (Examples 11a and 11b). Surprisingly, the compound of the formula (I) is preferentially metabolized in animal cells (including human cells) to the compound of the formula M1a(S), but the compound of the formula ent-(I) to the compound of the formula M1b(R).

In the case of use of a racemic mixture of the compound of the formula (I), i.e. the compound of the formula (XIII), the electrochemical oxidation leads as expected to a racemic mixture of (XVII) with an M1a(S):M1b(R) ratio of 50:50 (Example 28).

In view of the high selectivity and power efficiency observed, it would also be possible to conduct the above procedure without any particular difficulties in flow cells of the type described above (for example from Electrocell). This allows a higher space-time yield and greater production on the industrial scale.

Isolation of (XVII): After the electrochemical conversion has been effected (reactant (I) generally <1%), the reaction solution is worked up. The conversion proceeds in high yields (>98%) and surprisingly cleanly with virtually no impurities. It has been found to be advantageous that the solvent is first substantially distilled off and then the product is precipitated by a water precipitation (addition of water), filtered off and dried. The product thus obtained can be recrystallized from ethanol or isopropanol or 1-butanol, or 2-butanol.

In the next step, an electrochemical reduction of the pyridine of the formula (XVII) to the dihydropyridine is conducted:

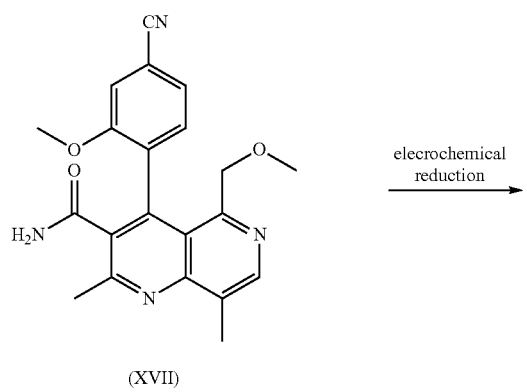

(XVII)

elecrochemical reduction

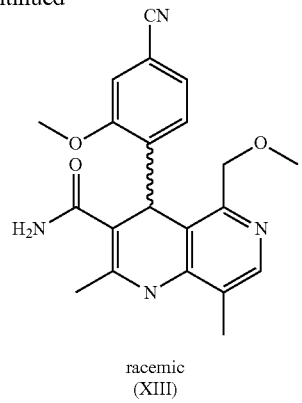

racemic
(XIII)

State of the Art for (Electro)Chemical Reduction of Pyridines

Straub and Goehrt [Alexander Straub and Axel Goehrt, Angew. Chem., 108 (1996), 2832-2834 (title: Inversion of Optically Active Dihydropyridines by Oxidation and Electroreduction)] describe the electrochemical reduction of pyridine derivatives which are all characterized, inter alia, by the presence of an ester group (—CO2Et), at mercury electrodes. The pyridines used by Kita et al. [Yoshio Kita, Hirofumi Maekawa, Yasuhiro Yamasaki and Ikuzo Nishiguchi, Tetrahedron Letters 40 (1999) 8587-8590 (title: Selective and facile electroreductive synthesis of dihydro- and tetrahydropyridine dicarboxylic acid derivatives); Yoshio Kita, Hirofumi Maekawa, Yasuhiro Yamasaki and Ikuzo Nishiguchi, Tetrahedron 57 (2001) 2095-2102 (title: Highly selective and facile synthesis of dihydro- and tetrahydropyridine dicarboxylic acid derivatives using electroreduction as a key step)] also actually have two ester substituents (—CO2Me). Straub and Goehrt report an 83% yield for a very small laboratory batch of 0.72 mmol of pyridine derivative.

Kita et al. describe both 1,2- and 1,4-dihydropyridine as products. Experiments on C and Pb electrodes gave 0% yield. On Pt cathodes, yields of 36% were achieved. Only in the case of use of ammonium chloride and temperatures well below room temperature (5-10° C.) was it possible to achieve yields exceeding 83% on Pt cathodes.

Eisner and Kuthan [Ulli Eisner and Josef Kuthan, Chem. Rev. (1972), 72, 1-42 (title: The Chemistry of Dihydropyridines)] describe the chemical reduction of pyridines by means of NaBH4 or by catalytic hydrogenation. In both cases, there are yield losses as a result of unselective reduction of substituents (for example of the ester group to the alcohol) or as a result of reduction of the nitrile group. In addition, 1,2-dihydropyridines were observed as main products here too.

The prior art thus does not disclose any general method of selective reduction of pyridine derivatives, especially not of pyridine derivatives that do not have any methyl ester or ethyl ester substituents. Mercury electrodes are additionally unsuitable for the synthesis of active pharmaceutical ingredients because of their toxic character. Moreover, the formation of 1,2-dihydropyridine derivatives as described in the prior art is to be avoided, since this too gives rise to yield losses.

The description which follows elucidates the second step of the inventive process, the electrochemical reduction of the pyridine (XVII) to the amide (XIII):

For electroorganic synthesis, electrolysis apparatuses known to those skilled in the art that are called "three-electrode systems" are used [Handbook of Electrochemistry; edited by C. G. Zoski; 2007 Elsevier B. V. & Fundamentals and Applications of Organic Electrochemistry: Synthesis, Materials, Devices, First Edition, T. Fuchigami, M. Atobe and S. Inagi; 2015 John Wiley & Sons, Ltd]. In this case, three electrodes are used, named working electrode, counterelectrode and reference electrode. There are a multitude of reference electrodes [Handbook of Electrochemistry; edited by C. G. Zoski; 2007 Elsevier B. V.], it being preferable to use the silver/silver cation (Ag/Ag+) reference electrode because of its stability and high reproducibility of measurements for nonaqueous electrolytes, i.e. organic solvents. In this case, a silver wire is immersed into a 10 mM or 0.1 M AgNO3 solution. Solvents used may be acetonitrile, dimethylformamide or dimethyl sulphoxide. The standard conductive salt used is tetrabutylammonium perchlorate (BuN4ClO4). Alternatively, however, it is also possible to use other conductive salts: Et4NBF4, Bu4NBF4, Bu4NPF6, Bu4NX (with X=I, Br) or perchlorates (NaClO4, LiClO4, Et4NClO4).

A spatial separation between working electrode and counterelectrode, i.e. between the two "half-cells", is advantageous in most cases, in order to prevent both reactants and the target product to be produced from getting to the counterelectrode and triggering unwanted side reactions there, which would result in yield losses.

For the spatial separation of working electrode and counterelectrode, separators are used, which, by virtue of a limited porosity and/or else by virtue of their chemical structure or functionality, prevent free exchange between the two half-cells. Known separators are sintered glass frits, PTFE filter membranes, cation exchange membranes, polyvinylidene fluoride or polypropylene filter membranes, and materials which are not listed hereinafter and which are stable to organic solvents and which have pore sizes small enough to restrict or entirely prevent passage of reactant and product into the other half-cell.

For the electrochemical reduction of the pyridine (XVII), the working electrode is connected as the cathode and the counterelectrode as the anode.

Known electrode materials are platinum, palladium, gold, graphite, glassy carbon, boron-doped diamond, zinc, copper, nickel, tin, samarium, steel, mercury, lead or alloys consisting of copper, tin and lead, called lead bronzes. Also known to those skilled in the art are further metal and metal oxide electrodes which are also used in doped form or in alloys: Ru/RuO2, Ti/TiO2, RuO2/TiO2, Ir/IrO2, Pt/Ti, platinum/iridium.

Especially in aqueous electrolytes, cathodic formation of gaseous hydrogen is known to those skilled in the art as a competing reaction. Therefore, preference is given to cathode materials having a high overvoltage with respect to hydrogen formation. Thus, the overvoltage for H2 formation increases in the following sequence: Pd<Au<Pt<Ni<Cu<Sn<Pb<Zn<Hg.

In nonaqueous electrolytes, the electrochemical stability of the solvent and conductive salt decides whether side reactions occur at the electrodes and to what extent.

What is called the electrochemical window is tabulated for selected solvent/conductive salt mixtures [Handbook of Electrochemistry; edited by C. G. Zoski; 2007 Elsevier B. V. & Fundamentals and Applications of Organic Electrochemistry: Synthesis, Materials, Devices, First Edition, T. Fuchigami, M. Atobe and S. Inagi; 2015 John Wiley & Sons, Ltd]. For example, the acetonitrile/0.1 M Bu4NPF6, tetrahydrofuran/0.1 M Bu4NPF6, acetonitrile/0.1 M Et4NBF4, DMF/0.1 M Bu4NClO4 combinations are cited, which are still considered to be electrochemically stable even at more negative potentials than −2.0 V (versus saturated calomel electrode). This does not restrict or fundamentally rule out the use of other solvents.

Typical solvents which have also been described for electroorganic syntheses are acetonitrile, ethanol, tetrahydrofuran (THF), acetone, N,N-dimethylformamide (DMF), methanol, dichloromethane, dimethyl sulphoxide (DMSO), hexamethylphosphoramide ([(CH3)2N]3PO; CAS: 680-31-9). Solvents that are common knowledge to the person skilled in the art are also NMP, N,N-dimethylacetamide, propanol, isopropanol, methylene chloride, ethyl acetate.

Conductive salts which are added to organic solvents to increase the conductivity are: Et4NBF4, Bu4NBF4, Bu4NPF6, Bu4NX (with X=I, Br) or perchlorates (NaClO4, LiClO4, Et4NClO4, Bu4NClO4).

The widespread "three-electrode systems" that have been described in detail are generally employed in the beaker glass cells, H cells or other containers that are known to those skilled in the art. By means of magnetic stirrers, it is possible to continuously stir the reaction mixtures. The majority of experiments are batch experiments in which the solvent/conductive salt mixture is initially charged in both half-cells. The reactant is introduced only into the half-cell in which it is also to be electrochemically converted.

By continuous circulation of the reaction mixture by means of circulation pumps, it is also possible to operate such cells as flow cells. In addition, the literature describes very specific geometries for flow cells [Handbook of Electrochemistry; edited by C. G. Zoski; 2007 Elsevier B. V.]. Particular preference is given to flow cells in the filter press design with a view to scale-up of the synthesis. Proceeding from very small cross-sectional areas (10 cm$^2$), scale-up can be achieved firstly by an increase in the cross-sectional area to up to 0.4 m$^2$ per module (as a module unit of the "Electro Prod Cell", commercially available from Electrocell), and secondly by numbering-up, i.e. the coupling of several identical modules in a stack. The risk of such a scale-up process is manageable, since there is no need to change the other geometric dimensions, for example the electrode separation, the electrode material (for anode and cathode) and also the operating parameters (especially the current density). For the process according to the invention, as well as simple beaker glass cells, flow cells such as the micro-flow cell with 10 cm$^2$ and the multipurpose cell with 100 cm$^2$ of active electrode cross-sectional area from Electrocell have been used successfully.

By means of a regulatable flow rate, it is possible to control the residence time in the cell. Typical residence times are in the range of 0.1-100 s per single pass. For the process according to the invention, with employment of flow cells in the electrochemical reduction, residence times are preferably 0.5-50 s, and particular preference is given to residence times per single pass of 1-10 s.

The selection of the current density depends both on the residence time and on the kinetics of the target reaction, and on unwanted side reactions. Too high a current density with simultaneously long residence time and gas formation (e.g. $H_2$) would lead to shielding of the electrode area as a result of the formation of a gas cushion in the cell. For the electrochemical reduction of the racemate M1, current densities of 1-100 mA/cm$^2$ are conceivable. Preference is given, however, to current densities in the range of 5-50 mA/cm$^2$ and more preferably in the range of 10-30 mA/cm$^2$, in order to achieve maximum selectivity with sufficient space-time yield, since it has been found that, surprisingly, excessively high current densities lead to unwanted side reactions and hence the yield drops.

The use of different solvents from the above list is possible in principle. Preferred solvents are methanol, DMF, DMA, NMP, acetonitrile and mixtures thereof.

It has been found that, surprisingly, the use of methanol as solvent in beaker cells enables target product yields greater than 97%. It has been found that, surprisingly, a combination of aprotic solvent and protic solvent in the flow cell showed improved power efficiencies compared to pure methanol. Conversions and yields exceeding 94% were achievable in the flow cell, with the two half-cells separated from one another by means of cation exchange membrane. The successful transfer of the electrochemical reduction of pyridine of the formula (XVII) to the amide of the formula (XIII) from the beaker cell to the flow cell enables the scalability of the process and hence economic utilization.

Particular preference is given to mixtures having an equal or greater proportion of aprotic solvents and an equal or smaller proportion of protic solvent. Aprotic solvents are common knowledge to the person skilled in the art. Preference is given especially to DMF, DMA and acetonitrile. Protic solvents are likewise common knowledge to the person skilled in the art. Preferred protic solvents are methanol, formic acid, ethanol and acetic acid. Particular preference is given to the combination of methanol and DMF. The methanol content here should be between 0.1%-50% by weight. Preference is given to a methanol content of 0.5%-25% by weight and more preferably of 1%-10% by weight. In this mixture, ethanol is preferably also present as well as methanol. Particular preference is likewise given to the combination of ethanol and DMF. The ethanol content here should be between 0.1%-50% by weight. Preference is given to an ethanol content of 0.5%-25% by weight and more preferably of 1%-10% by weight. The use of ethanol prevents a transetherification reaction in which the ethyl ether can be transetherified to the methyl ether.

The examples adduced hereinafter document that, proceeding from racemic pyridine of the formula (XVII), the target product, namely racemic amide of the formula (XIII), is obtained by electrochemical reduction and hence the process according to the invention comprising the next step (separation of the two enantiomers of the formulae (I) and ent-(I), for example in an SMB system) to give the pure target compound of the formula (I). It has additionally been found that, surprisingly, in the case of use of the pure atropisomers M1b(R) and M1a(S), the electrochemical reduction in beaker cells at platinum-iridium mesh electrodes does not lead to a racemic product of the formula (XIII). In the case of reduction of the compound of the formula M1b(R), there is preferential formation of the desired enantiomer (target product) of the formula (I) in a ratio of about 78:22 [(I):ent-(I)]. Proceeding from the atropisomer of the formula M1a(S), the incorrect enantiomer of the formula ent-(I) is obtained in excess: ratio [(I):ent-(I)]= 22:78. This observation opens up the option of further increasing the recycling yield of target product of the formula (I) per cycle (oxidation-reduction-chiral HPLC) by selective oxidation of the compound of the formula ent-(I) to the compound of the formula M1b(R).

Isolation of the Compound of the Formula (XIII):

After the electrochemical conversion has been effected (reactant of the formula (XVII) generally <1%), the reaction solution is worked up. The conversion proceeds in high yields (>98%) and surprisingly cleanly with virtually no impurities. It has been found to be advantageous that the solvent is first substantially distilled off and then the product is precipitated by a water precipitation (addition of water), filtered off and dried. The product thus obtained can be recrystallized from ethanol or THF and subjected to another enantiomer separation by means of SMB.

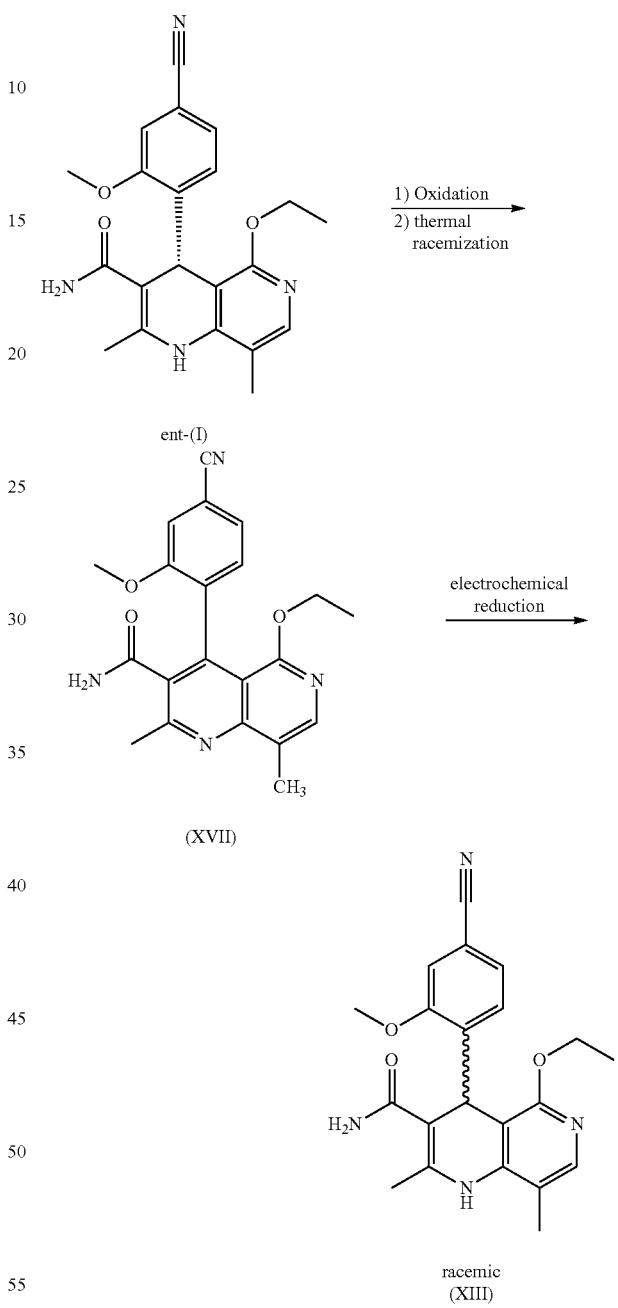

In Summary, the Process Will Proceed as Follows:

First of all, the incorrect enantiomer of the formula ent-(I) is oxidized, giving the compound of the formula M1a(S) in excess; in the course of the workup, a thermal racemization (optionally acid-catalysed) is conducted. Subsequently, the isolated racemic compound of the formula (XVII) is subjected to an electrochemical reduction. After workup, the racemic compound of the formula (XIII) is isolated and recrystallized. The product of the formula (XIII) thus obtained has a high purity and is fed into the SMB process.

The oxidation/reduction process described here can be conducted several times in succession and thus opens up the option, in production in quasi-continuous mode, of converting the incorrect enantiomer of the formula ent-(I) to the correct product of the formula (I), which offers great advantages in terms of costs. After several process cycles, almost complete neutralization of the incorrect enantiomer of the formula ent-(I) is achieved.

A particularly important advantage of the novel process for recovering the compound of the formula (XIII) is considered to be its high chemical purity. Since an active pharmaceutical ingredient is involved, all operations are conducted under GMP and require high purities of the intermediates.

With the novel synthesis, it is possible to prepare the compound of the formula (I) in a very efficient manner. The process offers considerable advantages compared to the prior art relating to scalability and technical performance. The overall yield is significantly higher compared to published data and excellent purities of the active ingredient are also achieved. The novel process enables the reproducible, economic preparation of the defined compound of the formula (I). Using the process presented here, 200 kg of material has already been successfully prepared for clinical trials.

The present invention provides a process for preparing compounds of formula (B)

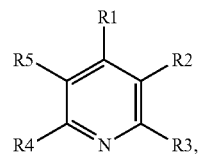

(B)

characterized in that compounds of the formula (A)

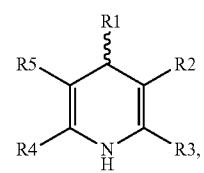

(I)

where
R1-R5 are each independently hydrogen, fluorine, chlorine, bromine, iodine, carboxyl, carboxylic ester, hydroxyl, hydroxy ether, cyano, nitro, substituted and unsubstituted amide, $(C_1-C_6)$-alkyl, halo$(C_1-C_6)$-alkyl, formyl, substituted and unsubstituted phenyl, substituted and unsubstituted benzyl, substituted and unsubstituted naphthyl, substituted and unsubstituted 5- or 6-membered heterocycle having at least one heteroatom selected from the group of N, S, O, benzofused 5- or 6-membered heterocycle,
are oxidized electrochemically via an indirect electrochemical oxidation.

The present invention further provides a process as presented above, characterized in that the indirect electrochemical oxidation is conducted at a temperature of 1-100° C. and standard pressure.

The present invention further provides a process as presented above, characterized in that the indirect electrochemical oxidation is conducted at an oxidation potential of −0.1 V to +0.6 V versus Ag/Ag$^+$ reference electrode.

The present invention further provides a process as presented above, characterized in that the indirect electrochemical oxidation is conducted using DDQ as a mediator.

The present invention further provides a process as presented above, characterized in that the indirect electrochemical oxidation is conducted at a temperature of 1-110° C. and standard pressure at an oxidation potential of −0.1 V to +0.6 V versus Ag/Ag$^+$ reference electrode and using DDQ as a mediator.

The present invention further provides a process for preparing the compound of the formula (XVII)

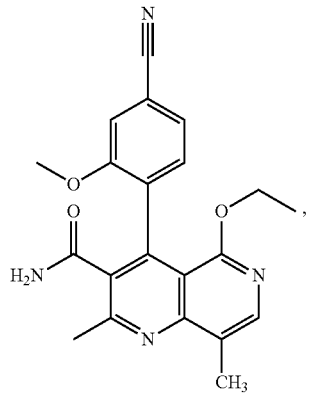

(XVII)

characterized in that compounds of the formula ent-(I)

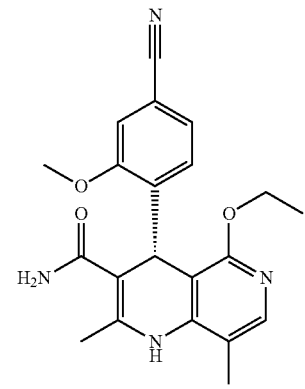

ent-(I)

are oxidized electrochemically via an indirect electrochemical oxidation.

The present invention further provides a process as presented above, characterized in that the indirect electrochemical oxidation is conducted at a temperature of 1-100° C. and standard pressure.

The present invention further provides a process as presented above, characterized in that the indirect electrochemical oxidation is conducted at an oxidation potential of −0.1 V to +0.6 V versus Ag/Ag$^+$ reference electrode.

The present invention further provides a process as presented above, characterized in that the indirect electrochemical oxidation is conducted using DDQ as a mediator.

The present invention further provides a process as presented above, characterized in that the indirect electrochemical oxidation is conducted at a temperature of 1-110° C. and standard pressure at an oxidation potential of −0.1 V to +0.6 V versus Ag/Ag⁺ reference electrode and using DDQ as a mediator.

The present invention further provides a process for preparing the compound of the formula (XVII)

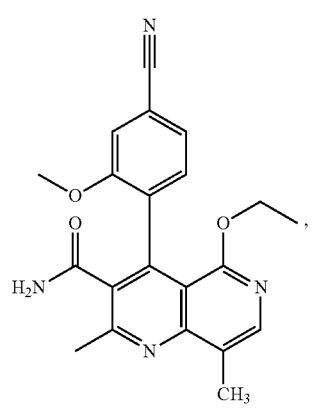

(XVII)

characterized in that compounds of the formula (XIII)

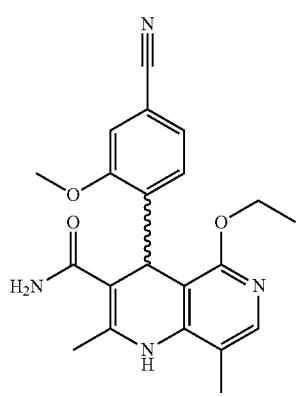

(XIII)

are oxidized electrochemically via an indirect electrochemical oxidation.

The present invention further provides a process as presented above, characterized in that the indirect electrochemical oxidation is conducted at a temperature of 1-100° C. and standard pressure.

The present invention further provides a process as presented above, characterized in that the indirect electrochemical oxidation is conducted at an oxidation potential of −0.1 V to +0.6 V versus Ag/Ag⁺ reference electrode.

The present invention further provides a process as presented above, characterized in that the indirect electrochemical oxidation is conducted using DDQ as a mediator.

The present invention further provides a process as presented above, characterized in that the indirect electrochemical oxidation is conducted at a temperature of 1-110° C. and standard pressure at an oxidation potential of −0.1 V to +0.6 V versus Ag/Ag⁺ reference electrode and using DDQ as a mediator.

The present invention further provides a process for preparing the compound of the formula (XVII)

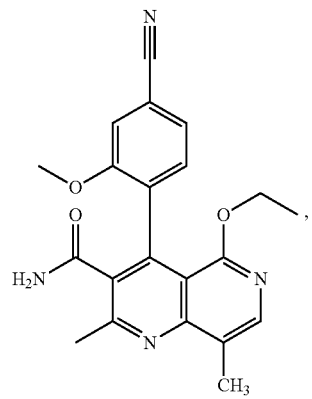

(XVII)

characterized in that compounds of the formula (I)

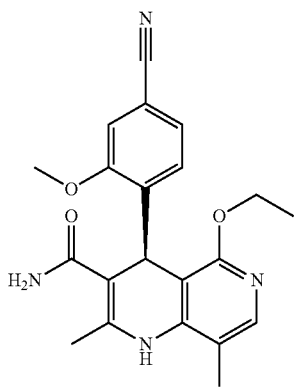

(I)

are oxidized electrochemically via an indirect electrochemical oxidation.

The present invention further provides a process as presented above, characterized in that the indirect electrochemical oxidation is conducted at a temperature of 1-100° C. and standard pressure.

The present invention further provides a process as presented above, characterized in that the indirect electrochemical oxidation is conducted at an oxidation potential of −0.1 V to +0.6 V versus Ag/Ag⁺ reference electrode.

The present invention further provides a process as presented above, characterized in that the indirect electrochemical oxidation is conducted using DDQ as a mediator.

The present invention further provides a process as presented above, characterized in that the indirect electrochemical oxidation is conducted at a temperature of 1-110° C. and standard pressure at an oxidation potential of −0.1 V to +0.6 V versus Ag/Ag⁺ reference electrode and using DDQ as a mediator.

The present invention provides a process for preparing compounds of the formulae M1a(S) and M1b(R)

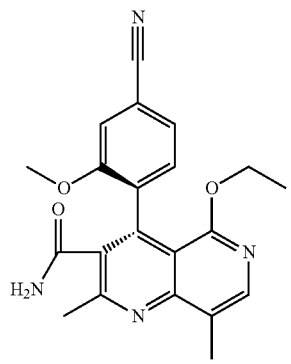

M1a(R)

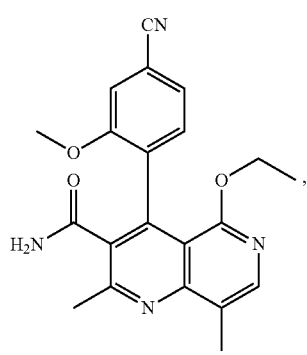

(XVII)

characterized in that a mixture of the compounds of the formulae M1a(S) and M1b(R)

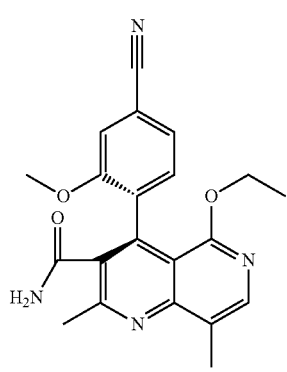

M1b(R)

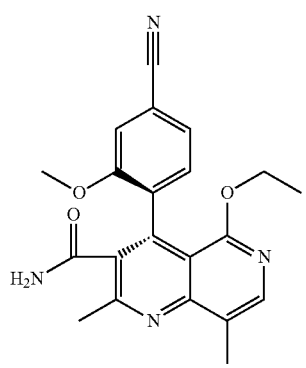

M1a(S)

characterized in that the compound of the formula ent-(I)

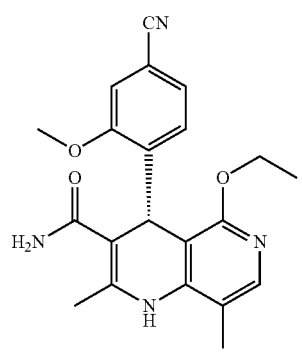

ent-(I)

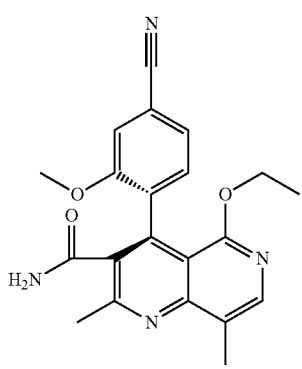

M1b(R)

is oxidized.

The present invention provides a process for preparing compounds of the formulae M1a(s) and M1b(R) as described above, characterized in that the oxidation is conducted with chemical oxidizing agents.

The present invention further provides a process for preparing the racemic compound of the formula (XVII)

is thermally racemized.

The present invention provides a process for preparing the compound of the formula (XVII) as described above, characterized in that a mixture of the compounds of the formulae M1a(S) and M1b(R) is racemized at a temperature of 70 to 110° C. with or without addition of an acid.

The present invention further provides a process for preparing the compounds of the formulae (I) and ent-(I)

(I)

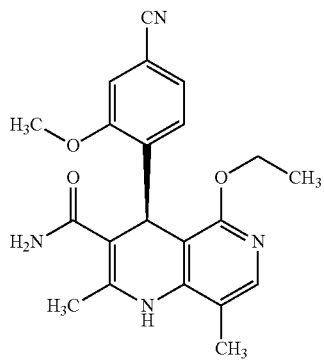

ent-(I)

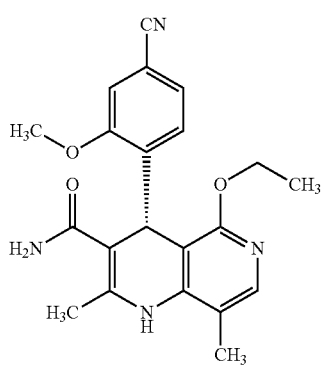

characterized in that compounds of the formulae (XVII) or M1a(S) or M1b(R) or a mixture of M1a(S) and M1b(R)

(XVII)

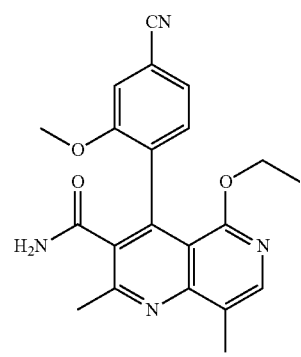

M1a(S)

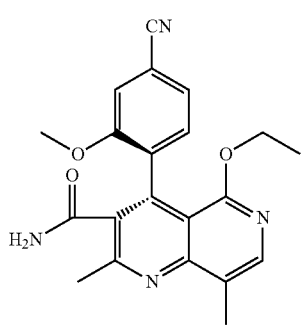

M1b(R)

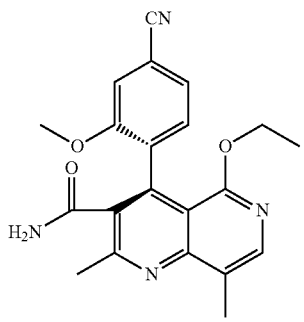

are electrochemically reduced.

The present invention provides a process for preparing the compounds of the formulae (I) and ent-(I) as described above, characterized in that the electrochemical reduction is conducted in a beaker cell or flow cell in the presence of methanol.

The present invention provides a process for preparing the compounds of the formulae (I) and ent-(I) as described above, characterized in that the electrochemical reduction is conducted in a beaker cell or flow cell in the presence of ethanol.

The present invention further provides a process for preparing the compounds of the formulae (I) and ent-(I) as described above (I)

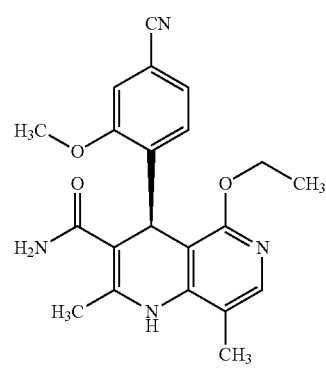

ent-(I)

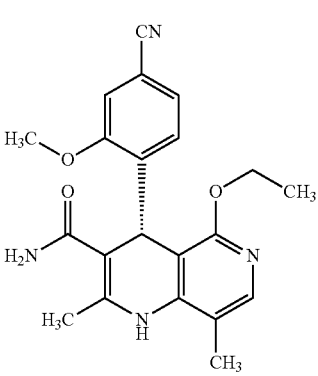

characterized in that compounds of the formulae (XVII) or M1a(S) or M1b(R) or a mixture of M1a(S) and M1b(R)

(XVII)

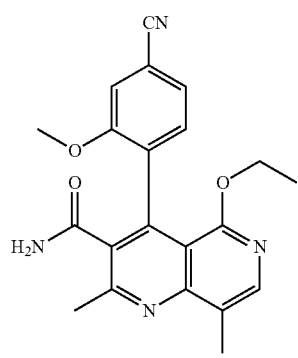

M1a(S)

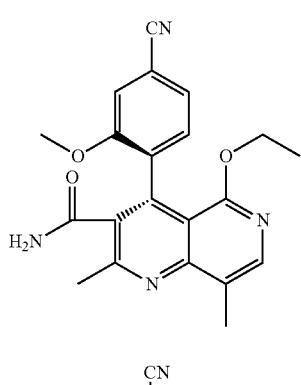

M1b(R)

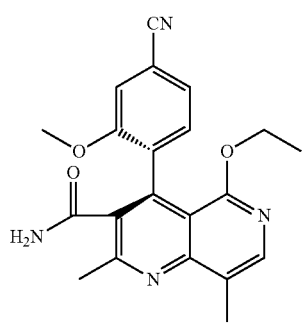

are electrochemically reduced, and characterized in that the compounds of the formulae (XVII), M1a(S) and M1b(R) are obtained by thermal isomerization of compounds of the formulae M1a(S) and M1b(R)

M1a(S)

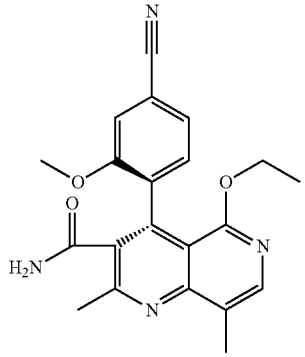

M1b(R)

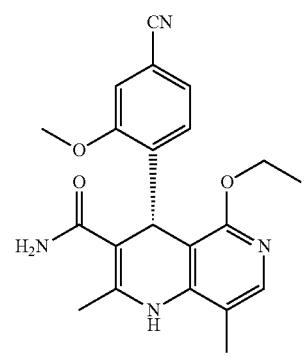

and characterized in that the compound of the formula ent-(I)

ent-(I)

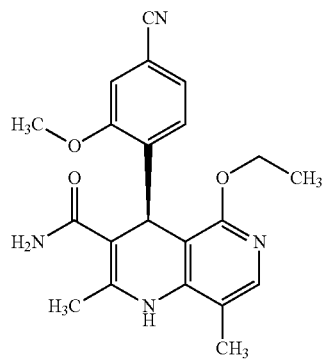

is oxidized.

The present invention provides a process for preparing the compounds of the formulae (I) and ent-(I) as described above (I)

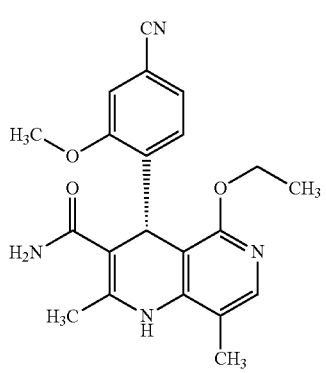
ent-(I)

characterized in that compounds of the formulae (XVII) or M1a(S) or M1b(R) or a mixture of M1a(S) and M1b(R)

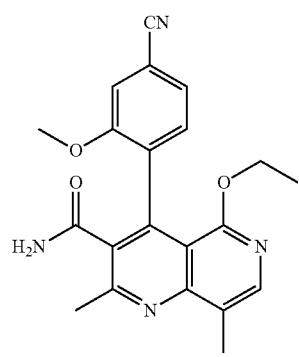
(XVII)

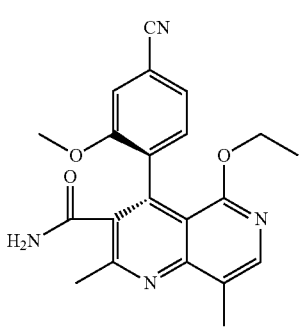
M1a(S)

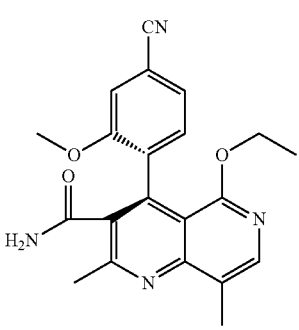
M1b(R)

are electrochemically reduced in a beaker cell or flow cell in the presence of methanol,
and characterized in that the compounds of the formulae (XVII), M1a(S) and M1b(R) are obtained by thermal isomerization of compounds of the formulae M1a(S) and M1b(R)

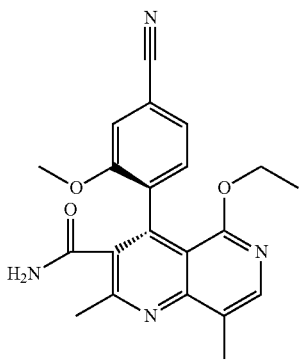
M1a(S)

M1b(R)

and characterized in that the compound of the formula ent-(I)

ent-(I)

is oxidized with chemical oxidizing agents.

The present invention provides a process for preparing the compounds of the formulae (I) and ent-(I) as described above (I)

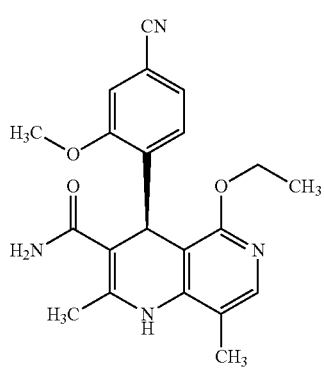

ent-(I)

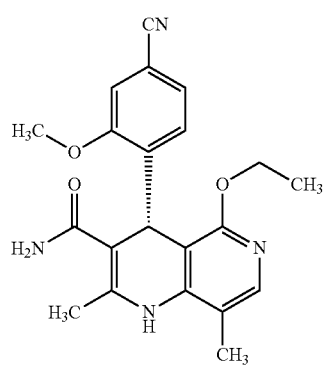

characterized in that compounds of the formulae (XVII) or M1a(S) or M1b(R) or a mixture of M1a(S) and M1b(R)

(XVII)

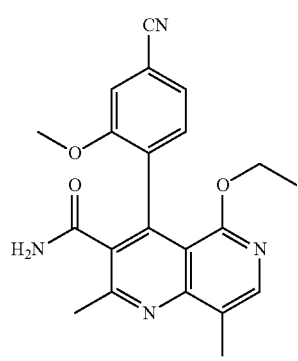

M1a(S)

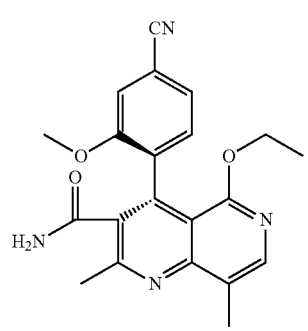

M1b(R)

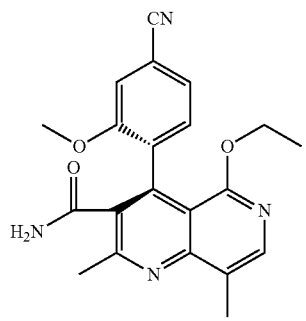

are electrochemically reduced in a beaker cell or flow cell in the presence of ethanol, and characterized in that the compounds of the formulae (XVII), M1a(S) and M1b(R) are obtained by thermal isomerization of compounds of the formulae M1a(S) and M1b(R)

M1a(S)

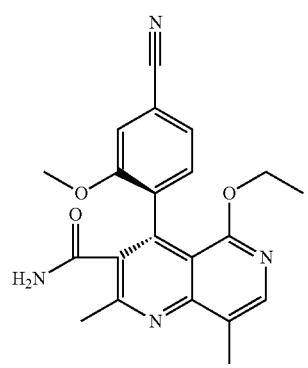

M1b(R)

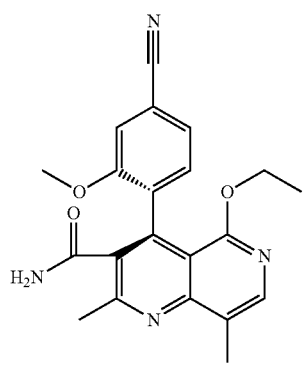

and characterized in that the compound of the formula ent-(I)

ent-(I)

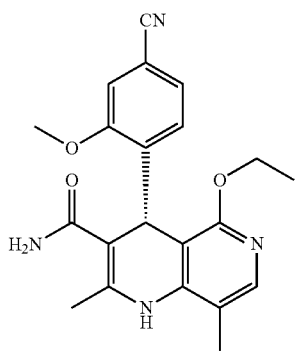

is oxidized with chemical oxidizing agents.

Experimental

Abbreviations and Acronyms

MS: mass from mass spectrometry
HPLC: high-performance liquid chromatography
DMF: dimethylformamide
Red-Al solution in toluene: sodium bis(2-methoxyethoxy) aluminium dihydride in toluene
THF: tetrahydrofuran
Aqu. HCl: aqueous hydrochloric acid
DMAP: 4-(dimethylamino)pyridine

EXAMPLES

Example 1

Methyl 4-bromo-2-methoxybenzoate (XV)

3.06 kg (22.12 mol) of potassium carbonate were initially charged in 3.6 l of acetone and heated to reflux. To this suspension were added 1.2 kg of 4-bromo-2-hydroxybenzoic acid (5.53 mol), suspended in 7.8 l of acetone, and the latter was rinsed in with 0.6 l of acetone. The suspension was heated under reflux for 1 hour (vigorous evolution of gas!). 2.65 kg (21.01 mol) of dimethyl sulphate were then added over 4 hours while boiling. The mixture was subsequently stirred under reflux for 2.5 hours. The solvent was largely distilled off (to the point of stirrability) and 12 l of toluene were added and the residual acetone was then distilled off at 110° C. About 3 l of distillate were distilled off, this being supplemented by addition of a further 3 l of toluene to the mixture. The mixture was allowed to cool to 20° C. and 10.8 l of water were added and vigorously stirred in. The organic phase was separated off and the aqueous phase was extracted once more with 6.1 l of toluene. The combined organic phases were washed with 3 l of saturated sodium chloride solution and the toluene phase is concentrated to about 4 l. Determination of the content by evaporation of a portion resulted in a converted yield of 1.306 kg (96.4% of theory). The solution was used directly in the subsequent stage.
HPLC-Method A: RT ca. 11.9 min.
MS (EIpos): m/z=245 [M+H]$^+$
$^1$H NMR (400 MHz, CD$_2$Cl$_2$): δ=3.84 (s, 3H), 3.90 (s, 3H), 7.12-7.20 (m, 2H), 7.62 (d, 1H).

Example 2

4-Bromo-2-methoxybenzaldehyde (XVI)

1.936 kg (6.22 mol) of a 65% Red-Al solution in toluene were charged with 1.25 l of toluene at −5° C. To this solution was added 0.66 kg (6.59 mol) of 1-methylpiperazine, which was rinsed in with 150 ml of toluene, keeping the temperature between −7 and −5° C. The mixture was then left to stir at 0° C. for 30 minutes. This solution was then added to a solution of 1.261 kg (5.147 mol) of methyl 4-bromo-2-methoxybenzoate (XV), dissolved in 4 l of toluene, keeping the temperature at −8 to 0° C. After rinsing in twice with 0.7 l of toluene, the mixture was then stirred at 0° C. for 1.5 hours. For the work-up, the solution was added to cold aqueous sulphuric acid at 0° C. (12.5 l of water+1.4 kg of conc. sulphuric acid). The temperature was to increase to a maximum to 10° C. (slow addition). The pH was adjusted to pH 1, if necessary, by addition of further sulphuric acid. The organic phase was separated off and the aqueous phase was extracted with 7.6 l of toluene. The combined organic phases were washed with 5.1 l of water and then substantially concentrated and the residue taken up in 10 l of DMF. The solution was again concentrated to a volume of about 5 l. Determination of the content by evaporation of a portion resulted in a converted yield of 1.041 kg (94.1% of theory). The solution was used directly in the subsequent stage.
HPLC-Method A: RT ca. 12.1 min.
MS (EIpos): m/z=162 [M+H]$^+$
$^1$H-NMR (CDCl$_3$, 400 MHz): δ=3.93 (3H, s), 7.17 (2H, m), 7.68 (1H, d), 10.40 (1H, s)

Example 3

4-Formyl-3-methoxybenzonitrile (VI)

719 g (3.34 mol) of 4-bromo-2-methoxybenzaldehyde (XVI) as a solution in 4.5 l of DMF were charged with 313 g (0.74 mol) of potassium hexacyanoferrate (K$_4$[Fe(CN)$_6$]) and 354 g (3.34 mol) of sodium carbonate and a further 1.2 l of DMF and 3.8 g (0.017 mol) of palladium acetate were added. The mixture was stirred at 120° C. for 3 hours. The mixture was left to cool to 20° C. and 5.7 l of water were added to the mixture. The mixture was extracted with 17 l of ethyl acetate and the aqueous phase was washed once more with 17 l of ethyl acetate. The organic phases were combined and substantially concentrated, taken up in 5 l of isopropanol and concentrated to about 2 l. The mixture was heated to boiling and 2 l of water were added dropwise. The mixture was allowed to cool to 50° C. and another 2 l of water were added. The mixture was cooled to 3° C. and stirred at this temperature for one hour. The product was filtered off and washed with water (2×1.2 l). The product was dried at 40° C. under vacuum.
Yield: 469 g (87% of theory) of a beige solid.
HPLC-Method A: RT ca. 8.3 min.
MS (EIpos): m/z=162 [M+H]+
1H-NMR (300 MHz, DMSO-d6): δ=3.98 (s, 3H), 7.53 (d, 1H), 7.80 (s, 1H), 7.81 (d, 1H), 10.37 (s, 1H).

Example 4

2-Cyanoethyl 4-(4-cyano-2-methoxyphenyl)-2,8-dimethyl-5-oxo-1,4,5,6-tetrahydro-1,6-naphthyridine-3-carboxylate (X)

Variant A 1.035 kg (6.422 mol) of 4-formyl-3-methoxybenzonitrile (VI), 1.246 kg (8.028 mol) of 2-cyanoethyl 3-oxobutanoate, 54.6 g (0.642 mol) of piperidine and 38.5 g (0.642 mol) of glacial acetic acid were heated under reflux in 10 l of dichloromethane for 6.5 hours on a water separator. The mixture was left to cool to room temperature and the organic phase was washed twice with 5 l of water each time. The dichloromethane phase was then concentrated at atmospheric pressure and the still stirrable residue was taken up in 15.47 kg of 2-butanol and 0.717 kg (5.78 mol) of 4-amino-5-methylpyridone was added. The residual dichloromethane was distilled off until an internal temperature of 98° C. was reached. The mixture was subsequently heated under reflux for 20 hours. The mixture was cooled to 0° C. and left to stir at this temperature for 4 hours, and the product was filtered off. The product was dried at 40° C. under vacuum under entraining gas.

Yield: 2.049 kg (87.6% of theory based on 4-amino-5-methylpyridone, since this component is used substoichiometrically) of a pale yellow solid.

HPLC-Method A: RT ca. 9.7 min.

MS (EIpos): m/z=405 [M+H]$^+$ $^1$H-NMR (300 MHz, DMSO-d$_6$): δ=2.03 (s, 3H), 2.35 (s, 3H), 2.80 (m, 2H), 3.74 (s, 3H), 4.04 (m, 1H), 4.11 (m, 1H), 5.20 (s, 1H), 6.95 (s, 1H), 7.23 (dd, 1H), 7.28-7.33 (m, 2H), 8.18 (s, 1H), 10.76 (s, 1H).

Variant B 1.344 kg (8.34 mol) of 4-formyl-3-methoxybenzonitrile (VI), 71 g (0.834 mol) of piperidine and 50.1 g (0.834 mol) of glacial acetic acid were charged in 6 l of isopropanol and at 30° C. a solution of 1.747 kg (11.26 mol) of 2-cyanoethyl 3-oxobutanoate in 670 ml of isopropanol was added over 3 hours. The mixture was then stirred at 30° C. for one hour. The mixture was cooled to 0-3° C. and stirred for 0.5 hour. The product was filtered off and washed twice with 450 ml of cold isopropanol each time. To determine the yield, the product was dried at 50° C. under vacuum (2.413 kg, 97% of theory); however, due to the high yield, the isopropanol-moist product was generally further processed directly. For this purpose, the product was taken up in 29 l of isopropanol and 1.277 kg (7.92 mol) of 4-amino-5-methylpyridone were added and then the mixture was heated to an internal temperature of 100° C. under a positive pressure of about 1.4 bar for 24 h in a closed vessel. The mixture was then cooled to 0° C. by means of a gradient over a period of 5 h and stirred at 0° C. for 3 hours. The product was then filtered off and washed with 2.1 l of cold isopropanol. The product was dried at 60° C. under vacuum.

Yield: 2.819 kg (88% of theory based on 4-amino-5-methylpyridone, since this component is used substoichiometrically) of a pale yellow solid.

HPLC-Method A: RT ca. 9.7 min.

MS (EIpos): m/z=405 [M+H]$^+$ $^1$H-NMR (300 MHz, DMSO-d$_6$): δ=2.03 (s, 3H), 2.35 (s, 3H), 2.80 (m, 2H), 3.74 (s, 3H), 4.04 (m, 1H), 4.11 (m, 1H), 5.20 (s, 1H), 6.95 (s, 1H), 7.23 (dd, 1H), 7.28-7.33 (m, 2H), 8.18 (s, 1H), 10.76 (s, 1H).

Example 5

2-Cyanoethyl 4-(4-cyano-2-methoxyphenyl)-5-ethoxy-2,8-dimethyl-1,4-dihydro-1,6-naphthyridine-3-carboxylate (XI)

2.142 kg (5.3 mol) of 2-cyanoethyl 4-(4-cyano-2-methoxyphenyl)-2,8-dimethyl-5-oxo-1,4,5,6-tetrahydro-1,6-naphthyridine-3-carboxylate (X) and 4.70 kg (29 mol) of triethyl orthoacetate were dissolved in 12.15 l of dimethylacetamide and 157.5 g of concentrated sulphuric acid were added. The mixture was heated at 115° C. for 1.5 hours and then cooled to 50° C. At 50° C., 12.15 l of water were added dropwise over 30 minutes. After completion of the addition, the mixture was seeded with 10 g of the title compound (XI) and a further 12.15 l of water were added dropwise over 30 minutes at 50° C. The mixture was cooled to 0° C. (gradient, 2 hours) and then stirred at 0° C. for two hours. The product was filtered off, washed twice with 7.7 l each time of water and dried at 50° C. under vacuum.

Yield: 2114.2 g (92.2% of theory) of a pale yellow solid.

HPLC-Method B: RT ca. 10.2 min.

MS (EIpos): m/z=433 [M+H]$^+$ $^1$H-NMR (300 MHz, DMSO-d$_6$): δ=1.11 (t, 3H), 2.16 (s, 3H), 2.42 (s, 3H), 2.78 (m, 2H), 3.77 (s, 3H), 4.01-4.13 (m, 4H), 5.37 (s, 1H), 7.25 (d, 1H), 7.28-7.33 (m, 2H), 7.60 (s, 1H), 8.35 (s, 1H).

Alternatively, the reaction may be carried out in NMP (1-methyl-2-pyrrolidone)

2-Cyanoethyl 4-(4-cyano-2-methoxyphenyl)-5-ethoxy-2,8-dimethyl-1,4-dihydro-1,6-naphthyridine-3-carboxylate (XI)

2.142 kg (5.3 mol) of 2-cyanoethyl 4-(4-cyano-2-methoxyphenyl)-2,8-dimethyl-5-oxo-1,4,5,6-tetrahydro-1,6-naphthyridine-3-carboxylate (X) and 2.35 kg (14.5 mol) of triethyl orthoacetate were dissolved in 3.21 kg of NMP (1-methyl-2-pyrrolidone) and 157.5 g of concentrated sulphuric acid were added. The mixture was heated at 115° C. for 1.5 hours and then cooled to 50° C. At 50° C., 2.2 l of water were added dropwise over 30 minutes. After completion of the addition, the mixture was seeded with 10 g of the title compound (XI) and a further 4.4 l of water were added dropwise over 30 minutes at 50° C. The mixture was cooled to 0° C. (gradient, 2 hours) and then stirred at 0° C. for two hours. The product was filtered off, washed twice with 4 l each time of water and dried at 50° C. under vacuum.

Yield: 2180.7 g (95.1% of theory) of a pale yellow solid.

HPLC method B: RT about 10.2 min.

Example 6

4-(4-Cyano-2-methoxyphenyl)-5-ethoxy-2,8-dimethyl-1,4-dihydro-1,6-naphthyridine-3-carboxylic acid (XII)

2.00 kg (4.624 mol) of 2-cyanoethyl 4-(4-cyano-2-methoxyphenyl)-5-ethoxy-2,8-dimethyl-1,4-dihydro-1,6-naphthyridine-3-carboxylate (XI) were dissolved in a mixture of 12 l of THF and 6 l of water and cooled to 0° C. To this solution was added dropwise, at 0° C. over the course of 15 minutes, an aqueous sodium hydroxide solution (prepared from 0.82 kg of 45% aq. NaOH (9.248 mol) and 4.23 l of water), and the mixture was stirred at 0° C. for 1.5 hours. The mixture was extracted twice with 4.8 l of methyl tert-butyl ether each time and once with 4.8 l of ethyl acetate. The aqueous solution at 0° C. was adjusted to pH 7 with dilute hydrochloric acid (prepared from 0.371 kg of 37% HCl and 1.51 l of water). The solution was allowed to warm to 20° C. and an aqueous solution of 2.05 kg of ammonium chloride in 5.54 l of water was added. The solution was stirred at 20° C. for 1 hour, and the product was filtered and washed twice with 1.5 l of water each time and once with 4 l of acetonitrile. The product was dried at 40° C. under vacuum under entraining gas.

Yield: 1736.9 g (99% of theory) of an almost colourless powder (very slight yellow tint).
HPLC-Method C: RT: ca. 6.8 min.
MS (EIpos): m/z=380 [M+H]$^+$
$^1$H-NMR (300 MHz, DMSO-d$_6$): δ=1.14 (t, 3H), 2.14 (s, 3H), 2.37 (s, 3H), 3.73 (s, 3H), 4.04 (m, 2H), 5.33 (s, 1H), 7.26 (m, 2H), 7.32 (s, 1H), 7.57 (s, 1H), 8.16 (s, 1H), 11.43 (br. s, 1H).

Alternative work-up using toluene for the extraction:

4-(4-Cyano-2-methoxyphenyl)-5-ethoxy-2,8-dimethyl-1,4-dihydro-1,6-naphthyridine-3-carboxylic acid (XII)

2.00 kg (4.624 mol) of 2-cyanoethyl 4-(4-cyano-2-methoxyphenyl)-5-ethoxy-2,8-dimethyl-1,4-dihydro-1,6-naphthyridine-3-carboxylate (XI) were dissolved in a mixture of 12 l of THF and 6 l of water and cooled to 0° C. To this solution was added dropwise, at 0° C. over the course of 15 minutes, an aqueous sodium hydroxide solution (prepared from 0.82 kg of 45% aq. NaOH (9.248 mol) and 4.23 l of water, and the mixture was stirred at 0° C. for 1.5 hours. 5 l of toluene and 381.3 g of sodium acetate were added and the mixture was stirred vigorously. The phases were allowed to settle and the organic phase was separated. The aqueous phase was adjusted to pH 6.9 with 10% hydrochloric acid (at about pH 9.5 the solution was seeded with 10 g of the title compound). After precipitation of the product was complete, the mixture was stirred at 0° C. for one hour and was then filtered and washed twice with 4 l of water each time and twice with 153 ml of toluene each time. The product was dried at 40° C. under vacuum under entraining gas (nitrogen, 200 mbar). Yield: 1719.5 g (98% of theory) of an almost colourless powder (very slight yellow tint).
HPLC method C: RT: about 6.8 min.

Example 7

4-(4-Cyano-2-methoxyphenyl)-5-ethoxy-2,8-dimethyl-1,4-dihydro-1,6-naphthyridine-3-carboxamide (XIII)

1.60 kg (4.22 mol) of 4-(4-cyano-2-methoxyphenyl)-5-ethoxy-2,8-dimethyl-1,4-dihydro-1,6-naphthyridine-3-carboxylic acid (XII) and 958 g (5.91 mol) of 1,1-carbodiimidazole were charged in 8 l of THF and 51 g (0.417 mol) of DMAP were added at 20° C. The mixture was stirred at 20° C. (evolution of gas!) for one hour and then heated to 50° C. for 2.5 hours. 2.973 kg (18.42 mol) of hexamethyldisilazane were added to this solution, which was boiled under reflux for 22 hours. A further 1.8 l of THF were added and the mixture was cooled to 5° C. A mixture of 1.17 l of THF and 835 g of water was added over 3 hours such that the temperature remained between 5 and 20° C. The mixture was subsequently boiled under reflux for one hour, then cooled via a gradient (3 hours) to 0° C. and stirred at this temperature for one hour. The product was filtered off and washed twice with 2.4 l of THF each time and twice with 3.2 l of water each time. The product was dried at 70° C. under vacuum under entraining gas.
Yield: 1.501 kg (94% of theory) of an almost colourless powder (very slight yellow tint).
HPLC-Method B: RT ca. 6.7 min.
MS (EIpos): m/z=379 [M+H]$^+$
$^1$H-NMR (300 MHz, DMSO-d$_6$): δ=1.05 (t, 3H), 2.12 (s, 3H), 2.18 (s, 3H), 3.82 (s, 3H), 3.99-4.07 (m, 2H), 5.37 (s, 1H), 6.60-6.84 (m, 2H), 7.14 (d, 1H), 7.28 (dd, 1H), 7.37 (d, 1H), 7.55 (s, 1H), 7.69 (s, 1H).

Example 8

(4S)-4-(4-Cyano-2-methoxyphenyl)-5-ethoxy-2,8-dimethyl-1,4-dihydro-1,6-naphthyridine-3-carboxamide (I) as a solution in 40:60 acetonitrile/methanol Enantiomer Separation in an SMB System
The feed solution was a solution corresponding to a concentration consisting of 50 g of racemic 4-(4-cyano-2-methoxyphenyl)-5-ethoxy-2,8-dimethyl-1,4-dihydro-1,6-naphthyridine-3-carboxamide (XIII), dissolved in 1 liter of a mixture of 60:40 methanol/acetonitrile.
The solution was chromatographed by means of an SMB system on a stationary phase: Chiralpak AS-V, 20 µm. The pressure was 30 bar and a mixture of methanol/acetonitrile 60:40 was used as eluent.
9.00 kg of 4-(4-cyano-2-methoxyphenyl)-5-ethoxy-2,8-dimethyl-1,4-dihydro-1,6-naphthyridine-3-carboxamide (XII) were dissolved in 180 l of a mixture consisting of methanol/acetonitrile 60:40 and chromatographed by means of SMB. After concentrating the product-containing fractions, 69.68 liters of a 6.2% solution (corresponding to 4.32 kg of (4S)-4-(4-cyano-2-methoxyphenyl)-5-ethoxy-2,8-dimethyl-1,4-dihydro-1,6-naphthyridine-3-carboxamide (I) as a solution in acetonitrile/methanol 40:60) were obtained.
Yield: 4.32 kg of (S) enantiomer (48% of theory), as a colourless fraction dissolved in 69.68 liters of acetonitrile/methanol 40:60.
Enantiomeric purity: >98.5% e.e. (HPLC, Method D)
A sample is concentrated under vacuum and gives: MS (EIpos): m/z=379 [M+H]$^+$
$^1$H-NMR (300 MHz, DMSO-d$_6$): δ=1.05 (t, 3H), 2.12 (s, 3H), 2.18 (s, 3H), 3.82 (s, 3H), 3.99-4.07 (m, 2H), 5.37 (s, 1H), 6.60-6.84 (m, 2H), 7.14 (d, 1H), 7.28 (dd, 1H), 7.37 (d, 1H), 7.55 (s, 1H), 7.69 (s, 1H).
The (R) enantiomer ent-(I) was isolated in an analogous manner.
Yield: 4.41 kg of (R) enantiomer (48% of theory), as a colourless fraction dissolved in 71.00 liters of acetonitrile/methanol 40:60.
Enantiomeric purity: >98.5% e.e. (HPLC, Method D)
A sample was concentrated under vacuum and gives: MS (EIpos): m/z=379 [M+H]+
1H-NMR (300 MHz, DMSO-d6): δ=1.05 (t, 3H), 2.12 (s, 3H), 2.18 (s, 3H), 3.82 (s, 3H), 3.99-4.07 (m, 2H), 5.37 (s, 1H), 6.60-6.84 (m, 2H), 7.14 (d, 1H), 7.28 (dd, 1H), 7.37 (d, 1H), 7.55 (s, 1H), 7.69 (s, 1H).

Example 9

(4S)-4-(4-Cyano-2-methoxyphenyl)-5-ethoxy-2,8-dimethyl-1,4-dihydro-1,6-naphthyridine-3-carboxamide (I)

Crystallization and Polymorph Adjustment 64.52 liters of a 6.2% solution from Example 8 in a mixture of acetonitrile/methanol 40:60 (corresponding to 4.00 kg of compound I) were filtered through a filter cartridge (1.2 um) and subsequently sufficiently concentrated at 250 mbar such that the solution was still stirrable. 48 l of ethanol, denatured with toluene, was added and distilled again at 250 mbar up to the limit of stirrability (redistillation in ethanol). A further 48 l of ethanol, denatured with toluene, were added and then distilled off at atmospheric pressure down to a total volume of about 14 l (jacket temperature 98° C.). The mixture was cooled via a gradient (4 hours) to 0° C., stirred at 0° C. for 2 hours and the product filtered off. The product was washed twice with 4 l of cold ethanol each time and then dried at 50° C. under vacuum.

Yield: 3.64 kg (91% of theory) of a colourless crystalline powder.

Enantiomeric purity: >>99% e.e. (HPLC Method D); retention times/RRT: (4S)-4-(4-cyano-2-methoxyphenyl)-5-ethoxy-2,8-dimethyl-1,4-dihydro-1,6-naphthyridine-3-carboxamide (1) about 11 min. RRT: 1.00; (4R)-4-(4-cyano-2-methoxyphenyl)-5-ethoxy-2,8-dimethyl-1,4-dihydro-1,6-naphthyridine-3-carboxamide (I) about 9 min. RRT: 0.82

Purity: >99.8% (HPLC Method B), RT: about 6.7 min.

Content: 99.9% (relative to external standard) specific rotation (chloroform, 589 nm, 19.7° C., c=0.38600 g/100 ml): −148.8°.

MS (EIpos): m/z=379 [M+H]+

$^1$H-NMR (300 MHz, DMSO-d$_6$): δ=1.05 (t, 3H), 2.12 (s, 3H), 2.18 (s, 3H), 3.82 (s, 3H), 3.99-4.07 (m, 2H), 5.37 (s, 1H), 6.60-6.84 (m, 2H), 7.14 (d, 1H), 7.28 (dd, 1H), 7.37 (d, 1H), 7.55 (s, 1H), 7.69 (s, 1H).

Melting point: 252° C. (compound of the formula ent-(I) in crystalline form of polymorph I)

The (R) enantiomer ent-(I) is isolated in an analogous manner. However, further concentration is effected in order to minimize yield losses:

71.00 liters of an about 6.2% solution from Example 8 in a mixture of acetonitrile/methanol 40:60 (corresponding to 4.00 kg of compound ent-(I)) were filtered through a filter cartridge (1.2 um) and subsequently sufficiently concentrated at 250 mbar such that the solution was still stirrable. 48 l of ethanol, denatured with toluene, were added and distilled again at 250 mbar up to the limit of stirrability (redistillation in ethanol). A further 48 l of ethanol, denatured with toluene, was added and then distilled off at atmospheric pressure down to a total volume of about 10 l (jacket temperature 98° C.). The mixture was cooled via a gradient (4 hours) to 0° C., stirred at 0° C. for 2 hours and the product filtered off. The product was washed twice with 2 l of cold ethanol each time and then dried at 50° C. under vacuum.

Yield: 3.88 kg (97% of theory) of a colourless crystalline powder.

Enantiomeric purity: >>99% e.e. (HPLC Method D); retention times/RRT: (4S)-4-(4-cyano-2-methoxyphenyl)-5-ethoxy-2,8-dimethyl-1,4-dihydro-1,6-naphthyridine-3-carboxamide (1) about 11 min. RRT: 1.00; (4R)-4-(4-cyano-2-methoxyphenyl)-5-ethoxy-2,8-dimethyl-1,4-dihydro-1,6-naphthyridine-3-carboxamide (I) about 9 min. RRT: 0.82

Purity: >99.8% (HPLC Method B), RT: about 6.7 min.

Content: 99.9% (relative to external standard) specific rotation (chloroform, 589 nm, 19.7° C., c=0.38600 g/100 ml): +148.8°.

MS (EIpos): m/z=379 [M+H]+

1H-NMR (300 MHz, DMSO-d6): □=1.05 (t, 3H), 2.12 (s, 3H), 2.18 (s, 3H), 3.82 (s, 3H), 3.99-4.07 (m, 2H), 5.37 (s, 1H), 6.60-6.84 (m, 2H), 7.14 (d, 1H), 7.28 (dd, 1H), 7.37 (d, 1H), 7.55 (s, 1H), 7.69 (s, 1H).

Melting point: 252° C.

Chemical Oxidation

Example 10

Preparation of Racemic (XVII) from Racemic (XIII) by Chemical Methods

Rac 4-(4-cyano-2-methoxyphenyl)-5-ethoxy-2,8-dimethyl-1,6-naphthyridine-3-carboxamide 100.00 g (264.25 mmol) of 4(R,S)-4-(4-cyano-2-methoxyphenyl)-5-ethoxy-2,8-dimethyl-1,4-dihydro-1,6-naphthyridine-3-carboxamide (XIII) were initially charged in 4 kg of dichloromethane, and 68.98 g (303.88 mmol) of 2,3-dichloro-5,6-dicyano-1,4-benzoquinone (DDQ) were added at 20° C. The mixture was stirred at 20° C. for 1 h. The precipitated solid was filtered off and washed twice with 400 g each time of dichloromethane. The mixture was concentrated to dryness under reduced pressure and the residue was taken up in 1200 g of ethanol. The mixture was heated to reflux and about 800 g of ethanol were distilled off. The mixture was left to cool down to room temperature and stirred at 20° C. for a further 1 h. The product was filtered off and washed with a little ethanol (about 80 g), and dried under reduced pressure overnight (50° C.).

Yield: 87.30 g (87.54% of theory) of a beige solid.

MS (EIpos): m/z=378 [M+H]+

1H NMR (500 MHz, DMSO-d6): δ=0.72 (t, 3H), 2.50 (s, 3H), 2.70 (s, 3H), 3.65 (s, 1H), 4.00 (m (broad), 2H), 7.30 (d, 1H), 7.45 (d, 1H), 7.50 (s, 2H), 7.69 (s, 1H), 8.05 (s, 1H)

Example 11a

Preparation of M1a(S) from ent-(I) by Chemical Methods (S)-4-(4-cyano-2-methoxyphenyl)-5-ethoxy-2,8-dimethyl-1,6-naphthyridine-3-carboxamide (M1a (S))

100.00 g (264.25 mmol) of 4(R)-4-(4-cyano-2-methoxyphenyl)-5-ethoxy-2,8-dimethyl-1,4-dihydro-1,6-naphthyridine-3-carboxamide (ent-(I)) were initially charged in 4 kg of dichloromethane, and 68.98 g (303.88 mmol) of 2,3-dichloro-5,6-dicyano-1,4-benzoquinone (DDQ) were added at 20° C. The mixture was stirred at 20° C. for 1 h. The precipitated solid was filtered off and washed twice with 400 g each time of dichloromethane. The mixture was concentrated to dryness under reduced pressure and the residue was taken up in 1200 g of ethanol. The mixture was heated to reflux and about 800 g of ethanol were distilled off. The mixture was left to cool down to room temperature and stirred at 20° C. for a further 1 h. The product was filtered off and washed with a little ethanol (about 80 g), and dried under reduced pressure overnight (50° C.).

Yield: 85.80 g (86.04% of theory) of a beige solid.

HPLC: RT about 6.08 min. (Chiral phase: Chiralpak AS-H (250×4 mm), eluent: i-hexane:ethanol=50:50.)

MS (EIpos): m/z=378 [M+H]+

1H NMR (500 MHz, DMSO-d6): δ=0.72 (t, 3H), 2.50 (s, 3H), 2.70 (s, 3H), 3.65 (s, 1H), 4.00 (m (broad), 2H), 7.30 (d, 1H), 7.45 (d, 1H), 7.50 (s, 2H), 7.69 (s, 1H), 8.05 (s, 1H)

Example 11b

Preparation of M1b(R) from (I)

(R)-4-(4-cyano-2-methoxyphenyl)-5-ethoxy-2,8-dimethyl-1,6-naphthyridine-3-carboxamide (M1b (R))

100.00 g (264.25 mmol) of 4(S)-4-(4-cyano-2-methoxyphenyl)-5-ethoxy-2,8-dimethyl-1,4-dihydro-1,6-naphthyridine-3-carboxamide (I) were initially charged in 4 kg of dichloromethane, and 68.98 g (303.88 mmol) of 2,3-dichloro-5,6-dicyano-1,4-benzoquinone (DDQ) were added at 20° C. The mixture was stirred at 20° C. for 1 h. The precipitated solid was filtered off and washed twice with 400 g each time of dichloromethane. The mixture was concentrated to dryness under reduced pressure and the residue was taken up in 1200 g of ethanol. The mixture was heated to reflux and about 800 g of ethanol were distilled off. The mixture was left to cool down to room temperature and stirred at 20° C. for a further 1 h. The product was filtered off and washed with a little ethanol (about 80 g), and dried under reduced pressure overnight (50° C.).

Yield: 85.80 g (86.04% of theory) of a beige solid.

HPLC: RT about 9.03 min. (Chiral phase: Chiralpak AS-H (250×4 mm), eluent: i-hexane:ethanol=50:50.)

MS (EIpos): m/z=378 [M+H]+

1H NMR (500 MHz, DMSO-d6): δ=0.72 (t, 3H), 2.50 (s, 3H), 2.70 (s, 3H), 3.65 (s, 1H), 4.00 (m, broad), 2H), 7.30 (d, 1H), 7.45 (d, 1H), 7.50 (s, 2H), 7.69 (s, 1H), 8.05 (s, 1H)

Example 12a

Preparation of Racemic (XVII) from ent-(I)

4-(4-Cyano-2-methoxyphenyl)-5-ethoxy-2,8-dimethyl-1,6-naphthyridine-3-carboxamide 100.00 g (264.25 mmol) of 4(R)-4-(4-cyano-2-methoxyphenyl)-5-ethoxy-2,8-dimethyl-1,4-dihydro-1,6-naphthyridine-3-carboxamide (ent-(I)) were initially charged in 4 kg of dichloromethane, and 68.98 g (303.88 mmol) of 2,3-dichloro-5,6-dicyano-1,4-benzoquinone (DDQ) were added at 20° C. The mixture was stirred at 20° C. for 1 h. The precipitated solid was filtered off and washed twice with 400 g each time of dichloromethane. The mixture was concentrated to dryness under reduced pressure and the residue was taken up in 1200 g of ethanol. The mixture was heated in an autoclave at 120° C. under pressure for 3 hours, and then about 900 g of ethanol were distilled off. The mixture was left to cool down to room temperature and stirred at 20° C. for a further 1 h. The product was filtered off and washed with a little ethanol (about 40 g), and dried under reduced pressure overnight (50° C.).

Yield: 92.47 g (92.73% of theory) of a beige solid.

MS (EIpos): m/z=378 [M+H]+

1H NMR (500 MHz, DMSO-d6): δ=0.72 (t, 3H), 2.50 (s, 3H), 2.70 (s, 3H), 3.65 (s, 1H), 4.00 (m, broad), 2H), 7.30 (d, 1H), 7.45 (d, 1H), 7.50 (s, 2H), 7.69 (s, 1H), 8.05 (s, 1H)

Example 12b

Synthesis of M1a (S) from ent-(I) by HNO$_3$ Oxidation

Perform reaction under Nitrogen. 75.0 g 4(R)-4-(4-Cyano-2-methoxyphenyl)-5-ethoxy-2,8-dimethyl-1,4-dihydro-1,6-naphthyridine-3-carbox-amide (ent(I)) were suspended in 1000 g acetonitrile and cooled to 9° C. Then 12.68 g fuming HNO$_3$ were added in 10 minutes. The compound lumped shortly together, but dissolved easily later. The solution was warmed to room temperature (in 1 h) and a light yellow and clear solution was obtained. The solution was stirred for 4 h at room temperature, after 30 minutes an orange solution was obtained followed by a yellow suspension. After 4 h the mixture was cooled to 10° C. and then quenched with 50 ml water. Then 80 ml of an aqueous satured NaHCO$_3$—solution was added until the pH reached pH 7.2 (yellow suspension). The crystals were isolated (first crop) and washed with water. The filtrate was reduced with a rotatory evaporator at 40° C. to ⅓ of the original volume, then stirred for 1.5 h in an ice bath (5° C.), again the crystals were isolated (second crop), and were washed with 100 ml cold water. The crystals were dried overnight in vacuum.

Yield: 59.7 g=86.7% th.
Analytics: first crop
EE: M1a: 83.6% M1b: 16.4%
Assay: 98.9%
Analytics: Second Crop
EE: M1a: 77.4% M1b: 22.6%
Purity: 99.2 area %
Assay: 94.5%

Synthesis of Racemic M1(XVII) from Enriched M1a (S)

100 g enriched M1a (EE: M1a: 83.6% M1b: 16.4%) were suspended in 1000 ml n-butanol and heated to 135° C. bath temperature. It was stirred for 6 h under reflux (thin yellow suspension). It was cooled to room temperature and stirred overnight. The solution was reduced with a rotatory evaporator at 50° C. (to a suspension which could be stirred) and then stirred for 1 h at 5° C. The crystals were washed with a small amount of cold butanol and then dried overnight in vacuum at 40° C.<200 mbar.

Yield: 85.9 g=85.9% th. (Corrected on assay of educt: 90.9% th.)
EE: 50.5% M1a, 49.5% M1b
Electrochemical Oxidation

Example 24

Cyclic voltammetry of (I) in the absence of 2,3-dichloro-5,6-dicyano-1,4-benzoquinone (DDQ) 2.17 g (10 mmol) of tetraethylammonium tetrafluoroborate (Et4NBF4) are dissolved in 100 ml of acetonitrile. Then 378.4 mg (1 mmol) of (4S)-4-(4-cyano-2-methoxyphenyl)-5-ethoxy-2,8-dimethyl-1,4-dihydro-1,6-naphthyridine-3-carboxamide (I) are added.

The cyclic voltammetry is conducted with a Pt cage as working electrode and a Pt wire as counterelectrode and Ag/Ag+ (10 mmol/l) in acetonitrile as reference electrode over 10 cycles with a scan rate of 250 or 100 mV/s.

Example 25

Cyclic Voltammetry of (VI) in the Presence of DDQ
2.17 g (10 mmol) of tetraethylammonium tetrafluoroborate (Et4NBF4) are dissolved in 100 ml of acetonitrile. Then 22.7 mg (0.1 mmol) of DDQ and 378.4 mg (1 mmol) of the compound of the formula (I) are added. The molar DDQ:DHP ratio is thus 1:10.

The cyclic voltammetry is conducted with a Pt cage as working electrode and a Pt wire as counterelectrode and Ag/Ag+ (10 mmol/l) in acetonitrile as reference electrode over 10 cycles with a scan rate of 250 or 100 mV/s.

Example 26

Oxidation of ent-(I) in the Presence of DDQ (10 mol %)

2.17 g (10 mmol) of tetraethylammonium tetrafluoroborate (Et4NBF4) are dissolved in 100 ml of acetonitrile. Then 22.7 mg (0.1 mmol) of DDQ and 378.4 mg (1 mmol) of the compound of the formula ent-(I) (10 mmol) are added. The molar DDQ:ent-(I) ratio is thus 1:10.

Then the solution is electrolysed at constant potential, with the anode (working electrode) maintained at a potential of +300 mV versus Ag/Ag+(10 mmol/1). After passage of 180 C of charge (corresponding to 2.1 F) (over a period of about 2 h), the reaction is stopped. At this point, the yield of (XVII) was 94% with an atropisomer ratio M1a(S):M1b(R)=90:10.

The reaction profile was monitored by frequent withdrawal of samples and analysis by means of HPLC. The profile is shown in FIG. 6. The product (XVII) and the reactants increase and decrease with time. The formation of product is in accordance with the transfer of electrical charge, which indicates a high power efficiency.

Example 27

Oxidation of (I) in the Presence of DDQ (1 mol %)

2.17 g (10 mmol) of tetraethylammonium tetrafluoroborate (Et4NBF4) are dissolved in 100 ml of acetonitrile. Then 2.3 mg (0.01 mmol) of DDQ and 378.4 mg (1 mmol) of the compound of the formula (I) are added. The molar DDQ:(I) ratio is thus 1:100.

Then the solution is electrolysed at constant potential, with the anode (working electrode) maintained at a potential of +300 mV versus Ag/Ag+ (10 mmol/1). After passage of 180 C of charge (2.1 F) (over a period of about 4 h), the reaction is stopped. At this point, the yield of M1 according to HPLC analysis was 89% (M1a:M1b=13:87). By subsequent addition of 2.3 mg (0.01 mmol) of DDQ (and hence an increase in the proportion thereof to 2 mol %) and subsequent electrolysis over a period of 1 h, the yield according to HPLC analysis rose to 96% of the compound of the formula (XVII) (M1a(S):M1b(R)=13:87).

Example 28

Direct Electrochemical Oxidation of (XIII)

2.17 g (10 mmol) of tetraethylammonium tetrafluoroborate (Et4NBF4) are dissolved in 100 ml of acetonitrile. Then 378.4 mg (1 mmol) of the compound of the formula (XIII) are added.

Then the solution is electrolysed at constant potential, with the anode (working electrode) maintained at a potential of +1000 mV versus Ag/Ag+ (10 mmol/1). After passage of 180 C of charge (2.1 F) (over a period of about 2 h), the reaction is stopped. At this point, the yield of (XVII) was <50%.

Example 29

Racemization and Isolation of (XVII) After Mediated Electrochemical Oxidation

The solution from Example 26 is passed on in 200 g of ethanol. The mixture was heated in an autoclave at 120° C. under pressure for 3 hours, and about 150 g of ethanol were distilled off. The mixture was left to cool down to room temperature and stirred at 20° C. for a further 1 h. The product was filtered off and washed with a little ethanol (about 80 g), and dried under reduced pressure overnight (50° C.).

Electrochemical Reduction

Reactants used for the electrochemical reduction were the atropisomers of the compound 4-(4-cyano-2-methoxyphenyl)-5-ethoxy-2,8-dimethyl-1,6-naphthyridine-3-carboxamide, i.e. the compounds M1a(S) or M1b(R) or else the mixture thereof (rac. M1), obtained by the oxidation of the compound of the formula ent-I, the compound of the formula (XIII) or, by comparison, from the compound of the formula (I).

The conversion of these reactants, and also the yield of the target product, were determined by continuous sampling during the electrochemical reduction and subsequent HPLC analysis [HPLC Method E]. The enantiomeric ratio I to ent-(I) normalized to 100 was determined once at the end of the experiment, in addition, by means of a chiral HPLC method [HPLC Method F].

Example 13

Reduction of Compound M1b(R) (0.2 g Batch)

The construction used was a three-electrode system consisting of the working electrode [Winkler mesh electrode consisting of platinum/iridium 90%/10% (225 meshes/cm2, wire diameter=0.12 mm, cylinder geometry), a counterelectrode [from ALS: platinum wire, coiled, length 23 cm with wire diameter 0.5 mm] and a reference electrode [from ALS: Ag/Ag+ type; nonaqueous reference electrode with 0.01 M AgNO3 and 0.1 M tetrabutylammonium perchlorate in acetonitrile]. The counterelectrode was positioned in a glass tube closed by means of a membrane at the base. The membrane used was a PTFE filter [from: Sartorius Stedim Biotech GmbH] having a pore size of 0.45 µm. The current and voltage source used was a potentiostat from Gamry [type: Interface 1000].

0.2 g of the compound M1b(R) (0.53 mmol) obtained from Example 11b was dissolved in 75 g of methanol. In addition, 3.2 g of tetraethylammonium tetrafluoroborate conductive salt (14.74 mmol) were added. The beaker was filled with this solution. A substrate-free solution consisting of 0.16 M tetraethylammonium tetrafluoroborate in methanol was added to the counterelectrode chamber, which was divided off by the membrane.

For 2 hours, the current was regulated to a level of −30 mA. Thereafter, the current was adjusted to −180 mA. After a further 4 h, a conversion of >99% and an in situ yield of >97% were determined. The enantiomer ratio (I):ent-(I) was determined as 79:21.

Example 14

Reduction of Compound M1b(R) (1.0 g Batch)

The construction used was again a three-electrode system as described in Example 13.

1.0 g of the compound M1b(R) (2.66 mmol) obtained from Example 11b was suspended in 80 g methanol, and the substrate dissolved virtually completely. In addition, 4.5 g of tetraethylammonium tetrafluoroborate conductive salt (20.73 mmol) were added. The beaker was filled with this solution. A substrate-free solution consisting of 0.21 M tetraethylammonium tetrafluoroborate in methanol was added to the counterelectrode chamber, which was divided off by the membrane.

The experiment was run under potentiostatic conditions, but the target potential of −3 V versus the reference electrode was not attained. Over the entire duration of the experiment, the maximum possible cell voltage that could be established by the Interface 1000 was applied (compliance voltage according to the manufacturer: 22 V). After an experimental period of 6 h and a charge flow of 2650 coulombs (corresponding to an average current flow of 122 mA), a conversion of >99% and an in situ target product yield >97% were determined. The enantiomer ratio I:ent-(I) was determined as 76:24.

Example 15

Reduction of Compound M1b(R) (1.0 g Batch)

The construction used was again a three-electrode system as described in Example 13.

1.0 g of the compound M1b(R) (2.66 mmol) obtained from Example 11b was suspended in 80 g methanol, and the substrate dissolved virtually completely. In addition, 3.5 g of tetraethylammonium tetrafluoroborate conductive salt (16.12 mmol) were added. The beaker was filled with this solution. A substrate-free solution consisting of 0.16 M tetraethylammonium tetrafluoroborate in methanol was added to the counterelectrode chamber, which was divided off by the membrane.

The experiment was run under potentiostatic conditions analogously to Ex. 14.

After an experimental period of 4 h and a charge flow of 2193 coulombs (corresponding to an average current flow of 152 mA), the experiment was ended. The conversion at this time was 79%, and the in situ target product yield was determined as 79%. The enantiomer ratio (I):ent-(I) was determined as 78:22.

Example 16

Reduction of Compound M1a(S) (0.5 g Batch)

The construction used was again a three-electrode system as described in Example 13.

0.5 g of the compound M1a(S) (1.33 mmol) obtained from Example 11a was dissolved in 80 g of methanol. In addition, 3.5 g of tetraethylammonium tetrafluoroborate conductive salt (16.12 mmol) were added. The beaker was filled with this solution. A substrate-free solution consisting of 0.16 M tetraethylammonium tetrafluoroborate in methanol was added to the counterelectrode chamber, which was divided off by the membrane.

The experiment was run under potentiostatic conditions analogously to Ex. 14.

After an experimental period of 5 h and a charge flow of 2132 coulombs (corresponding to an average current flow of 118 mA), the experiment was ended. The conversion at this time was 73%, and the in situ target product yield was determined as 73%. The enantiomer ratio (I):ent-(I) was determined as 22:78.

Example 17

Preparation of Racemic (XIII) from Racemic M1(XVII): Reduction of the Atropisomer Mixture Consisting of 50% by Weight of M1b(R) and 50% by Weight of M1a(S) (0.5 g Racemate Batch)

The construction used was again a three-electrode system as described in Example 13.

0.5 g of the M1a(S)/M1b(R) racemate (1.33 mmol) obtained from Example 12 was dissolved in 80 g of methanol. In addition, 3.5 g of tetraethylammonium tetrafluoroborate conductive salt (16.12 mmol) were added. The beaker was filled with this solution. A substrate-free solution consisting of 0.16 M tetraethylammonium tetrafluoroborate in methanol was added to the counterelectrode chamber, which was divided off by the membrane.

The experiment was run under potentiostatic conditions analogously to Ex. 14.

After an experimental period of 4.5 h and a charge flow of 2500 coulombs (corresponding to an average current flow of 154 mA), the experiment was ended. The conversion at this time was 79%, and the in situ target product yield was determined as 79%. The enantiomer ratio I:ent-(I) was determined as 50:50.

Example 18

Reduction of Compound M1b(R) (0.6 g Batch)

The construction used was again a three-electrode system as described in Example 13.

0.6 g of the compound M1b(R) (1.59 mmol) obtained from Example 12b was dissolved in a solvent mixture consisting of 50 g of methanol and 50 g of N,N-dimethylformamide. In addition, 6 g of tetraethylammonium tetrafluoroborate conductive salt (27.64 mmol) were added. The beaker was filled with this solution. A substrate-free solution consisting of 0.24 M tetraethylammonium tetrafluoroborate in methanol was added to the counterelectrode chamber, which was divided off by the membrane.

The experiment was run under potentiostatic conditions analogously to Ex. 14.

After an experimental period of 4.5 h and a charge flow of 1187 coulombs (corresponding to an average current flow of 73 mA), the conversion was 98% and the in situ target product yield was determined as 95%. The enantiomer ratio (I):ent-(I) was determined as 83:17.

Example 19

Reduction of Compound M1b(R) (0.6 g Batch)

The construction and experimental conditions were chosen analogously to Ex. 18, except that the working electrode used was a porous carbon electrode (from: ALS).

The experiment was run under potentiostatic conditions analogously to Ex. 14.

After an experimental period of 3 h and 10 min and a charge flow of 494 coulombs (corresponding to an average current flow of 43 mA), the conversion was 100% and the in situ target product yield was determined as 97%. The enantiomer ratio I:ent-(I) was determined as 52:48.

Example 20

Reduction of Compound M1b(R) (Flow Cell)

In further examples, instead of the beaker cell, a flow cell (Micro Flow Cell) from Electrocell was used. The working electrode used was a platinum-coated titanium electrode. The counter-electrode used was graphite. The anolyte and catholyte chambers were separated from one another by means of a cation exchange membrane (fumapem F-9100-PK type from Fumatech). The membrane was immersed in demineralized water beforehand and installed in the moist state. On completion of assembly of the cell, it was purged with methanol. By means of peristaltic pumps [type: Sci-Q 323; company: Watson Marlow], it was possible first to convey the methanol purge and later the reaction solutions continuously through the two half-cells (6 l/h in each case).

The current and voltage source used was a potentiostat from Gamry [type: Reference 3000].

1 g of the compound M1b(R) (2.66 mmol) obtained from Example 11b was dissolved in a solvent mixture consisting of 4 g of methanol and 190 g of DMF. In addition, 4.5 g of tetraethylammonium tetrafluoroborate conductive salt (20.73 mmol) were added. This solution was used to fill the catholyte circuit via a reservoir vessel integrated within the circuit. An analogous solution without the compound M1b (R) was introduced into the anolyte circuit.

In the experiment, the current flow was limited to max. 300 mA. After a charge flow of about 1000 C (corresponding to 4 F), the conversion was 63% and, after a total of 3000 C (12 F), conversion was >94%. No significant by-products were observed.

Example 21

Preparation of Racemic (XIII) from Racemic M1(XVII)

The electrolysis cell used was again the Micro Flow Cell from Electrocell as described in Example 20. In a departure from Example 20, on this occasion, 10 g (26.6 mmol) of the compound rac. M1, obtained from Example 12, were dissolved in a solvent mixture consisting of 4 g of methanol and 190 g of DMF. In addition, 4.5 g of tetraethylammonium tetrafluoroborate conductive salt (20.73 mmol) were added. This solution was used to fill the catholyte circuit. An analogous solution without reactant was introduced into the anolyte circuit.

After a charge flow of 30 000 C (12 F), the electrochemical reduction was stopped. The yield of rac. (XIII) determined in situ by means of HPLC (Method E) was 95%. The catholyte solution was subsequently sent to workup.

Isolation of rac-(XIII): The solvent was first substantially distilled off and then the product was precipitated by a water precipitation (addition of water), filtered off and dried. The crude product thus obtained can be recrystallized from ethanol or THF and subjected to another enantiomer separation by means of SMB.

Example 30

Synthesis of Racemic (XIII) from Racemic M1 (XVII): Reduction of the Atropisomer Mixture Composed of 50 wt % M1b (R) and 50 wt % M1a (S) (Batch of 10 g)

In further examples, instead of the beaker cell, a flow cell (Micro Flow Cell 10 cm2 electrode surface) from Electrocell was used. The working electrode used was a platinum-coated titanium electrode. The counter electrode used was graphite. The anolyte and catholyte chambers were separated from one another by means of a cation exchange membrane (Nafion® N-424 from Dupont). The membrane was immersed in demineralized water beforehand and installed in the moist state. On completion of assembly of the cell, it was purged with a mixture composed of 20 wt % Methanol and 80 wt % DMF. By means of peristaltic pumps [type: Sci-Q 323; company: Watson Marlow], it was possible first to convey the methanol/DMF purge and later the reaction solutions continuously through the two half-cells (5 kg/h in each case). Through a separate cooling circuit, both the electrolyte solutions (Anolyte and Catholyte) are maintained at 20° C. As current and voltage source a potentiostat is used (Reference 3000 from Gamry).

10 g of the compound rac.M1 (26.6 mmol) obtained from Example 12b were dissolved in a solvent mixture consisting of 21.4 g of methanol and 85.6 g of DMF. In addition, 1.25 g of tetraethylammonium tetrafluoroborate conductive salt (5.76 mmol) and 1.45 g acetic acid (24.17 mmol) were added. This solution was used to fill the catholyte circuit via a reservoir vessel integrated within the circuit. An analogous solution without the compound rac.M1 was introduced into the anolyte circuit (anolyte amount at the start of experiment 358.7 g).

In the experiment a galvanostatic control was used. The constant current was set to 350 mA. After 20 h the experiment was stopped and both half cells emptied from the electrolytes. The conversion of the compound rac.M1 was 99%. The in-situ Yield of the target compound (XIII) was after 20 h>98%. No significant amount of side components was observed. The product selectivity (to XIII) was approx. 99%. The product concentration at the end of the experiment was approx. 37 mg/g. The dilution results from a transfer of solvent from Anolyte to Catholyte (Total mass of the Catholyte and Anolyte after emptying of the cell was 264 and 214 g respectively). Isolation of rac-(XIII): After removal of the solvent (DMF/MeOH) and the conducting salt, the product was obtained in high yield and purity.

Example 31

Synthesis of Racemic (XIII) from Racemic M1 (XVII): Reduction of the Atropisomer Mixture Composed of 50 wt % M1b (R) and 50 wt % M1a (S) (Batch of 10 g)

It was used the same equipment and procedure described in example 30.

Differently 10 g of the compound rac.M1 (26.6 mmol) obtained from Example 12b were dissolved in a solvent mixture consisting of 16.6 g of methanol and 66.4 g of DMF. In addition, 0.97 g of tetraethylammonium tetrafluoroborate conductive salt (4.47 mmol) and 1.09 g acetic acid (18.1 mmol) were added. This solution was used to fill the catholyte circuit via a reservoir vessel integrated within the circuit. An analogous solution without the compound rac.M1 was introduced into the anolyte circuit (anolyte amount at the start of experiment 282 g).

In the experiment a galvanostatic control was used. The constant current was set to 400 mA. After approx. 6 h the Catholyte became turbid and in the liquid reservoir a white precipitate was observed. After 10 h the experiment was stopped. The precipitate was filtered (1.7 g) and without any further purification, analyzed by HPLC. It was found to be racemic (XIII) with an area % above 99.6%. In the remaining mother liquor a ratio between the target product (XIII) and the starting material (rac. M1(XVII)) of 89:10 area % was observed (HPLC analysis). No significant amount of side components was observed. The product selectivity (to XIII) was approx. 99%. The product concentration in the mother liquor at the end of the experiment was approx. 43 mg/g. The total mass of the Catholyte and Anolyte after emptying of the cell was 174 and 197 g respectively.

Example 32

Synthesis of Racemic (XIII) from Racemic M1 (XVII): Reduction of the Atropisomer Mixture Composed of 50 wt % M1b (R) and 50 wt % M1a (S) (Batch of 36 g)

In this example a Multipurpose Cell (MPC 100 cm2 electrode surface) from Electrocell was used. The working electrode used was a platinum-coated titanium electrode. The counter electrode used was graphite. The anolyte and catholyte chambers were separated from one another by means of a cation exchange membrane (Nafion® N-424 from Dupont). The membrane was immersed in demineralized water beforehand and installed in the moist state. On completion of assembly of the cell, it was purged with a mixture composed of 20 wt % Methanol and 80 wt % DMF. By means of centrifugal pump [type: Labor-Reaktionsmischer HMR 050; company: Fink] and a Coriflow Massflow Controller (Company: Bronkhorst), it was possible first to convey the methanol/DMF purge and later the reaction solutions continuously through the two half-cells (50 kg/h in each case). Through a separate cooling circuit, connected to a cryostat (Type FP45 from Julabo) both the electrolyte solutions (Anolyte and Catholyte) are maintained at 22° C. As current and voltage source a rectifier from the company Delta Elektronika is used (Type ES030-10).

After purging the anolyte and catholyte circulation for at least 15 minutes, the following solution are filled in the reservoirs:

Catholyte: 36 g (95.7 mmol) of the compound rac.M1 (XVII) obtained from Example 12b were dissolved in a solvent mixture consisting of 100 g of methanol and 400 g of DMF. In addition, 6 g of tetraethylammonium tetrafluoroborate conductive salt (27.64 mmol) and 5 g acetic acid (83.3 mmol) were added.

Anolyte: Here will be used a substrate free solution composed of 250 g Methanol, 1000 g DMF, 15 g (69.1 mmol) conductive salt (Et4NBF4) and 12.5 g (208.3 mmol) acetic acid.

In the experiment a galvanostatic control was used. The constant current was set to 3 A. After 10 h the experiment was stopped and both half cells emptied from the electrolytes. The conversion of the compound rac.M1 was 95.7% (HPLC area %). The in-situ Yield of the target compound (XIII) was after 10 h 95.3% (HPLC area %). No significant amount of side components was observed. The product selectivity (to XIII) was >99.5%. The product concentration at the end of the experiment was >2.6 wt %. The dilution results from a transfer of solvent from Anolyte to Catholyte (Total mass of the Catholyte and Anolyte after emptying of the cell was 1296 and 482 g respectively).

Isolation of rac-(XIII): After removal of the solvent (DMF/MeOH) and the conducting salt, the product was obtained in high yield and purity. The recovered raw product can be additionally recrystallized in Ethanol or THF and an enantiomeric separation via SMB can be performed.

Example 22

Single-Crystal X-Ray Structure Analysis of the Compound of the Formula M1b(R): (R)-4-(4-cyano-2-methoxyphenyl)-5-ethoxy-2,8-dimethyl-1, 6-naphthyridine-3-carboxamide Analysis method: Single-crystal x-ray structure analysis
Crystal analysed: colourless block, 0.40×0.20×0.20 mm$^3$
Experimental:
The crystal structure determination was conducted with the aid of a diffractometer (Oxford Diffraction, Xcalibur series), equipped with a CCD area detector (Ruby model), a sealed x-ray tube with CuKa radiation, osmium reflector as monochromator and a cryojet cooling device for low-temperature measurements (T=100 K).

360° data collection, omega and phi scan. Programs used: Data recording and reduction with Crysalis (Oxford Diffraction 2007). The crystal structure solution was conducted by means of direct methods as implemented in SHELXTL Version 6.10 (Sheldrick, University of Göttingen (Germany), 2000), and visualized by means of the XP program. Missing atoms were subsequently localized with the aid of difference Fourier synthesis and added to the atom list. The refinement by the method of least mean squares to F2 was conducted with all intensities measured and conducted with the program SHELXTL Version 6.10 (Sheldrick, University of Göttingen (Germany), 2000). All non-hydrogen atoms were refined, including anisotropic deflection parameters.

Crystal data and structure refining of the compound of the formula M1b(R): (R)-4-(4-cyano-2-methoxyphenyl)-5-ethoxy-2,8-dimethyl-1,6-naphthyridine-3-carboxamide
Identification code: M1b
Empirical formula: C21 H20N4 O3
Molecular mass: 376.41
Temperature: 100 K
Wavelength: 1.54178 Å
Crystal system: orthorhombic
Space group: P2(1)2(1)2(1)
Lattice constants: a=9.70950(10) Å lattice
b=10.67390(10) Å□=90°.
c=18.9480(2) Å□□=90°.
Volume: 1963.74(3) Å$_3$
Z4
Specific density (calculated): 1.273 Mg/m$^3$
Absorption coefficient: 0.714 mm-1
F(000) 792
Crystal dimensions: 0.40×0.20×0.20 mm3
Theta range for data recording: 4.67 to 65.66°.
Index range: −11≤h≤9, −12≤k≤12, −19≤l≤22
Reflections recorded: 15493
Independent reflections: 3367 [R(int)=0.0230]
Completeness at theta=65.66° 99.5%
Absorption correction: Crysalis
Refinement method: full matrix method of least mean squares to F$_2$
Data/restrictions/parameters: 3367/0/257
Quality of fit to F$_2$: 1.048
Final R values: [I>2sigma(I)] R1=0.0242, wR2=0.0636
R values (all data): R1=0.0249, wR2=0.0641
Absolute structure parameter: −0.18(13)
Greatest and smallest differential density: 0.142 and −0.139 e.Å$_{-3}$ X-Ray Structure Analysis:

The x-ray structure analysis showed that, when the 1,6-naphthyridine-3-carboxamide ring system is in the plane of the paper, the 4-cyano-2-methoxyphenyl substituent is at right angles thereto, in which case the methoxy group is then behind the plane of the paper.

Determination of Absolute Configuration

| Chirality test* | Correct structure | Inverted structure |
|---|---|---|
| Flack parameter (standard deviation) | −0.1838(0.1347) | 1.1745(0.1364) |
| Twin Basf (standard deviation) | 0.0000(0.1348) | 1.1855(0.1347) |
| wR2 value (with Flack parameter) | 0.0641 | 0.0649 |
| Chirality | Ra | Sa |

H. D. Flack, *Acta Cryst.*, 1983, A39, 876-881
H. D. Flack, G. Bernardinelli, *Acta Cryst.*, 1999, A55, 908-915
H. D. Flack, G. Bernardinelli, *J. Appl. Cryst.*, 2000, 33, 1143-1148.

The Compound of the Formula M1b(R) Thus has the Absolute Configuration R (Ra).

The naming of the absolute configuration follows the Cahn-Ingold-Prelog rules for compounds having axial chirality.

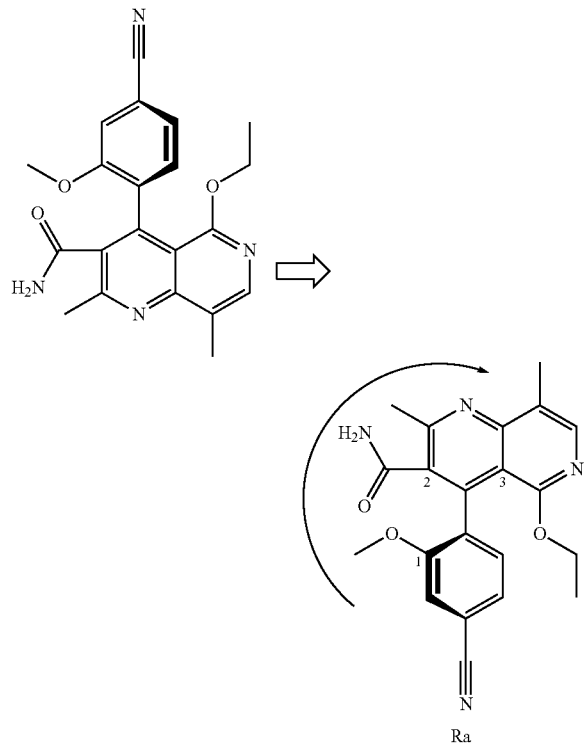

Example 23

Determination of the Absolute Configuration of the Mb Series by Correlation of the CD Spectra (See FIG. 7)

Physicochemical Characterization of Compound of the Formula (I) in Crystalline Form of Polymorph I Compound of the formula (I) in crystalline form of polymorph I melts at 252° C., ΔH=95-113 Jg$^{-1}$ (heating rate 20 Kmin$^{-1}$).

A depression of the melting point was observed depending on the heating rate.

The melting point decreases at a lower heating rate (e.g. 2 Kmin$^{-1}$) since decomposition occurs.

No other phase transitions were observed. A loss of mass of about 0.1% was observed up to a temperature of 175° C.

Stability and Moisture Absorption

Samples of compound of the formula (I) in crystalline form of polymorph I were stored at 85% and 97% rel. humidity (25° C.). The samples were evaluated after 12 months by DSC, TGA and XRPD. After 12 months, a mass change of <0.1% is observed in both cases. This means that compound of the formula (I) in crystalline form of polymorph I shows no significant absorption of water under these storage conditions. According to DSC, TGA and XRPD, no difference exists in compound of the formula (I) in crystalline form of polymorph I.

HPLC Conditions/Methods
Method A
YMC Hydrosphere C18
150*4.6 mm, 3.0 μm
25° C., 1 ml/min, 270 nm, 4 nm
0':70% TFA 0.1%*; 30% acetonitrile
17':20% TFA 0.1%*; 80% acetonitrile
18':70% TFA 0.1%*; 30% acetonitrile
*: TFA in water
Method B
YMC Hydrosphere C18
150*4.6 mm, 3.0 μm
25° C., 1 ml/min, 255 nm, 6 nm
0':90% TFA 0.1%*; 10% acetonitrile
20':10% TFA 0.1%*; 90% acetonitrile
18':10% TFA 0.1%*; 90% acetonitrile
Method C
Nucleodur Gravity C18
150*2 mm, 3.0 μm
35° C., 0.22 ml/min., 255 nm, 6 nm
Solution A: 0.58 g of ammonium hydrogen phosphate and 0.66 g of ammonium dihydrogen phosphate in 1 l of water (ammonium phosphate buffer pH 7.2)
Solution B: acetonitrile
0':30% B; 70% A
15':80% B; 20% A
25':80% B; 20% A
Method D
Column length: 25 cm
Internal diameter: 4.6 mm
Packing: Chiralpak IA, 5 μm
Reagents: 1. Acetonitrile HPLC grade
2. Methyl tert-butyl ether (MTBE), p.a.
Test solution The sample is dissolved at a concentration of 1.0 mg/ml in acetonitrile.
(e.g. about 25 mg of sample, weighed accurately, dissolved in acetonitrile to 25.0 ml).
Eluent A. acetonitrile
B. Methyl tert-butyl ether (MTBE), p.a.
Flow rate 0.8 ml/min
Column oven temperature 25° C.
Detection measurement wavelength: 255 nm
Range: 6 nm
Injection volumes 5 μl
Mix composition of eluents A and B in ratio by volume of 90:10
Chromatogram run time 30 min Retention times/RRT:
(4S)-4-(4-cyano-2-methoxyphenyl)-5-ethoxy-2,8-dimethyl-1,4-dihydro-1,6-naphthyridine-3-carboxamide (1) about 11 min. RRT: 1.00
(4R)-4-(4-cyano-2-methoxyphenyl)-5-ethoxy-2,8-dimethyl-1,4-dihydro-1,6-naphthyridine-3-carboxamide (1) about 9 min. RRT: 0.82
Method E
YMC Hydrosphere C18
150*4.6 mm, particle size 3 µm
25° C., 1 ml/min, typical starting pressure: about 160 bar
Measurement wavelength: 255 nm, range: 6 nm
Gradient:
0':90% formic acid 0.1%*; 10% acetonitrile
20':10% formic acid 0.1%; 90% acetonitrile
25':90% formic acid 0.1%; 10% acetonitrile
*: formic acid in water
Retention times:
Compound I or ent-(I): about 9.9 min
Compound M1a or M1b: about 15.5 min
Method F
Chiralpak IA
150*4.6 mm, particle size 5 µm
25° C., 0.8 ml/min
Measurement wavelength: 255 nm, range: 6 nm
Mobile phase: acetonitrile+tert-butyl methyl ether (MTBE) mixed in a volume ratio of 90:10
Retention times:
Compound of the formula M1b(R): about 5.1 min
Compound of the formula M1a(S): about 5.5 min
Compound of the formula (I): about 8.6 min
Compound of the formula ent-(I): about 10.8 min

DESCRIPTION OF THE FIGURES

FIG. 1: Thermal racemization of the compound of the formula ent-(I) in 1-butanol without addition of a catalytic amount of acid.

FIG. 2: Thermal racemization of the compound of the formula ent-(I) in 1-butanol with and without addition of a catalytic amount of acid.

FIG. 3: Standard types of electrochemical cells. Beaker cell, "H" cell and filter press flow cell.

FIG. 4: Reaction scheme of the mediated electrochemical oxidation of ent-(I) to (XVII) by DDQ.

FIG. 5: Cyclic voltammetry of DDQ, DHP and the compound of the formula ent-(I) and the DDQ:DHP (V) 1:10 mixture according to Examples 24 and 25

FIG. 6: Evolution of DHP ent-(I) reactant and PYR product (XVII) measured by means of HPLC as a function of time according to Example 26. The lines represent the values calculated based solely on electron flow and 100% power efficiency.

FIG. 7: CD spectrum of the compound of the formula M1b(R) (in acetonitrile)

FIG. 8: Crystal structure of the compound of the formula M1b(R): (R)-4-(4-cyano-2-methoxyphenyl)-5-ethoxy-2,8-dimethyl-1,6-naphthyridine-3-carboxamide FIG. 9: Crystal structure of the compound of the formula M1b(R): (R)-4-(4-cyano-2-methoxyphenyl)-5-ethoxy-2,8-dimethyl-1,6-naphthyridine-3-carboxamide

The invention claimed is:
1. A process for preparing compounds of the formulae M1a(S) and M1b(R)

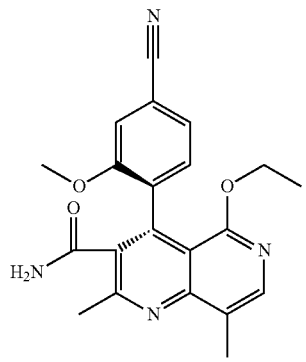

M1a(S)

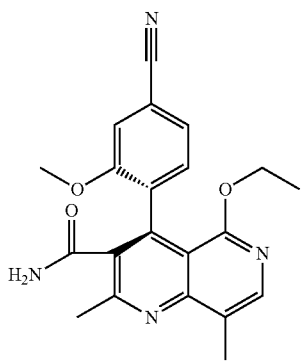

M1b(R)

comprising oxidizing the compound of the formula ent-(I)

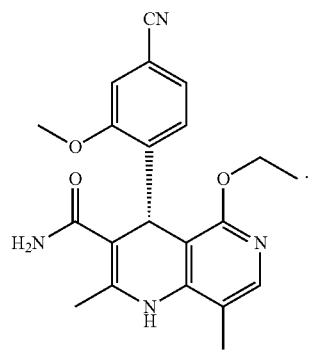

ent-(I)

2. A process for preparing compounds of the formulae M1a(S) and M1b(R) according to claim 1, characterized in that the oxidation is conducted with chemical oxidizing agents.

3. A process for preparing the racemic compound of the formula (XVII)

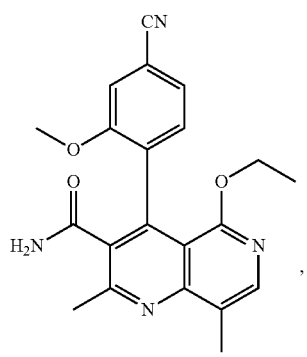

(XVII)

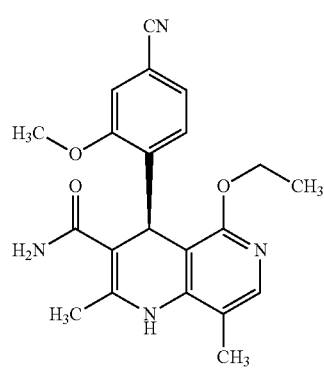

(I)

comprising thermally racemizing a mixture of the compounds of the formulae MIa(S) and MIb(R)

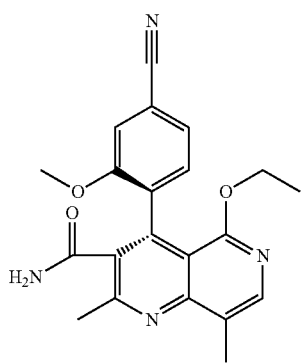

MIa(S)

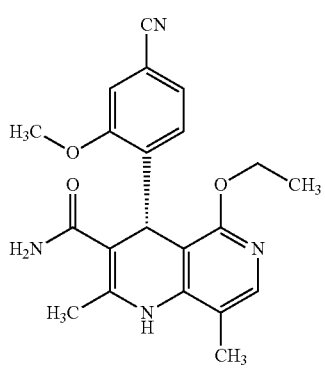

ent-(I)

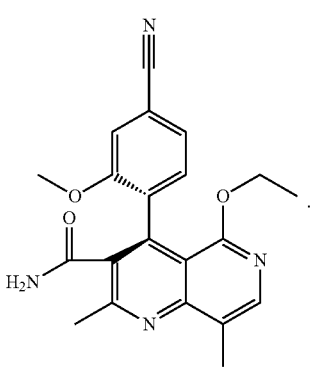

MIb(R)

comprising electrochemically reducing compounds of the formulae (XVII) or M1a(S) or M1b(R) or a mixture of M1a(S) and M1b(R)

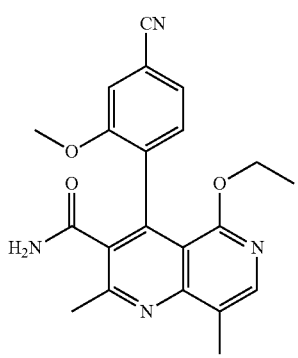

(XVII)

4. A process for preparing the compound of the formula (XVII) according to claim 3, characterized in that a mixture of the compounds of the formulae M1a(S) and M1b(R) is racemized at a temperature of 70 to 110° C. with or without addition of an acid.

5. A process for preparing compounds of the formula (I) and ent-(I)

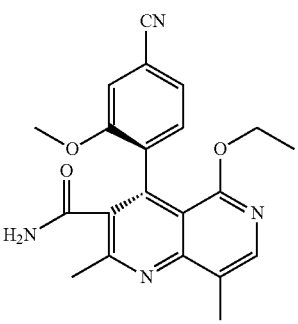

M1a(S)

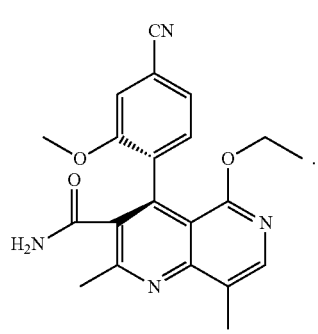

M1b(R)

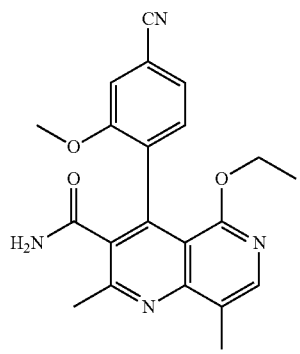

(XVII)

6. A process for preparing the compounds of the formulae (I) and ent-(I) according to claim 5, characterized in that the electrochemical reduction is conducted in a beaker cell or flow cell in the presence of methanol.

7. A process for preparing compounds of the formulae (I) and ent-(I) according to claim 1, 3 or 5

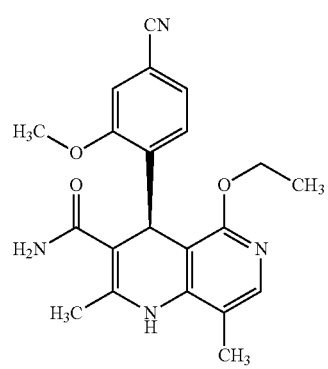

(I)

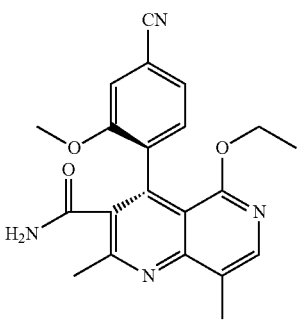

M1a(S)

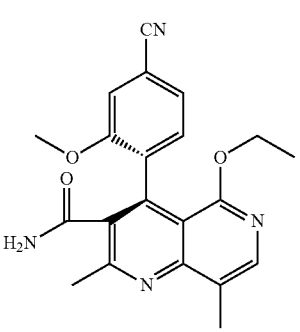

M1b(R)

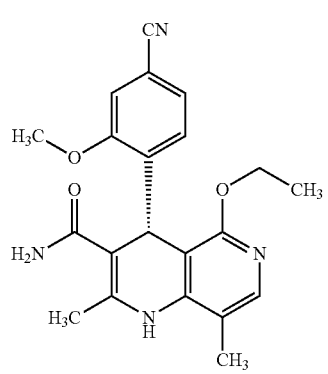

ent-(I)

characterized in that compounds of the formulae (XVII) or M1a(S) or M1b(R) or a mixture of M1a(S) and M1b(R) are electrochemically reduced, and characterized in that the compounds of the formulae (XVII), M1a(S) and M1b(R) are obtained by thermal isomerization of compounds of the formulae M1a(S) and M1b(R)

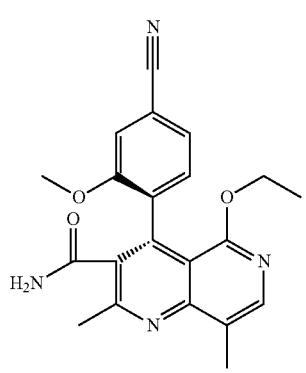
M1a(S)
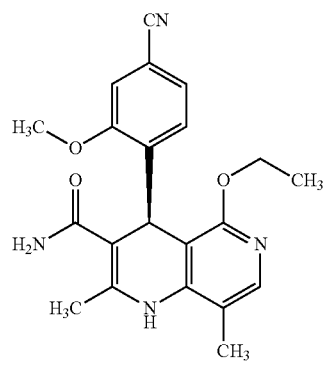
(I)
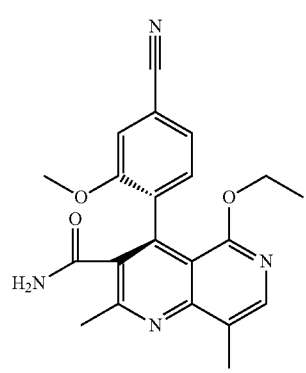
M1b(R)
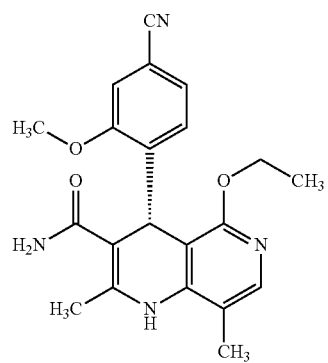
ent-(I)
and characterized in that the compound of the formula ent-(I)
characterized in that compounds of the formulae (XVII) or M1a(S) or M1b(R) or a mixture of M1a(S) and M1b(R)
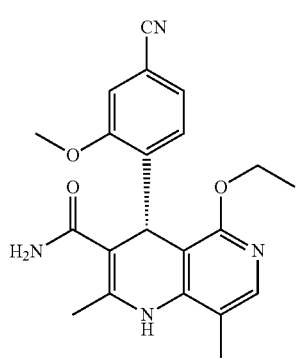
ent-(I)
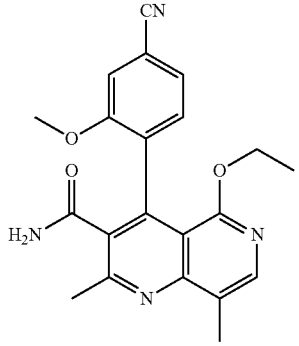
(XVII)
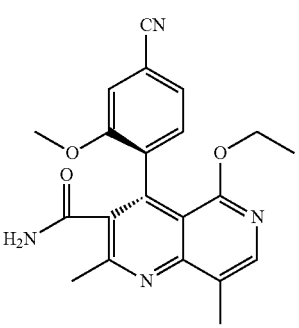
M1a(S)
is oxidized.
8. A process for preparing compounds of the formulae (I) and ent-(I) according to claim 5

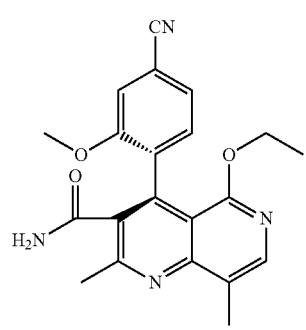
M1b(R)
are electrochemically reduced in a beaker cell or flow cell in the presence of methanol,
and characterized in that the compounds of the formulae (XVII), M1a(S) and M1b(R) are obtained by thermal isomerization of compounds of the formulae M1a(S) and M1b(R)
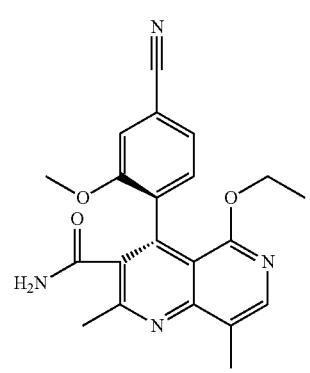
M1a(S)
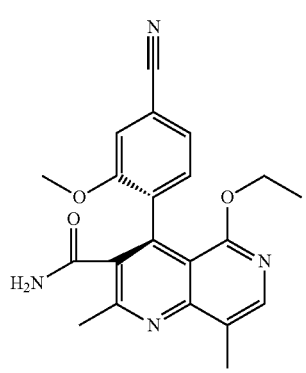
M1b(R)
and characterized in that the compound of the formula ent-(I)
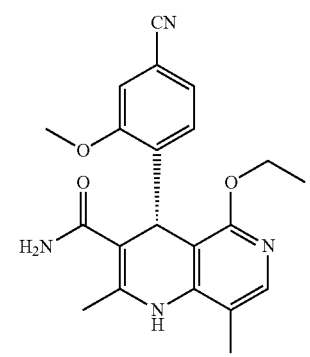
ent-(I)
is oxidized with chemical oxidizing agents.
* * * * *